(12) United States Patent
Beachy et al.

(10) Patent No.: US 7,291,626 B1
(45) Date of Patent: *Nov. 6, 2007

(54) INHIBITORS OF HEDGEHOG SIGNALING PATHWAYS, COMPOSITIONS AND USES RELATED THERETO

(75) Inventors: Philip A. Beachy, Ruxton, MD (US); Michael K. Cooper, Baltimore, MD (US); Jeffrey A. Porter, Belmont, MA (US)

(73) Assignee: John Hopkins University School of Medicine, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/708,964

(22) Filed: Nov. 8, 2000

Related U.S. Application Data

(63) Continuation of application No. 09/685,244, filed on Oct. 10, 2000, now abandoned, which is a continuation-in-part of application No. PCT/US99/07811, filed on Apr. 9, 1999.

(60) Provisional application No. 60/081,186, filed on Apr. 9, 1998, provisional application No. 60/081,263, filed on Apr. 9, 1998.

(51) Int. Cl.
*A61K 31/4355* (2006.01)
(52) U.S. Cl. .................................... 514/278
(58) Field of Classification Search ............... 514/278
See application file for complete search history.

(56) References Cited

U.S. PATENT DOCUMENTS

| 3,673,175 | A | 6/1972 | Schramm et al. |
| 5,958,770 | A | 9/1999 | Cham et al. |
| 6,057,091 | A | 5/2000 | Beachy et al. |
| 6,495,532 | B1 | 12/2002 | Bathurst et al. |

FOREIGN PATENT DOCUMENTS

| EP | 0020029 | 5/1980 |
| EP | 0375349 | 12/1989 |
| EP | 0 495 684 A1 | 7/1992 |
| GB | 1227728 | 4/1971 |
| JP | 04230696 | 12/1990 |
| WO | WO91/10743 | 7/1991 |
| WO | WO96/35412 A1 | 11/1996 |
| WO | WO98/58650 | 12/1998 |

OTHER PUBLICATIONS

Gerashchenko et al., "Antiinflammatory activity of jervine", Aktual. Vop. Farm., pp. 169-171, 1970.*
Campbell et al., "Inhibition of Limb Chondrogenesis by a Veratrum Alkaloid: Temporal Specificity in Vivo and in Vitro", Dev. Biol. 111: 464-470 (1985).
Gaffield et al., "Craniofacial Malformations Induced in Hamsters by Steroidal Alkaloids", J. Nat. Toxins 5 (1): 25-38 (1996).
Gerashchenko, G. I. et al. "Antiinflammatory activity of jervine", Aktual. Vop. Farm.: 169-171 (1970).
Johnson et al., "The Synthesis of Veratramine", JACS 89: 17 (1967).
Kutney et al., "Synthetic Studies in the Veratrum Alkaloid Series II: The Total Synthesis of Verarine, Veratramine, Jervine, and Veratrobasine", Can. J. Chem. 53: 1796-1817 (1975).
Levetin, Estelle & McMahon, Karen. "Plants and Society", Wm. C. Brown Publishers, Times Mirror Higher Education Group (1996).
Masamune et al., "Communications to the Editor: The Synthesis of Jervine and Related Alkaloids", JACS 89: 17 (1967).
"Merck Index: An Encyclopedia of Chemical, Drugs, and Biologicals, 11th Ed.", Merck & Co., Inc.: 828.
Omnell et al., "Expression of Veratrum, Alkaloid Teratogenicity in the Mouse", Teratology 42: 105-119 (1990).
Smith, Carolyn M. et al. 5x-Reductase Expression by Prostate Cancer Cell Lines and Benign Prostatic Hyerplasia iin Vitro. J. Clin Endocrin. Metab. 81 (4): 1361-1366 (1996).
"*Veratrum californicum*", Visitors Guide, Wrights lake, CA.
Badria et al., "Time Course and Inhibition of Stavaroside K, Sincerelyeratramin and Cervine-Iduced Hemolysis by Other Pregnane Glycosides and Beratrum Alkaloids," *Pharmazie* 50:421-423 (1995).
Brown et al., "Structure-Activity Relation of Steroid Teratogens. 2. N-Substituted Jervines," *J. Agric. Food Chem.* 26:564-566 (1978).
Masamune et al., "Synthesis and NMR Spectra of 22,27-Imino-17,23-Oxidojervane Derivatives," *Tetrahedron* 23:1591-1612 (1967).

* cited by examiner

*Primary Examiner*—Barbara P. Badio
(74) *Attorney, Agent, or Firm*—Ropes & Gray LLP

(57) ABSTRACT

The present invention makes availables assays and reagents inhibiting paracrine and/or autocrine signals produced by a hedgehog protein or aberrant activation of a hedgehog signal transduction pathway, e.g., which involve the use of a steroidal alkaloid or other small molecule.

17 Claims, 20 Drawing Sheets

AY9944

TRIPARANOL

JERVINE

CYCLOPAMINE

TOMATIDINE

CHOLESTEROL

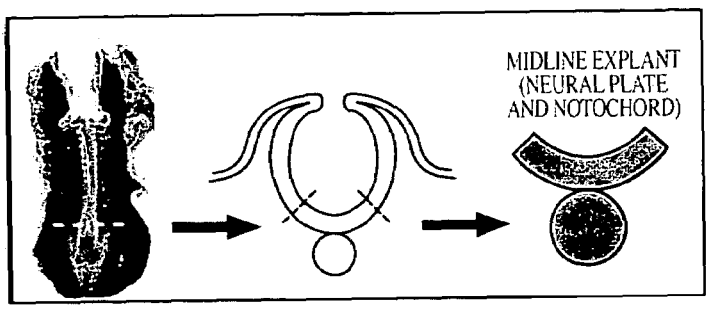
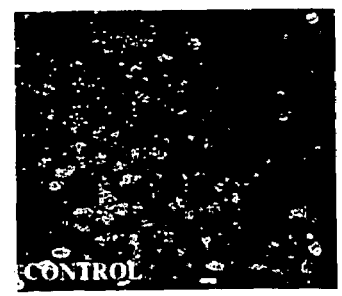
Fig. 3A  Fig. 3B
 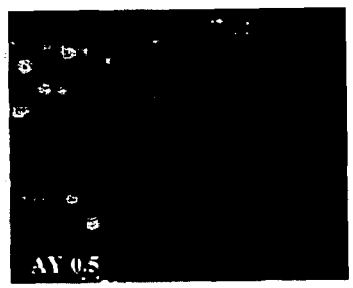 
Fig. 3C  Fig. 3D  Fig. 3E
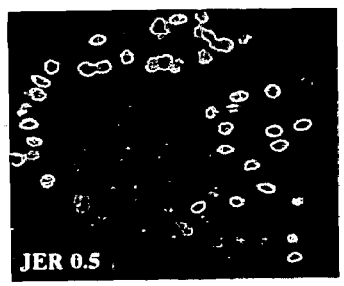 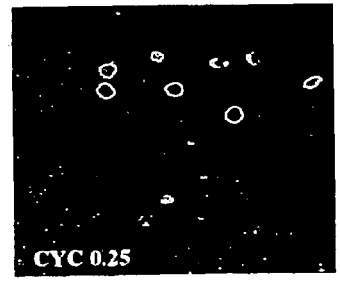 
Fig. 3F  Fig. 3G  Fig. 3H
  
Fig. 3I  Fig. 3J  Fig. 3K SHH-N 6.25 nM
☐ ISL1  ■ HNF3β

SHH-N25 nM
☐ ISL1  ■ HNF3β

SHH-N 2 nM
☐ PAX7   ■ HNF3β

SHH-N 2 nM
☐ PAX7   ■ HNF3β

SHH-N 2 nM
☐ PAX7   ■ HNF3β

SHH-N 2 nM
☐ PAX7   ■ HNF3β

SHH-N 2 nM
☐ PAX7   ■ HNF3β

SHH-N 2 nM
□ISL1  ■HNF3β

SHH-N 2 nM
□ISL1  ■HNF3β

SHH-N 2 nM
□ISL1  ■HNF3β

SHH-N 2 nM
□ISL1  ■HNF3β

SHH-N 2 nM
□ISL1  ■HNF3β

SHH-N 25 nM
☐ISL1  ■HNF3β

SHH-N 25 nM
☐ISL1  ■HNF3β

SHH-N 25 nM
☐ISL1  ■HNF3β

SHH-N 25 nM
☐ISL1  ■HNF3β

SHH-N 25 nM
☐ISL1  ■HNF3β

Control
Fig. 8A
Shh -/-
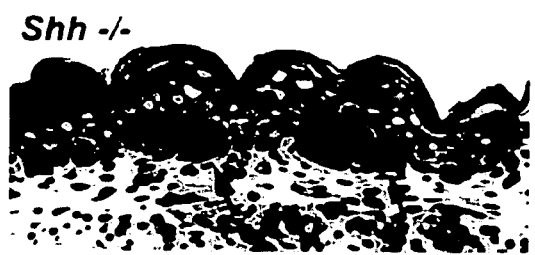
Fig. 8B
Control                    Shh -/-
Gli1 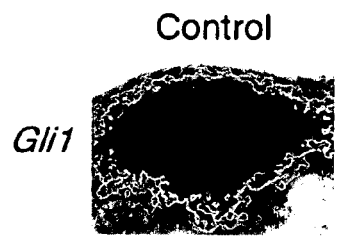      Gli1 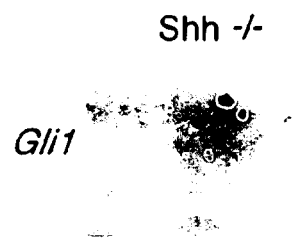
Fig. 8C                    Fig. 8D
Control                    Shh -/-
Ptc1 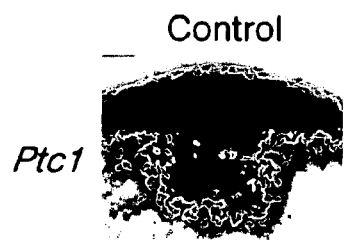     Ptc1 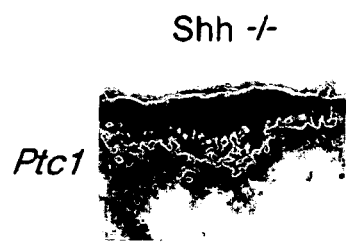
Fig. 8E                    Fig. 8F
Control                    Shh -/-
BMP-4 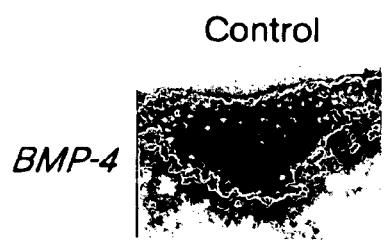    BMP-4 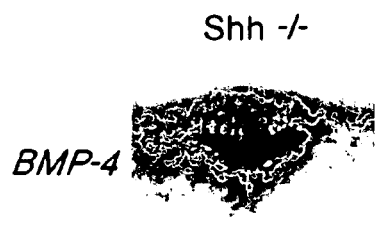
Fig. 8G                    Fig. 8H Control Shh -/-

Control

Shh -/-

Control

Shh -/-

INHIBITORS OF HEDGEHOG SIGNALING PATHWAYS, COMPOSITIONS AND USES RELATED THERETO

This application is a continuation of U.S. application Ser. No. 09/685,244, filed Oct. 10, 2000, now abandoned, which is a continuation-in-part of PCT Application No. US99/07811, filed Apr. 9, 1999, based on U.S. application Ser. No. 09/090,622, filed Jun. 4, 1998, now U.S. Pat. No. 6,432,970, which claims priority to U.S. Provisional Application Nos. 60/081,186 and 60/081,263, filed Apr. 9, 1998, the specifications of all of which are hereby incorporated herein by reference in their entirety.

BACKGROUND OF THE INVENTION

Pattern formation is the activity by which embryonic cells form ordered spatial arrangements of differentiated tissues. The physical complexity of higher organisms arises during embryogenesis through the interplay of cell-intrinsic lineage and cell-extrinsic signaling. Inductive interactions are essential to embryonic patterning in vertebrate development from the earliest establishment of the body plan, to the patterning of the organ systems, to the generation of diverse cell types during tissue differentiation (Davidson, E., (1990) *Development* 108: 365-389; Gurdon, J. B., (1992) *Cell* 68: 185-199; Jessell, T. M. et al., (1992) *Cell* 68: 257-270). The effects of developmental cell interactions are varied. Typically, responding cells are diverted from one route of cell differentiation to another by inducing cells that differ from both the uninduced and induced states of the responding cells (inductions). Sometimes cells induce their neighbors to differentiate like themselves (homeogenetic induction); in other cases a cell inhibits its neighbors from differentiating like itself. Cell interactions in early development may be sequential, such that an initial induction between two cell types leads to a progressive amplification of diversity. Moreover, inductive interactions occur not only in embryos, but in adult cells as well, and can act to establish and maintain morphogenetic patterns as well as induce differentiation (J. B. Gurdon (1992) *Cell* 68:185-199).

Members of the Hedgehog family of signaling molecules mediate many important short- and long-range patterning processes during invertebrate and vertebrate development. In the fly, a single hedgehog gene regulates segmental and imaginal disc patterning. In contrast, in vertebrates, a hedgehog gene family is involved in the control of left-right asymmetry, polarity in the CNS, somites and limb, organogenesis, chondrogenesis and spermatogenesis.

The first hedgehog gene was identified by a genetic screen in the fruitfly *Drosophila melanogaster* (Nüsslein-Volhard, C. and Wieschaus, E. (1980) *Nature* 287, 795-801). This screen identified a number of mutations affecting embryonic and larval development. In 1992 and 1993, the molecular nature of the *Drosophila* hedgehog (hh) gene was reported (C. F., Lee et al. (1992) *Cell* 71, 33-50), and since then, several hedgehog homologues have been isolated from various vertebrate species. While only one hedgehog gene has been found in *Drosophila* and other invertebrates, multiple Hedgehog genes are present in vertebrates.

The vertebrate family of hedgehog genes includes at least four members, e.g., paralogs of the single *drosophila* hedgehog gene. Exemplary hedgehog genes and proteins are described in PCT publications WO 95/18856 and WO 96/17924. Three of these members, herein referred to as Desert hedgehog (Dhh), Sonic hedgehog (Shh) and Indian hedgehog (Ihh), apparently exist in all vertebrates, including fish, birds, and mammals. A fourth member, herein referred to as tiggie-winkle hedgehog (Thh), appears specific to fish. Desert hedgehog (Dhh) is expressed principally in the testes, both in mouse embryonic development and in the adult rodent and human; Indian hedgehog (Ihh) is involved in bone development during embryogenesis and in bone formation in the adult; and, Shh, which as described above, is primarily involved in morphogenic and neuroinductive activities. Given the critical inductive roles of hedgehog polypeptides in the development and maintenance of vertebrate organs, the identification of hedgehog interacting proteins is of paramount significance in both clinical and research contexts.

The various Hedgehog proteins consist of a signal peptide, a highly conserved N-terminal region, and a more divergent C-terminal domain. In addition to signal sequence cleavage in the secretory pathway (Lee, J. J. et al. (1992) *Cell* 71:33-50; Tabata, T. et al (1992) *Genes Dev.* 2635-2645; Chang, D. E. et al. (1994) *Development* 120:3339-3353), Hedgehog precursor proteins undergo an internal autoproteolytic cleavage which depends on conserved sequences in the C-terminal portion (Lee et al (1994) *Science* 266:1528-1537; Porter et al. (1995) *Nature* 374: 363-366). This autocleavage leads to a 19 kD N-terminal peptide and a C-terminal peptide of 26-28 kD (Lee et al. (1992) supra; Tabata et al. (1992) supra; Chang et al. (1994) supra; Lee et al. (1994) supra; Bumcrot, D. A, et al. (1995) *Mol. Cell. Biol.* 15:2294-2303; Porter et al. (1995) supra; Ekker, S. C. et al. (1995) *Curr. Biol.* 5:944-955; Lai, C. J. et al. (1995) *Development* 121:2349-2360). The N-terminal peptide stays tightly associated with the surface of cells in which it was synthesized, while the C-terminal peptide is freely diffusible both in vitro and in vivo (Porter et al. (1995) *Nature* 374:363; Lee et al. (1994) supra; Bumcrot et al. (1995) supra; Mart', E. et al. (1995) *Development* 121:2537-2547; Roelink, H. et al. (1995) *Cell* 81:445-455). Interestingly, cell surface retention of the N-terminal peptide is dependent on autocleavage, as a truncated form of HH encoded by an RNA which terminates precisely at the normal position of internal cleavage is diffusible in vitro (Porter et al. (1995) supra) and in vivo (Porter, J. A. et al. (1996) *Cell* 86, 21-34). Biochemical studies have shown that the autoproteolytic cleavage of the HH precursor protein proceeds through an internal thioester intermediate which subsequently is cleaved in a nucleophilic substitution. It is likely that the nucleophile is a small lipophilic molecule which becomes covalently bound to the C-terminal end of the N-peptide (Porter et al. (1996) supra), tethering it to the cell surface. The biological implications are profound. As a result of the tethering, a high local concentration of N-terminal Hedgehog peptide is generated on the surface of the Hedgehog producing cells. It is this N-terminal peptide which is both necessary and sufficient for short- and long-range Hedgehog signaling activities in *Drosophila* and vertebrates (Porter et al. (1995) supra; Ekker et al. (1995) supra; Lai et al. (1995) supra; Roelink, H. et al. (1995) *Cell* 81:445-455; Porter et al. (1996) supra; Fietz, M. J. et al. (1995) *Curr. Biol.* 5:643-651; Fan, C.-M. et al. (1995) *Cell* 81:457-465; Mart', E., et al. (1995) *Nature* 375:322-325; Lopez-Martinez et al. (1995) *Curr. Biol* 5:791-795; Ekker, S. C. et al. (1995) *Development* 121:2337-2347; Forbes, A. J. et al. (1996) *Development* 122:1125-1135).

HH has been implicated in short- and long-range patterning processes at various sites during *Drosophila* development. In the establishment of segment polarity in early embryos, it has short-range effects which appear to be directly mediated, while in the patterning of the imaginal discs, it induces long range effects via the induction of secondary signals.

In vertebrates, several hedgehog genes have been cloned in the past few years. Of these genes, Shh has received most of the experimental attention, as it is expressed in different organizing centers which are the sources of signals that pattern neighboring tissues. Recent evidence indicates that Shh is involved in these interactions.

The expression of Shh starts shortly after the onset of gastrulation in the presumptive midline mesoderm, the node in the mouse (Chang et al. (1994) supra; Echelard, Y. et al. (1993) Cell 75:1417-1430), the rat (Roelink, H. et al. (1994) Cell 76:761-775) and the chick (Riddle, R D. et al. (1993) Cell 75:1401-1416), and the shield in the zebrafish (Ekker et al. (1995) supra; Krauss, S. et al. (1993) Cell 75:1431-1444). In chick embyros, the Shh expression pattern in the node develops a left-right asymmetry, which appears to be responsible for the left-right situs of the heart (Levin, M. et al. (1995) Cell 82:803-814).

In the CNS, Shh from the notochord and the floorplate appears to induce ventral cell fates. When ectopically expressed, Shh leads to a ventralization of large regions of the mid- and hindbrain in mouse (Echelard et al. (1993) supra; Goodrich, L. V. et al. (1996) Genes Dev. 10:301-312), Xenopus (Roelink, H. et al. (1994) supra; Ruiz i Altaba, A. et al. (1995) Mol. Cell. Neurosci. 6:106-121), and zebrafish (Ekker et al. (1995) supra; Krauss et al. (1993) supra; Hammerschmidt, M., et al. (1996) Genes Dev. 10:647-658). In explants of intermediate neuroectoderm at spinal cord levels, Shh protein induces floorplate and motor neuron development with distinct concentration thresholds, floor plate at high and motor neurons at lower concentrations (Roelink et al. (1995) supra; Mart' et al. (1995) supra; Tanabe, Y. et al. (1995) Curr. Biol. 5:651-658). Moreover, antibody blocking suggests that Shh produced by the notochord is required for notochord-mediated induction of motor neuron fates (Mart' et al. (1995) supra). Thus, high concentration of Shh on the surface of Shh-producing midline cells appears to account for the contact-mediated induction of floorplate observed in vitro (Placzek, M. et al. (1993) Development 117:205-218), and the midline positioning of the Doorplate immediately above the notochord in vivo. Lower concentrations of Shh released from the notochord and the floorplate presumably induce motor neurons at more distant ventrolateral regions in a process that has been shown to be contact-independent in vitro (Yamada, T. et al. (1993) Cell 73:673-686). In explants taken at midbrain and forebrain levels, Shh also induces the appropriate ventrolateral neuronal cell types, dopaminergic (Heynes, M. et al. (1995) Neuron 15:3544; Wang, M. Z. et al. (1995) Nature Med. 1:1184-1188) and cholinergic (Ericson, J. et al. (1995) Cell 81:747-756) precursors, respectively, indicating that Shh is a common inducer of ventral specification over the entire length of the CNS. These observations raise a question as to how the differential response to Shh is regulated at particular anteroposterior positions.

Shh from the midline also patterns the paraxial regions of the vertebrate embryo, the somites in the trunk (Fan et al. (1995) supra) and the head mesenchyme rostral of the somites (Hammerschmidt et al. (1996) supra). In chick and mouse paraxial mesoderm explants, Shh promotes the expression of sclerotome specific markers like Pax1 and Twist, at the expense of the dermamyotomal marker Pax3. Moreover, filter barrier experiments suggest that Shh mediates the induction of the sclerotome directly rather than by activation of a secondary signaling mechanism (Fan, C.-M. and Tessier-Lavigne, M. (1994) Cell 79, 1175-1186).

Shh also induces myotomal gene expression (Hammerschmidt et al. (1996) supra; Johnson, R. L. et al. (1994) Cell 79:1165-1173; Münsterberg, A. E. et al. (1995) Genes Dev. 9:2911-2922; Weinberg, E. S. et al. (1996) Development 122:271-280), although recent experiments indicate that members of the WNT family, vertebrate homologues of Drosophila wingless, are required in concert (Münsterberg et al. (1995) supra). Puzzlingly, myotomal induction in chicks requires higher Shh concentrations than the induction of sclerotomal markers (Münsterberg et al. (1995) supra), although the sclerotome originates from somitic cells positioned much closer to the notochord. Similar results were obtained in the zebrafish, where high concentrations of Hedgehog induce myotomal and repress sclerotomal marker gene expression (Hammerschmidt et al. (1996) supra). In contrast to amniotes, however, these observations are consistent with the architecture of the fish embryo, as here, the myotome is the predominant and more axial component of the somites. Thus, modulation of Shh signaling and the acquisition of new signaling factors may have modified the somite structure during vertebrate evolution.

In the vertebrate limb buds, a subset of posterior mesenchymal cells, the "Zone of polarizing activity" (ZPA), regulates anteroposterior digit identity (reviewed in Honig, L. S. (1981) Nature 291:72-73). Ectopic expression of Shh or application of beads soaked in Shh peptide mimics the effect of anterior ZPA grafts, generating a mirror image duplication of digits (Chang et al. (1994) supra; Lopez-Martinez et al. (1995) supra; Riddle et al. (1993) supra) (FIG. 2g). Thus, digit identity appears to depend primarily on Shh concentration, although it is possible that other signals may relay this information over the substantial distances that appear to be required for AP patterning (100-150 µm). Similar to the interaction of HH and DPP in the Drosophila imaginal discs, Shh in the vertebrate limb bud activates the expression of Bmp2 (Francis, P. H. et al. (1994) Development 120:209-218), a dpp homologue. However, unlike DPP in Drosophila, Bmp2 fails to mimic the polarizing effect of Shh upon ectopic application in the chick limb bud (Francis et al. (1994) supra). In addition to anteroposterior patterning, Shh also appears to be involved in the regulation of the proximodistal outgrowth of the limbs by inducing the synthesis of the fibroblast growth factor FGF4 in the posterior apical ectodermal ridge (Laufer, E. et al. (1994) Cell 79:993-1003; Niswander, L. et al. (1994) Nature 371:609-612).

The close relationship between Hedgehog proteins and BMPs is likely to have been conserved at many, but probably not all sites of vertebrate Hedgehog expression. For example, in the chick hindgut, Shh has been shown to induce the expression of Bmp4, another vertebrate dpp homologue (Roberts, D. J. et al. (1995) Development 121:3163-3174). Furthermore, Shh and Bmp2, 4, or 6 show a striking correlation in their expression in epithelial and mesenchymal cells of the stomach, the urogenital system, the lung, the tooth buds and the hair follicles (Bitgood, M. J. and McMahon, A. P. (1995) Dev. Biol. 172:126-138). Further, Ihh, one of the two other mouse Hedgehog genes, is expressed adjacent to Bmp expressing cells in the gut and developing cartilage (Bitgood and McMahon (1995) supra).

Recent evidence suggests a model in which Ihh plays a crucial role in the regulation of chondrogenic development (Roberts et al. (1995) supra). During cartilage formation, chondrocytes proceed from a proliferating state via an intermediate, prehypertrophic state to differentiated hypertrophic chondrocytes. Ihh is expressed in the prehypertrophic chondrocytes and initiates a signaling cascade that leads to the blockage of chondrocyte differentiation. Its direct target is the perichondrium around the Ihh expression domain, which responds by the expression of Gli and Patched (Ptc), conserved transcriptional targets of Hedgehog signals (see below). Most likely, this leads to secondary signaling resulting in the synthesis of parathyroid hormone-related protein (PTHrP) in the periarticular perichondrium. PTHrP itself signals back to the prehypertrophic chondrocytes, blocking their further differentiation. At the same time, PTHrP represses expression of Ihh, thereby forming a negative feedback loop that modulates the rate of chondrocyte differentiation.

Patched was originally identified in Drosophila as a segment polarity gene, one of a group of developmental genes that affect cell differentiation within the individual segments that occur in a homologous series along the anterior-posterior axis of the embryo. See Hooper, J. E. et al. (1989) Cell 59:751; and Nakano, Y. et al. (1989) Nature 341:508. Patterns of expression of the vertebrate homologue of patched suggest its involvement in the development of neural tube, skeleton, limbs, craniofacial structure, and skin.

Genetic and functional studies demonstrate that patched is part of the hedgehog signaling cascade, an evolutionarily conserved pathway that regulates expression of a number of downstream genes. See Perrimon, N. (1995) Cell 80:517; and Perrimon, N. (1996) Cell 86:513. Patched participates in the constitutive transcriptional repression of the target genes; its effect is opposed by a secreted glycoprotein, encoded by hedgehog, or a vertebrate homologue, which induces transcriptional activation. Genes under control of this pathway include members of the Wnt and TGF-beta families.

Patched proteins possess two large extracellular domains, twelve transmembrane segments, and several cytoplasmic segments. See Hooper, spra; Nakano, supra; Johnson, R. L. et al. (1996) Science 272:1668; and Hahn, H. et al. (1996) Cell 85:841. The biochemical role of patched in the hedgehog signaling pathway is unclear. Direct interaction with the hedgehog protein has, however, been reported (Chen, Y. et al. (1996) Cell 87:553), and patched may participate in a hedgehog receptor complex along with another transmembrane protein encoded by the smoothened gene. See Perrimon, supra; and Chen, supra.

The human homologue of patched was recently cloned and mapped to chromosome 9q22.3. See Johnson, supra; and Hahn, supra. This region has been implicated in basal cell nevus syndrome (BCNS), which is characterized by developmental abnormalities including rib and craniofacial alterations, abnormalities of the hands and feet, and spina bifida.

BCNS also predisposes to multiple tumor types, the most frequent being basal cell carcinomas (BCC) that occur in many locations on the body and appear within the first two decades of life. Most cases of BCC, however, are unrelated to the syndrome and arise sporadically in small numbers on sun-exposed sites of middle-aged or older people of northern European ancestry.

Recent studies in BCNS-related and sporadic BCC suggest that a functional loss of both alleles of patched leads to development of BCC. See Johnson, supra; Hahn, supra; and Gailani, M. R. et al. (1996) Nature Genetics 14:78. Single allele deletions of chromosome 9q22.3 occur frequently in both sporadic and hereditary BCC. Linkage analysis revealed that the defective inherited allele was retained and the normal allele was lost in tumors from BCNS patients.

Sporadic tumors also demonstrated a loss of both functional alleles of patched. Of twelve tumors in which patched mutations were identified with a single strand conformational polymorphism screening assay, nine had chromosomal deletion of the second allele and the other three had inactivating mutations in both alleles (Gailani, supra). The alterations did not occur in the corresponding germline DNA.

Most of the identified mutations resulted in premature stop codons or frame shifts. Lench, N. J., et al., Hum. Genet. 1997 October; 100(5-6): 497-502. Several, however, were point mutations leading to amino acid substitutions in either extracellular or cytoplasmic domains. These sites of mutation may indicate functional importance for interaction with extracellular proteins or with cytoplasmic members of the downstream signaling pathway.

The involvement of patched in the inhibition of gene expression and the occurrence of frequent allelic deletions of patched in BCC support a tumor suppressor function for this gene. Its role in the regulation of gene families known to be involved in cell signaling and intercellular communication provides a possible mechanism of tumor suppression.

SUMMARY OF THE INVENTION

One aspect of the present invention makes available methods and reagents for inhibiting smoothened-dependent pathway activation. In certain embodiments, the subject methods can be used to counteract the phenotypic effects of unwanted activation of a hedgehog pathway, such as resulting from hedgehog gain-of-function, ptc loss-of-function or smoothened gain-of-function mutations. For instance, the subject method can involve contacting a cell (in vitro or in vivo) with a hedgehog antagonist (defined infra), such as a steroidal alkaloid or other small molecule in an amount sufficient to antagonize a smoothened-dependent pathway activation pathway.

Another aspect of the present invention makes available methods and reagents for activating smoothened-dependent pathway activation, e.g, to mimic all or certain of the effects that treatment with a hedgehog protein might cause. The subject method can involve contacting a cell (in vitro or in vivo) with a smoothened agonist (defined infra) in an amount sufficient to activate a smoothened-dependent pathway activation pathway.

The subject methods and compounds may be used to regulate proliferation and/or differentiation of cells in vitro and/or in vivo, e.g., in the formation of tissue from stem cells, or to prevent the growth of hyperproliferative cells to illustrate but a few uses.

The subject compounds may be formulated as a pharmaceutical preparation comprising a pharmaceutically acceptable excipient. Hedgehog antagonists of the invention and/or preparations comprising them may be administered to a patient to treat conditions involving unwanted cell proliferation, e.g., cancer and/or tumors (such as medullablastoma, basal cell carcinoma, etc.), non-malignant hyperproliferative disorders, etc. Smoothened agonists can also be used to regulate the growth and differentiation of normal tissues. In certain embodiments, such compounds or preparations are administered systemically and/or locally, e.g., topically.

BRIEF DESCRIPTION OF THE DRAWINGS

FIG. 3. Synthetic and plant derived teratogens block endogenous Shh signaling in explanted chick tissues (41). (A) Midline tissue was removed from stage 9-10 chick embryos at a level just rostral to Hensen's node (white dashed line), and further dissected (black dashed lines) to yield an explant containing an endogenous source of Shh signal (notochord) and a responsive tissue (neural plate ectoderm). After two days of culture in a collagen gel matrix, the neural ectoderm expresses markers of floor plate cells (HNF3β, rhodamine) and motor neurons (Isl-1, FITC) in untreated control explants (B) and explants cultured with the non-teratogenic alkaloid tomatidine (50 μM, C). Intermedia doses of the teratogenic compounds AY 9944 (0.5 μM, D), triparanol (0.25 μM, E), jervine (0.5 μM, F) and cyclopamine (0.25 μM, G) block induction of HNF3β, which requires a high level of Shh pathway activation, while permitting induction of Isl-1, which requires a lower level of Shh pathway activation (see text). Higher doses of the teratogenic compounds AY 9944 (4.0 μM, H), triparanol (1.0 μM, I), jervine (4.0 μM, J) and cyclopamine (1.0 μM, K) and fully inhibit HNF3β and Isl-1 induction.

Figure 1:
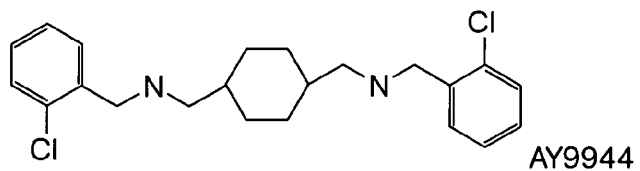
FIG. 1. Structures of the synthetic compounds AY 9944 and triparanol, of the plant steriodal alkaloids jervine, cyclopamine and tomatidine, and of cholesterol.
Figure 1:
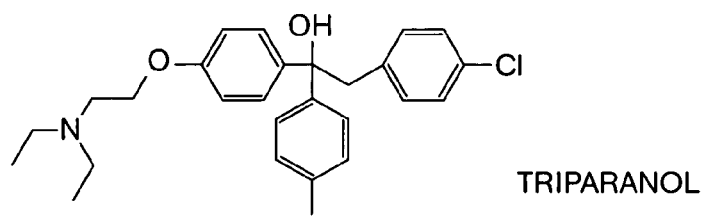
Figure 1:
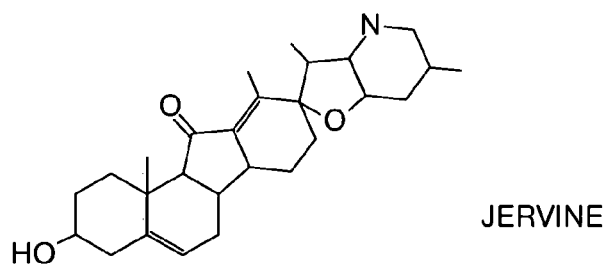
Figure 1:
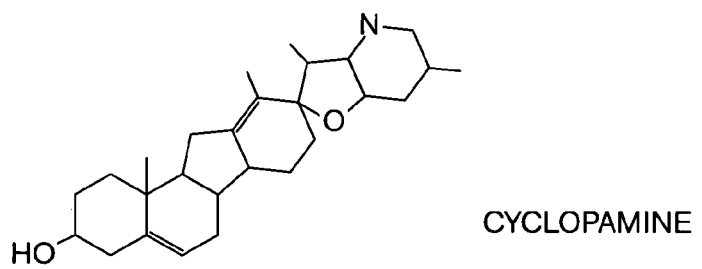
Figure 1:
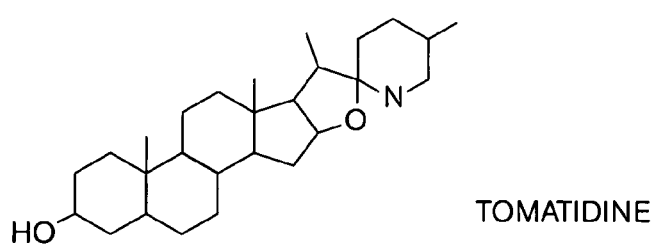
Figure 1:
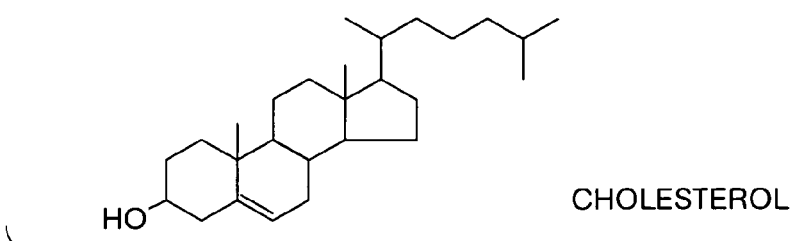

(D) Induction of migratory HNK-1 positive cells by 100 ng/ml BMP7 is not inhibited by the presence of 10 µM jervine, nor by addition of the other plant-derived compounds (10 µM cyclopamine, 50 µM tomatidine; data not shown).

FIG. 8. Morphology and gene expression patterns of control and Shh –/– primary hair germs. (A,B) Normal-appearing hair genus consisting of an epithelial placode and adjacent mesenchymal condensate (arrows) were detected in skin of both control (A) and Shh –/– (B) embryos at 15.5 days of gestation (H&E staining). (C-H) Altered abundance of Shh target genes in hair germs in Shh –/– mouse skin. Expression of Gli1 (C,D), Ptc1. (E,F), and BMP-4 (G,H) transcripts was examined in E 15.5 mouse skin using digoxigenin-labeled cRNA probes. Note virtual absence of Gli1 in both epithelial and mesenchymal components of the mutant hair germ and reduced mesenchymal Ptc1 expression in Shh –/– skin.

FIG. 9. Inhibition of hair follicle morphogenesis, but not biochemical differentiation, in Shh –/– mouse skin. (A,B) Advanced hair follicle development in skin from control (A) but not Shh –/– (B) embryos at 17.5 days of gestation (H&E staining).

Note dermal papilla (arrow) surrounded by epithelial bulb of the largest hair follicle, and organizing mesenchymal aggregates (arrowheads) adjacent to invaginating tips of less mature follicles (A). In striking contrast, dermal papillae are not detected in Shh mutant skin (B). (C-F) Immunohistochemistry revealing similar patterns of keratin expression in control and Shh-deficient follicles. Absence of keratin K 14 immunostaining in subpopulation of keratinocytes in both control (C) and Shh –/– (D) hair follicles (arrows). Induction of non-epidermal. keratin K17 in hair follicle keratinocytes in control (E) and Shh mutant (F) skin.

FIG. 10. Impaired hair follicle development in Shh mutant skin grafted onto nude mice. (A) Gross appearance of nude mouse graft sites 6 weeks after transplantation.

Note robust hair growth in control graft compared to hairless, but pigmented, Shh –/– skin graft. (B,C)H&E staining. Histologically normal-appearing skin in control graft (B) contains mature hair follicles with associated sebaceous glands and subcutaneous adipose tissue. Abnormal skin development in Shh –/– graft characterized by a thickened epidermis containing keratinocyte aggregates (arrows) at the base of the epidermis (C). (D-F) Immunohistochemistry. Unlike adjacent epidermal cells, Shh –/– keratinocyte aggregates do not express K5 (D, arrows) but are positive for Lef-1 localized to nuclei (E). Note also the presence of a small cluster of Lef-1 positive mesenchyrnal cells associated with the keratinocyte aggregate on the right (E). Immunostaining of abortive hair shafts with hair-specific keratin antibody AE 13 (F), revealing an advanced stage of follicle differentiation in Shh mutant skin.

FIG. 11. Cyclopamine impairs vibrissa follicle morphogenesis in explant cultures. (A) vibrissa pad explants growing on Nuclepore membranes on day one and day eight in culture (dark-field). (B) FC-PCR analysis examining expression of transcripts encoding hair-specific markers MHKAI and Hacl-1, and an epidermal differentiation marker filaggrin (profio. RNA was obtained from embryonic vibrissa pads when first isolated (Day 0) and after growth as explants (Day 7) in the presence or absence of I~M cyclopamine. Each lane contains reaction products for RNA isolated from an individual vibrissa pad. C) Morphogenesis of vibrissa follicles is blocked by cyclopamine, an inhibitor of Shh signaling. Cyclopamine was present in the medium for the duration of the experiment.

Figure 12:
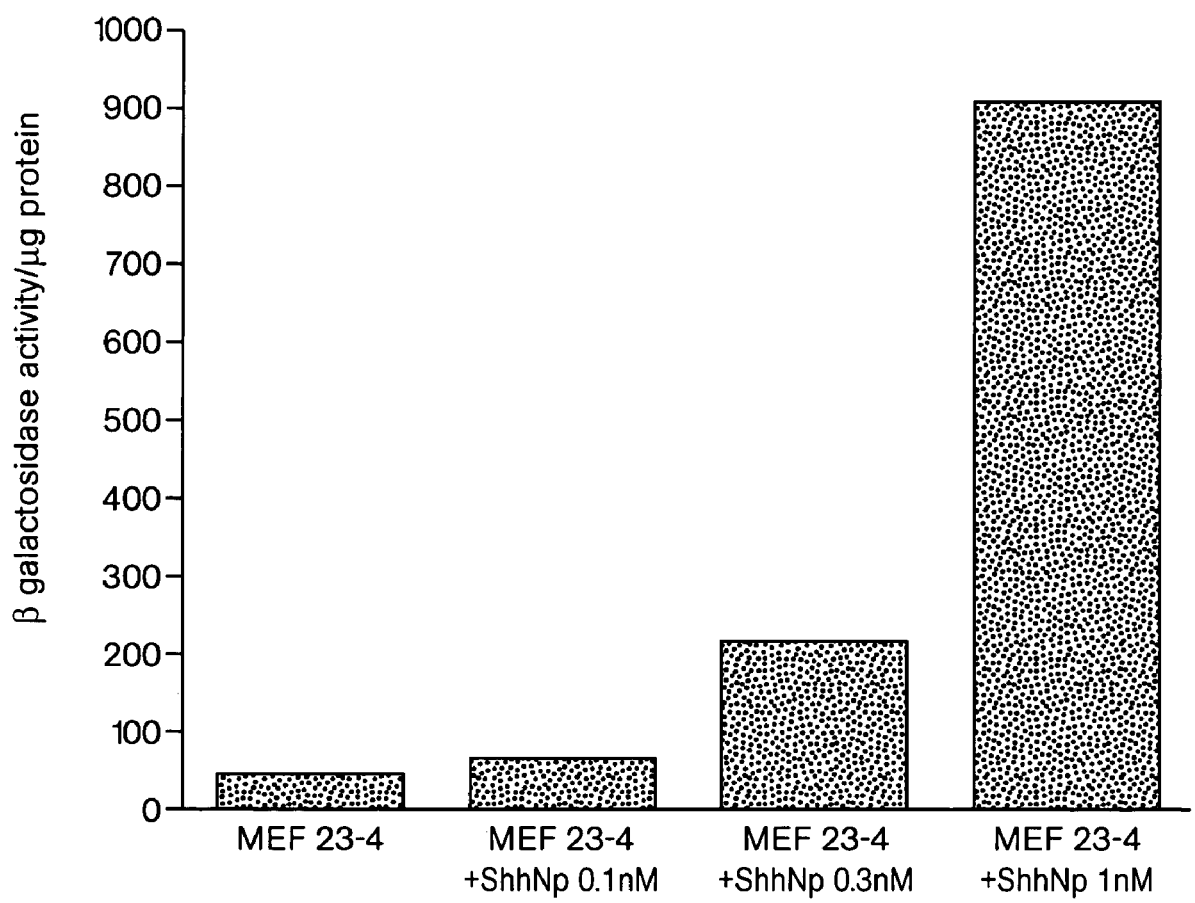

FIG. 12. Ptc +/–MEFs incubated with ShhNp for 5 days.

Figure 13:
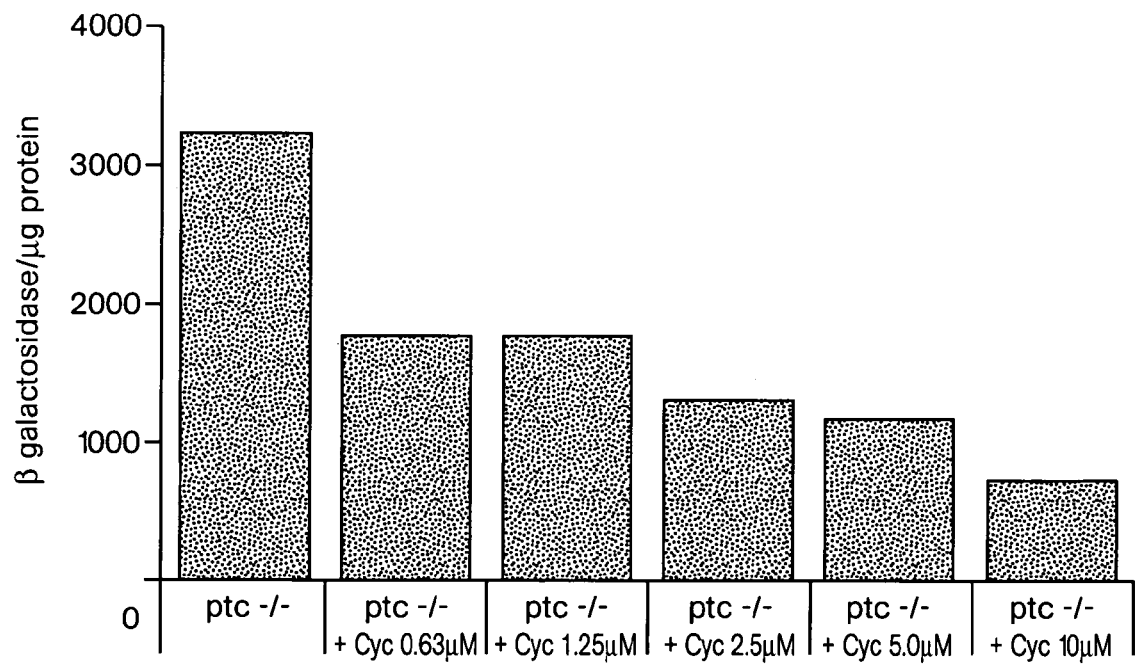

FIG. 13. Ptc +/– MEFs 23-1 cultured with cyclopamine for 3 days.

Figure 14:
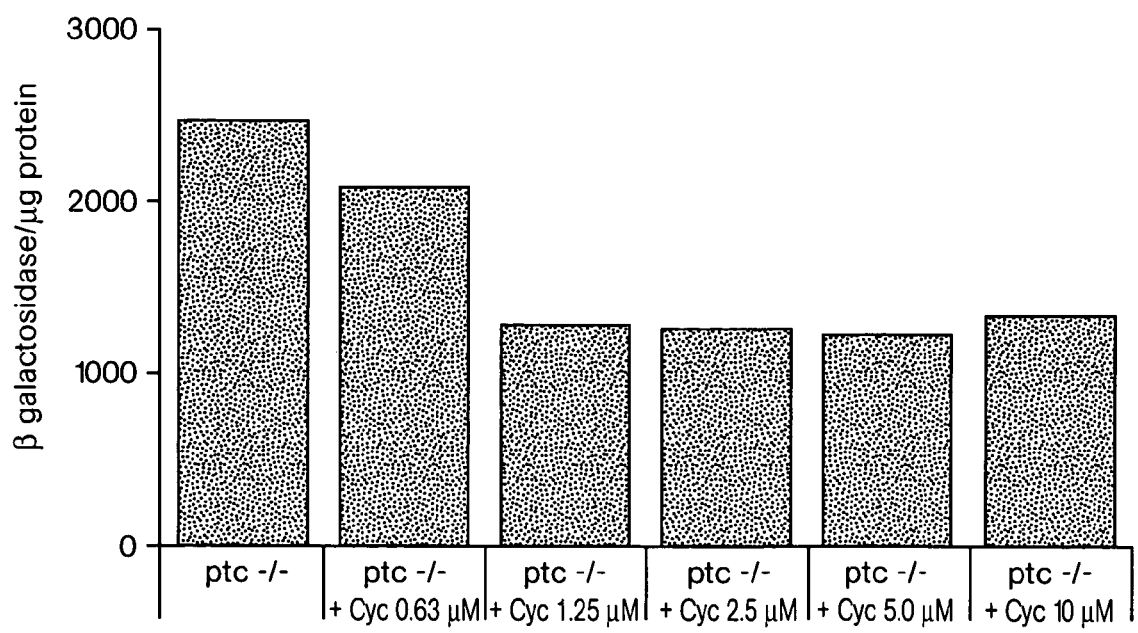

FIG. 14. Ptc –/– MEFs 234 cultured with cyclopamine for 16 hours.

Figure 15:
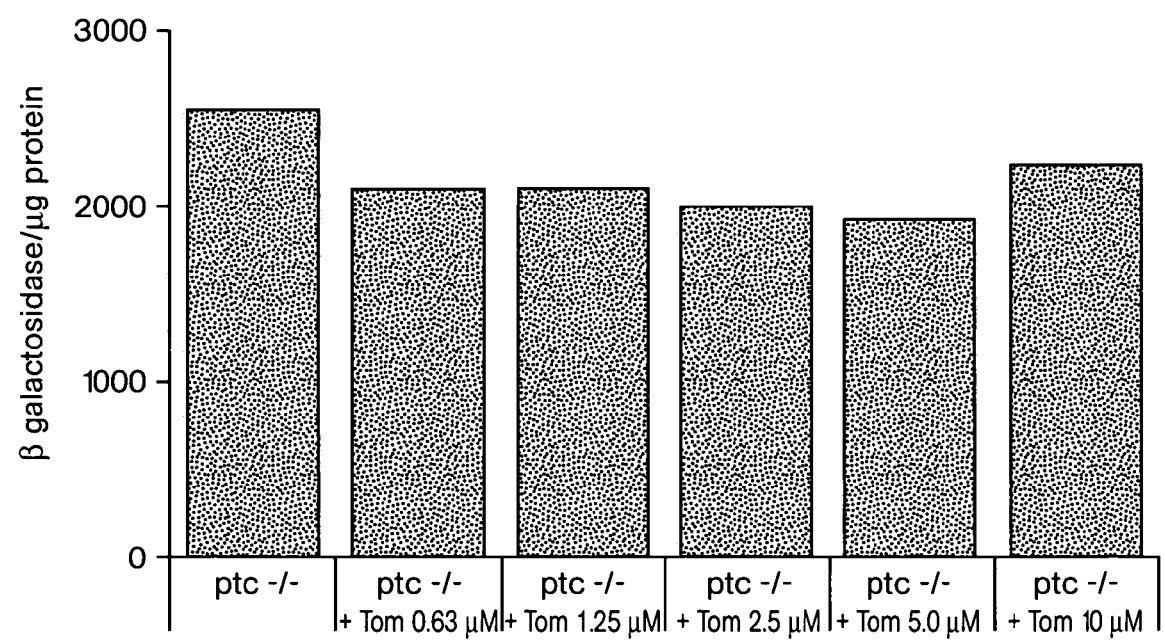

FIG. 15. Ptc –/– MEFs 214 cultured with tomatidine for 16 hours.

DETAILED DESCRIPTION OF THE INVENTION

I Overview

The present invention relates to the discovery that signal transduction pathways regulated by hedgehog, patched (ptc), gli and/or smoothened can be inhibited, at least in part, by small molecules. While not wishing to bound by any particular theory, the activation of a receptor may be the mechanism by which these agents act. For example, the ability of these agents to inhibit proliferation of patched loss-of-function ($ptc^{lof}$) cells may be due to the ability of such molecules to interact with hedgehog, patched, or smoothened, or at least to interfere with the ability of those proteins to activate a hedgehog, ptc, and/or smoothened-mediated signal transduction pathway.

It is, therefore, specifically contemplated that these small molecules which intefere with aspects of hedgehog, ptc, or smoothened signal transduction activity will likewise be capable of inhibiting proliferation (or other biological consequences) in cells having a patched loss-of-function phenotype, a hedgehog gain-of-function phenotype, or a smoothened gain-of-function phenotype. In preferred embodiments, the subject inhibitors are organic molecules having a molecular weight less than 2500 amu, more preferably less than 1500 amu, and even more preferably less than 750 amu, and are capable of inhibiting at least some of the biological activities of hedgehog proteins, preferably specifically in target cells.

Thus, the methods of the present invention include the use of small molecules which agonize ptc inhibition of hedgehog signalling, such as by inhibiting activation of smoothened or downstream components of the signal pathway, in the regulation of repair and/or functional performance of a wide range of cells, tissues and organs having the phenotype of ptc loss-of-function, hedgehog gain-of-function, or smoothened gain-of-function. For instance, the subject method has therapeutic and cosmetic applications ranging from regulation of neural tissues, bone and cartilage formation and repair, regulation of spermatogenesis, regulation of smooth muscle, regulation of lung, liver and other organs arising from the primative gut, regulation of hematopoietic function, regulation of skin and hair growth, etc. Moreover, the subject methods can be performed on cells which are provided in culture (in vitro), or on cells in a whole animal (in vivo). See, for example, PCT publications WO 95/18856 and WO 96/17924 (the specifications of which are expressly incorporated by reference herein).

In a preferred embodiment, the subject method can be to treat epithelial cells having a phenotype of ptc loss-of-function, hedgehog gain-of-function, or smoothened gain-of-function. For instance, the subject method can be used in treating or preventing basal cell carcinoma or other hedgehog pathway-related disorders.

In another preferred embodiment, the subject method can be used as part of a treatment regimen for malignant medulloblastoma and other primary CNS malignant neuroectodermal tumors.

In another aspect, the present invention provides pharmaceutical preparations comprising, as an active ingredient, a hedgehog antagonist, ptc agonist, or smoothened antagonist such as described herein, formulated in an amount sufficient to inhibit, in vivo, proliferation or other biological consequences of ptc loss-of-function, hedgehog gain-of-function, or smoothened gain-of-function.

The subject treatments using hedgehog antagonists, patched agonists, or smoothened antagonists can be effective for both human and animal subjects. Animal subjects to which the invention is applicable extend to both domestic animals and livestock, raised either as pets or for commercial purposes. Examples are dogs, cats, cattle, horses, sheep, hogs, and goats.

II Definitions

For convience, certain terms employed in the specification, examples, and appended claims are collected here.

The phrase "aberrant modification or mutation" of a gene refers to such genetic lesions as, for example, deletions, substitution or addition of nucleotides to a gene, as well as gross chromosomal rearrangements of the gene and/or abnormal methylation of the gene. Likewise, mis-expression of a gene refers to aberrant levels of transcription of the gene relative to those levels in a normal cell under similar conditions, as well as non-wild-type splicing of mRNA transcribed from the gene.

"Basal cell carcinomas" exist in a variety of clinical and histological forms such as nodular-ulcerative, superficial, pigmented, morphealike, fibroepithelioma and nevoid syndrome. Basal cell carcinomas are the most common cutaneous neoplasms found in humans. The majority of new cases of nonmelanoma skin cancers fall into this category.

"Burn wounds" refer to cases where large surface areas of skin have been removed or lost from an individual due to heat and/or chemical agents.

The term "carcinoma" refers to a malignant new growth made up of epithelial cells tending to infiltrate surrounding tissues and to give rise to metastases. Exemplary carcinomas include: "basal cell carcinoma", which, is an epithelial tumor of the skin that, while seldom metastasizing, has potentialities for local invasion and destruction; "squamous cell carcinoma", which refers to carcinomas arising from squamous epithelium and having cuboid cells; "carcinosarcoma", which include malignant tumors composed of carcinomatous and sarcomatous tissues; "adenocystic carcinoma", carcinoma marked by cylinders or bands of hyaline or mucinous stroma separated or surrounded by nests or cords of small epithelial cells, occurring in the mammary and salivary glands, and mucous glands of the respiratory tract; "epidermoid carcinoma", which refers to cancerous cells which tend to differentiate in the same way as those of the epidermis; i.e., they tend to form prickle cells and undergo cornification; "nasopharyngeal carcinoma", which refers to a malignant tumor arising in the epithelial lining of the space behind the nose; and "renal cell carcinoma", which pertains to carcinoma of the renal parenchyma composed of tubular cells in varying arrangements. Other carcinomatous epithelial growths are "papillomas", which refers to benign tumors derived from epithelium and having a papillomavirus as a causative agent; and "epidermoidomas", which refers to a cerebral or meningeal tumor formed by inclusion of ectodermal elements at the time of closure of the neural groove.

The "corium" or "dermis" refers to the layer of the skin deep to the epidermis, consisting of a dense bed of vascular connective tissue, and containing the nerves and terminal organs of sensation. The hair roots, and sebaceous and sweat glands are structures of the epidermis which are deeply embedded in the dermis.

"Dental tissue" refers to tissue in the mouth which is similar to epithelial tissue, for example gum tissue. The method of the present invention is useful for treating periodontal disease.

"Dermal skin ulcers" refer to lesions on the skin caused by superficial loss of tissue, usually with inflammation. Dermal skin ulcers which can be treated by the method of the present invention include decubitus ulcers, diabetic ulcers, venous stasis ulcers and arterial ulcers. Decubitus wounds refer to chronic ulcers that result from pressure applied to areas of the skin for extended periods of time. Wounds of this type are often called bedsores or pressure sores. Venous stasis ulcers result from the stagnation of blood or other fluids from defective veins. Arterial ulcers refer to necrotic skin in the area around arteries having poor blood flow.

The term "$ED_{50}$" means the dose of a drug which produces 50% of its maximum response or effect.

An "effective amount" of, e.g., a hedgehog antagonist, with respect to the subject method of treatment, refers to an amount of the antagonist in a preparation which, when applied as part of a desired dosage regimen brings about, e.g., a change in the rate of cell proliferation and/or the state of differentiation of a cell and/or rate of survival of a cell according to clinically acceptable standards for the disorder to be treated or the cosmetic purpose.

The terms "epithelia", "epithelial" and "epithelium" refer to the cellular covering of internal and external body surfaces (cutaneous, mucous and serous), including the glands and other structures derived therefrom, e.g., corneal, esophegeal, epideirmal, and hair follicle epithelial cells. Other exemplary epithlelial tissue includes: olfactory epithelium, which is the pseudostratified epithelium lining the olfactory region of the nasal cavity, and containing the receptors for the sense of smell; glandular epithelium, which refers to epithelium composed of secreting cells; squamous epithelium, which refers to epithelium composed of flattened plate-like cells. The term epithelium can also refer to transitional epithelium, like that which is characteristically found lining hollow organs that are subject to great mechanical change due to contraction and distention, e.g., tissue which represents a transition between stratified squamous and columnar epithelium.

The term "epithelialization" refers to healing by the growth of epithelial tissue over a denuded surface.

The term "epidermal gland" refers to an aggregation of cells associated with the epidermis and specialized to secrete or excrete materials not related to their ordinary metabolic needs. For example, "sebaceous glands" are holocrine glands in the corium that secrete an oily substance and sebum. The term "sweat glands" refers to glands that secrete sweat, situated in the corium or subcutaneous tissue, opening by a duct on the body surface.

The term "epidermis" refers to the outermost and nonvascular layer of the skin, derived from the embryonic ectoderm, varying in thickness from 0.07-1.4 mm. On the palmar and plantar surfaces it comprises, from within outward, five layers: basal layer composed of columnar cells arranged perpendicularly, prickle-cell or spinous layer composed of flattened polyhedral cells with short processes or spines; granular layer composed of flattened granular cells; clear layer composed of several layers of clear, transparent cells in which the nuclei are indistinct or absent; and horny layer composed of flattened, cornified non-nucleated cells. In the epidermis of the general body surface, the clear layer is usually absent.

"Excisional wounds" include tears, abrasions, cuts, punctures or lacerations in the epithelial layer of the skin and may extend into the dermal layer and even into subcutaneous fat and beyond. Excisional wounds can result from surgical procedures or from accidental penetration of the skin.

The "growth state" of a cell refers to the rate of proliferation of the cell and/or the state of differentiation of the cell. An "altered growth state" is a growth state characterized by an abnormal rate of proliferation, e.g., a cell exhibiting an increased or decreased rate of proliferation relative to a normal cell.

The term "hair" refers to a threadlike structure, especially the specialized epidermal structure composed of keratin and developing from a papilla sunk in the corium, produced only by mammals and characteristic of that group of animals. Also, "hair" may refer to the aggregate of such hairs. A "hair follicle" refers to one of the tubular-invaginations of the epidermis enclosing the hairs, and from which the hairs grow. "Hair follicle epithelial cells" refers to epithelial cells which surround the dermal papilla in the hair follicle, e.g., stem cells, outer root sheath cells, matrix cells, and inner root sheath cells. Such cells may be normal non-malignant cells, or transformed/immortalized cells.

The term "hedgehog antagonist" refers to an agent which potentiates or recapitulates the bioactivity of patched, such as to repress transcription of target genes. Preferred hedgehog antagonists can be used to overcome a ptc loss-of-function and/or a smoothened gain-of-function, the latter also being referred to as smoothened antagonists. The term 'hedgehog antagonist' as used herein refers not only to any agent that may act by directly inhibiting the normal function of the hedgehog protein, but also to any agent that inhibits the hedgehog signalling pathway, and thus recapitulates the function of ptc.

The term "hedgehog gain-of-function" refers to an aberrant modification or mutation of a ptc gene, hedgehog gene, or smoothened gene, or a decrease (or loss) in the level of expression of such a gene, which results in a phenotype which resembles contacting a cell with a hedgehog protein, e.g., aberrant activation of a hedgehog pathway. The gain-of-function may include a loss of the ability of the ptc gene product to regulate the level of expression of Ci genes, e.g., Gli1, Gli2, and Gli3. The term 'hedgehog gain-of-function' is also used herein to refer to any similar cellular phenotype (e.g., exhibiting excess proliferation) which occurs due to an alteration anywhere in the hedgehog signal transduction pathway, including, but not limited to, a modification or mutation of hedgehog itself For example, a tumor cell with an abnormally high proliferation rate due to activation of the hedgehog signalling pathway would have a 'hedgehog gain-of-function' phenotype, even if hedgehog is not mutated in that cell.

As used herein, "immortalized cells" refers to cells which have been altered via chemical and/or recombinant means such that the cells have the ability to grow through an indefinite number of divisions in culture.

"Internal epithelial tissue" refers to tissue inside the body which has characteristics similar to the epidermal layer in the skin. Examples include the lining of the intestine. The method of the present invention is useful for promoting the healing of certain internal wounds, for example wounds resulting from surgery.

The term "keratosis" refers to proliferative skin disorder characterized by hyperplasia of the horny layer of the epidermis. Exemplary keratotic disorders include keratosis follicularis, keratosis palmaris et plantaris, keratosis pharyngea, keratosis pilaris, and actinic keratosis.

The term "$LD_{50}$" means the dose of a drug which is lethal in 50% of test subjects.

The term "nail" refers to the horny cutaneous plate on the dorsal surface of the distal end of a finger or toe.

The term "patched loss-of-function" refers to an aberrant modification or mutation of a ptc gene, or a decreased level of expression of the gene, which results in a phenotype which resembles contacting a cell with a hedgehog protein, e.g., aberrant activation of a hedgehog pathway. The loss-of-function may include a loss of the ability of the ptc gene product to regulate the level of expression of Ci genes, e.g., Gli1, Gli2 and Gli3. The term 'ptc loss-of-function' is also used herein to refer to any similar cellular phenotype (e.g., exhibiting excess proliferation) which occurs due to an alteration anywhere in the hedgehog signal transduction pathway, including, but not limited to, a modification or mutation of ptc itself For example, a tumor cell with an abnormally high proliferation rate due to activation of the hedgehog signalling pathway would have a 'ptc loss-of-function' phenotype, even if ptc is not mutated in that cell.

A "patient" or "subject" to be treated by the subject method can mean either a human or non-human animal.

The term "prodrug" is intended to encompass compounds which, under physiological conditions, are converted into the therapeutically active agents of the present invention. A common method for making a prodrug is to include selected moieties which are hydrolyzed under physiological conditions to reveal the desired molecule. In other embodiments, the prodrug is converted by an enzymatic activity of the host animal.

As used herein, "proliferating" and "proliferation" refer to cells undergoing mitosis.

Throughout this application, the term "proliferative skin disorder" refers to any disease/disorder of the skin marked by unwanted or aberrant proliferation of cutaneous tissue. These conditions are typically characterized by epidermal cell proliferation or incomplete cell differentiation, and include, for example, X-linked ichthyosis, psoriasis, atopic dermatitis, allergic contact dermatitis, epidermolytic hyperkeratosis, and seborrheic dermatitis. For example, epidermodysplasia is a form of faulty development of the epidermis. Another example is "epidermolysis", which refers to a loosened state of the epidermis with formation of blebs and bullae either spontaneously or at the site of trauma.

As used herein, the term "psoriasis" refers to a hyperproliferative skin disorder which alters the skin's regulatory mechanisms. In particular, lesions are formed which involve primary and secondary alterations in epidermal proliferation, inflammatory responses of the skin, and an expression of regulatory molecules such as lymphokines and inflammatory factors. Psoriatic skin is morphologically characterized by an increased turnover of epidermal cells, thickened epidermis, abnormal keratinization, inflammatory cell infiltrates into the dermis layer and polymorphonuclear leukocyte infiltration into the epidermis layer resulting in an increase in the basal cell cycle. Additionally, hyperkeratotic and parakeratotic cells are present.

The term "skin" refers to the outer protective covering of the body, consisting of the corium and the epidermis, and is understood to include sweat and sebaceous glands, as well as hair follicle structures. Throughout the present application, the adjective "cutaneous" may be used, and should be understood to refer generally to attributes of the skin, as appropriate to the context in which they are used.

The term "smoothened gain-of-function" refers to an aberrant modification or mutation of a smo gene, or an increased level of expression of the gene, which results in a phenotype which resembles contacting a cell with a hedgehog protein, e.g., aberrant activation of a hedgehog pathway. While not wishing to be bound by any particular theory, it is noted that ptc may not signal directly into the cell, but rather interact with smoothened, another membrane-bound protein located downstream of ptc in hedgehog signaling (Marigo et al., (1996) Nature 384: 177-179). The gene smo is a segment-polarity gene required for the correct patterning of every segment in Drosophila (Alcedo et al., (1996) Cell 86: 221-232). Human homologs of smo have been identified. See, for example, Stone et al. (1996) Nature 384:129-134, and GenBank accession U84401. The smoothened gene encodes an integral membrane protein with characteristics of heterotrimeric G-protein-coupled receptors; i.e., 7-transmembrane regions. This protein shows homology to the Drosophila Frizzled (Fz) protein, a member of the wingless pathway. It was originally thought that smo encodes a receptor of the Hh signal. However, this suggestion was subsequently disproved, as evidence for ptc being the Hh receptor was obtained. Cells that express Smo fail to bind Hh, indicating that smo does not interact directly with Hh (Nusse, (1996) Nature 384: 119-120). Rather, the binding of Sonic hedgehog (SHH) to its receptor, PTCH, is thought to prevent normal inhibition by PTCH of smoothened (SMO), a seven-span transmembrane protein.

Recently, it has been reported that activating smoothened mutations occur in sporadic basal cell carcinoma, Xie et al. (1998) Nature 391: 90-2, and primitive neuroectodermal tumors of the central nervous system, Reifenberger et al. (1998) Cancer Res 58: 1798-803.

The term "therapeutic index" refers to the therapeutic index of a drug defined as $LD_{50}/ED_{50}$.

As used herein, "transformed cells" refers to cells which have spontaneously converted to a state of unrestrained growth, i.e., they have acquired the ability to grow through an indefinite number of divisions in culture. Transformed cells may be characterized by such terms as neoplastic, anaplastic and/or hyperplastic, with respect to their loss of growth control.

The term "acylamino" is art-recognized and refers to a moiety that can be represented by the general formula:

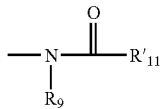

wherein $R_9$ is as defined above, and $R'_{11}$ represents a hydrogen, an alkyl, an alkenyl or —$(CH_2)_m$—$R_8$, where m and $R_8$ are as defined above.

Herein, the term "aliphatic group" refers to a straight-chain, branched-chain, or cyclic aliphatic hydrocarbon group and includes saturated and unsaturated aliphatic groups, such as an alkyl group, an alkenyl group, and an alkynyl group.

The terms "alkenyl" and "alkynyl" refer to unsaturated aliphatic groups analogous in length and possible substitution to the alkyls described above, but that contain at least one double or triple bond respectively.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_8$, where m and $R_8$ are described above.

The term "alkyl" refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 30 or fewer carbon atoms in its backbone (e.g., $C_1$-$C_{30}$ for straight chains, $C_3$-$C_{30}$ for branched chains), and more preferably 20 or fewer. Likewise, preferred cycloalkyls have from 3-10 carbon atoms in their ring structure, and more preferably have 5, 6 or 7 carbons in the ring structure.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m$—$R_8$, wherein m and $R_8$ are defined above. Representative alkylthio groups include methylthio, ethylthio, and the like.

The terms "amine" and "amino" are art-recognized and refer to both unsubstituted and substituted amines, e.g., a moiety that can be represented by the general formula:

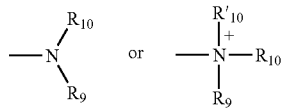

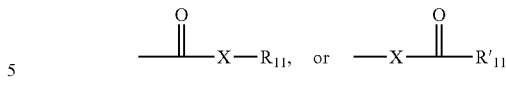

wherein $R_9$, $R_{10}$ and $R'_{10}$ each independently represent a hydrogen, an alkyl, an alkenyl, —$(CH_2)_m$—$R_8$, or $R_9$ and $R_{10}$ taken together with the N atom to which they are attached complete a heterocycle having from 4 to 8 atoms in the ring structure; $R_8$ represents an aryl, a cycloalkyl, a cycloalkenyl, a heterocycle or a polycycle; and m is zero or an integer in the range of 1 to 8. In preferred embodiments, only one of $R_9$ or $R_{10}$ can be a carbonyl, e.g., $R_9$, $R_{10}$ and the nitrogen together do not form an imide. In even more preferred embodiments, $R_9$ and $R_{10}$ (and optionally $R'_{10}$) each independently represent a hydrogen, an alkyl, an alkenyl, or —$(CH_2)_m$—$R_8$. Thus, the term "alkylamine" as used herein means an amine group, as defined above, having a substituted or unsubstituted alkyl attached thereto, i.e., at least one of $R_9$ and $R_{10}$ is an alkyl group.

The term "amido" is art-recognized as an amino-substituted carbonyl and includes a moiety that can be represented by the general formula:

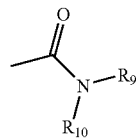

wherein $R_9$, $R_{10}$ are as defined above. Preferred embodiments of the amide will not include imides which may be unstable.

The term "aralkyl", as used herein, refers to an alkyl group substituted with an aryl group (e.g., an aromatic or heteroaromatic group).

The term "aryl" as used herein includes 5-, 6-, and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphate, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The term "carbocycle", as used herein, refers to an aromatic or non-aromatic ring in which each atom of the ring is carbon.

The term "carbonyl" is art-recognized and includes such moieties as can be represented by the general formula:

wherein X is a bond or represents an oxygen or a sulfur, and $R_{11}$ represents a hydrogen, an alkyl, an alkenyl, —$(CH_2)_m$—$R_8$ or a pharmaceutically acceptable salt, $R'_{11}$ represents a hydrogen, an alkyl, an alkenyl or —$(CH_2)_m$—$R_8$, where m and $R_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiocarbonyl" group. Where X is a sulfur and $R_{11}$ or $R'_{11}$ is not hydrogen, the formula represents a "thioester." Where X is a sulfur and $R_{11}$ is hydrogen, the formula represents a "thiocarboxylic acid." Where X is a sulfur and $R_{11}'$ is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

The term "heteroatom" as used herein means an atom of any element other than carbon or hydrogen. Preferred heteroatoms are boron, nitrogen, oxygen, phosphorus, sulfur and selenium.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —$SO_2$—.

A "phosphonamidite" can be represented in the general formula:

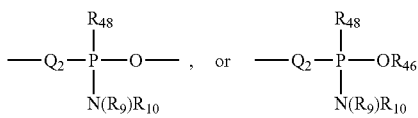

wherein $R_9$ and $R_{10}$ are as defined above, $Q_2$ represents O, S or N, and $R_{48}$ represents a lower alkyl or an aryl, $Q_2$ represents O, S or N.

A "phosphoramidite" can be represented in the general formula:

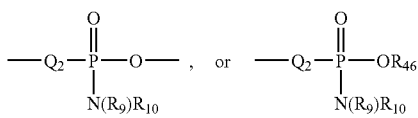

wherein $R_9$ and $R_{10}$ are as defined above, and $Q_2$ represents O, S or N.

A "phosphoryl" can in general be represented by the formula:

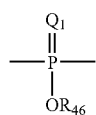

wherein $Q_1$ represented S or O, and $R_{46}$ represents hydrogen, a lower alkyl or an aryl. When used to substitute, for example, an alkyl, the phosphoryl group of the phosphorylalkyl can be represented by the general formula:

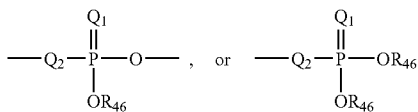

wherein $Q_1$ represented S or O, and each $R_{46}$ independently represents hydrogen, a lower alkyl or an aryl, $Q_2$ represents O, S or N. When $Q_1$ is an S, the phosphoryl moiety is a "phosphorothioate".

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M *Protective Groups in Organic Synthesis*, 2$^{nd}$ ed.; Wiley: New York, 1991).

A "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and —Se—(CH$_2$)$_m$—R$_8$, m and R$_8$ being defined above.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

The term "sulfamoyl" is art-recognized and includes a moiety that can be represented by the general formula:

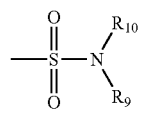

in which $R_9$ and $R_{10}$ are as defined above.

The term "sulfate" is art recognized and includes a moiety that can be represented by the general formula:

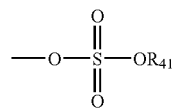

in which $R_{41}$ is as defined above.

The term "sulfonamido" is art recognized and includes a moiety that can be represented by the general formula:

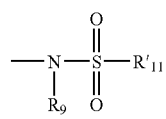

in which $R_9$ and $R'_{11}$ are as defined above.

The term "sulfonate" is art-recognized and includes a moiety that can be represented by the general formula:

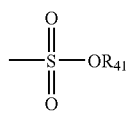

in which R$_{41}$ is an electron pair, hydrogen, alkyl, cycloalkyl, or aryl.

The terms "sulfoxido" or "sulfinyl", as used herein, refers to a moiety that can be represented by the general formula:

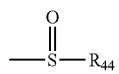

in which R$_{44}$ is selected from the group consisting of hydrogen, alkyl, alkenyl, alkynyl, cycloalkyl, heterocyclyl, aralkyl, or aryl.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g., alkyl, m, n, etc., when it occurs more than once in any structure, is intended to be independent of its definition elsewhere in the same structure.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

Certain compounds of the present invention may exist in particular geometric or stereoisomeric forms. The present invention contemplates all such compounds, including, cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts may be formed with an appropriate optically active acid or base, followed by resolution of the diastereomers thus formed by fractional crystallization or chromatographic means well known in the art, and subsequent recovery of the pure enantiomers.

Contemplated equivalents of the compounds described above include compounds which otherwise correspond thereto, and which have the same general properties thereof (e.g., the ability to inhibit hedgehog signaling), wherein one or more simple variations of substituents are made which do not adversely affect the efficacy of the compound. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

For purposes of this invention, the chemical elements are identified in accordance with the Periodic Table of the Elements, CAS version, Handbook of Chemistry and Physics, 67th Ed., 1986-87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

III. Exemplary Compounds of the Invention.

As described in further detail below, it is contemplated that the subject methods can be carried out using any of a variety of different steroidal alkaloids which can be readily identified, e.g., by such drug screening assays as described herein. Steroidal alkaloids have a fairly complex nitrogen-containing nucleus. Two exemplary classes of steroidal alkaloids for use in the subject methods are the *Solanum* type and the Veratrum type. The above notwithstanding, in a preferred embodiment, the methods and compositions of the present invention make use of compounds having a steroidal alkaloid ring system of cyclopamine.

There are more than 50 naturally occuring veratrum alkaloids including veratramine, cyclopamine, cycloposine, jervine, and muldamine occurring in plants of the *Veratrum* spp. The *Zigadenus* spp., death camas, also produces several veratrum-type of steroidal alkaloids including zygacine. In general, many of the veratrum alkaloids (e.g., jervine, cyclopamine and cycloposine) consist of a modified steroid skeleton attached spiro to a furanopiperidine. A typical veratrum-type alkaloid may be represented by:

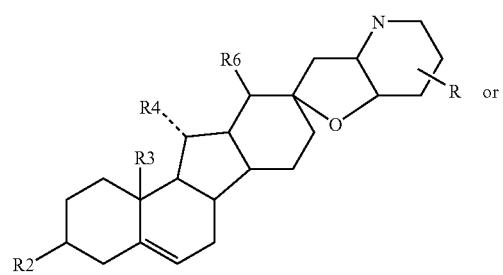

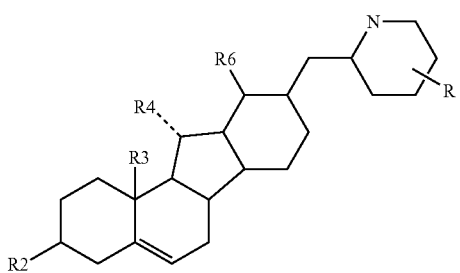

An example of the *Solanum* type is solanidine. This steroidal alkaloid is the nucleus (i.e., aglycone) for two important glycoalkaloids, solanine and chaconine, found in potatoes. Other plants in the *Solanum* family including various nightshades, Jerusalem cherries, and tomatoes also contain *solanum*-type glycoalkaloids. Glycoalkaloids are glycosides of alkaloids. A typical *solanum*-type alkaloid may be represented by:

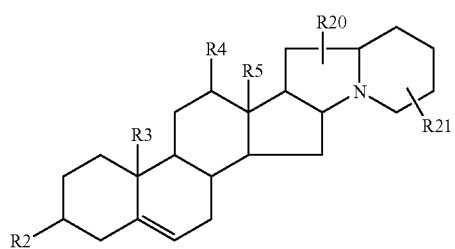

Based on these structures, and the possibility that certain unwanted side effects can be reduced by some manipulation of the structure, a wide range of steroidal alkaloids are contemplated as potential hedgehog antagonists for use in the subject method. For example, compounds useful in the subject methods include steroidal alkaloids represented in the general formulas (I), or unsaturated forms thereof and/or seco-, nor- or homo-derivatives thereof:

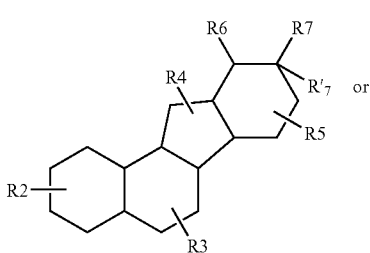

Formula I

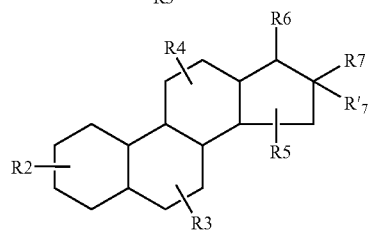

wherein, as valence and stability permit, $R_2$, $R_3$, $R_4$, and $R_5$, represent one or more substitutions to the ring to which each is attached, for each occurrence, independently represent hydrogen, halogens, alkyls, alkenyls, alkynyls, aryls, hydroxyl, =O, =S, alkoxyl, silyloxy, amino, nitro, thiol, amines, imines, amides, phosphoryls, phosphonates, phosphines, carbonyls, carboxyls, carboxamides, anhydrides, silyls, ethers, thioethers, alkylsulfonyls, arylsulfonyls, selenoethers, ketones, aldehydes, esters, sugar (e.g., monosaccharide, disaccharide, polysaccharide, etc.), carbamate (e.g., attached to the steroid at oxygen), carbonate, or —$(CH_2)_m$—$R_8$;

$R_6$, $R_7$, and $R'_7$, are absent or represent, independently, halogens, alkyls, alkenyls, alkynyls, aryls, hydroxyl, =O, =S, alkoxyl, silyloxy, amino, nitro, thiol, amines, imines, amides, phosphoryls, phosphonates, phosphines, carbonyls, carboxyls, carboxamides, anhydrides, silyls, ethers, thioethers, alkylsulfonyls, arylsulfonyls, selenoethers, ketones, aldehydes, esters, or —$(CH_2)_m$—$R_8$, or $R_6$ and $R_7$, or $R_7$ and $R'_7$, taken together form a ring or polycyclic ring, e.g., which is substituted or unsubstituted, with the proviso that at least one of $R_6$, $R_7$, or $R'_7$ is present and includes a primary or secondary amine;

$R_8$ represents an aryl, a cycloalkyl, a cycloalkenyl, a heterocycle, or a polycycle; and m is an integer in the range 0 to 8 inclusive.

In preferred embodiments, $R_2$ and $R_3$, for each occurrence, is an —OH, alkyl, —O-alkyl, —C(O)-alkyl, or —C(O)—$R_8$;

$R_4$, for each occurrence, is an absent, or represents —OH, =O, alkyl, —O-alkyl, —C(O)-alkyl, or —C(O)—$R_8$;

$R_6$, $R_7$, and $R'_7$ each independently represent, hydrogen, alkyls, alkenyls, alkynyls, amines, imines, amides, carbonyls, carboxyls, carboxamides, ethers, thioethers, esters, or —$(CH_2)_m$—$R_8$, or $R_7$, and $R'_7$ taken together form a furanopiperidine, such as perhydrofuro[3,2-b]pyridine, a pyranopiperidine, a quinoline, an indole, a pyranopyrrole, a naphthyridine, a thiofuranopiperidine, or a thiopyranopiperidine with the proviso that at least one of $R_6$, $R_7$, or $R'_7$ is present and includes a primary or secondary amine;

$R_8$ represents an aryl, a cycloalkyl, a cycloalkenyl, a heterocycle, or a polycycle, and preferably $R_8$ is a piperidine, pyrimidine, morpholine, thiomorpholine, pyridazine, In certain preferred embodiments, the definitions outlined above apply, and the subject compounds are represented by general formula Ia or unsaturated forms thereof and/or seco-, nor- or homo-derivatives thereof:

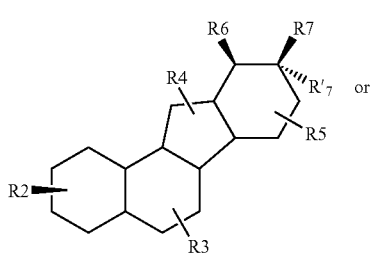

Formula Ia

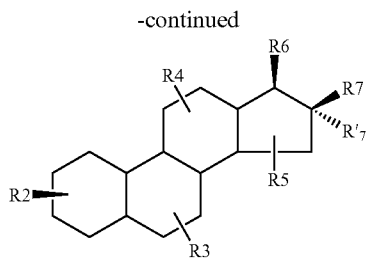

In preferred embodiments, the subject hedgehog antagonists can be represented in one of the following general formulas (II) or unsaturated forms thereof and/or seco-, nor-, or homo-derivatives thereof:

Formula II

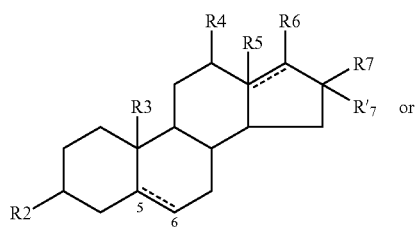

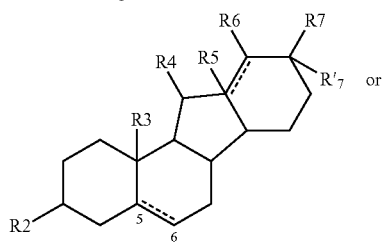

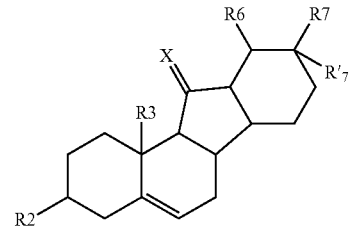

where $R_2$, $R_3$, $R_4$, $R_5$, $R_6$, $R_7$, and $R'_7$ are as defined above, and X represents O or S, though preferably O, and $R_5$ may also be absent.

In certain preferred embodiments, the definitions outlined above apply, and the subject compounds are represented by general formula IIa or unsaturated forms thereof and/or seco-, nor- or homo-derivatives thereof:

Formula IIa

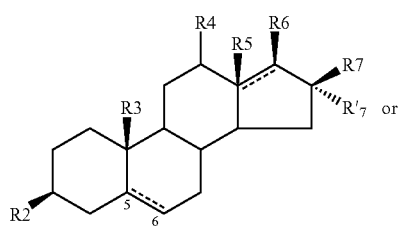

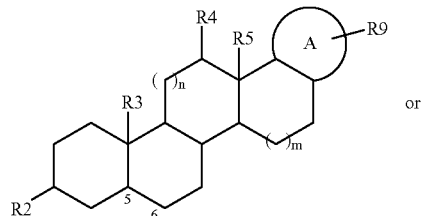

In certain embodiments, the subject hedgehog antagonists are represented by the general formula (III) or unsaturated forms thereof and/or seco-, nor- or homo-derivatives thereof:

Formula III

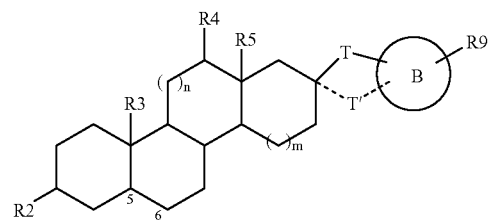

wherein
$R_2$, $R_3$, $R_4$, $R_5$ and $R_8$ are as defined above;
A and B represent monocyclic or polycyclic groups;
T represents an alkyl, an aminoalkyl, a carboxyl, an ester, an amide, ether or amine linkage of 1-10 bond lengths;
T' is absent, or represents an alkyl, an aminoalkyl, a carboxyl, an ester, an amide, ether or amine linkage of 1-3 bond lengths, wherein if T and T' are present together, than T and T' taken together with the ring A or B form a covalently closed ring of 5-8 ring atoms;
R9 represents one or more substitutions to the ring A or B, which for each occurrence, independently represent halogens, alkyls, alkenyls, alkynyls, aryls, hydroxyl, =O, =S, alkoxyl, silyloxy, amino, nitro, thiol, amines, imines, amides, phosphoryls, phosphonates, phosphines, carbonyls, carboxyls, carboxamides, anhydrides, silyls, ethers, thioethers, alkylsulfonyls, arylsulfonyls, selenoethers, ketones, aldehydes, esters, or —$(CH_2)_m$—$R_8$; and
n and m are, independently, zero, 1 or 2;
with the proviso that A and $R_9$, or T, T' B and $R_9$, taken together include at least one primary or secondary amine.

In certain preferred embodiments, the definitions outlined above apply, and the subject compounds are represented by general formula IIIa or unsaturated forms thereof and/or seco-, nor- or homo-derivatives thereof:

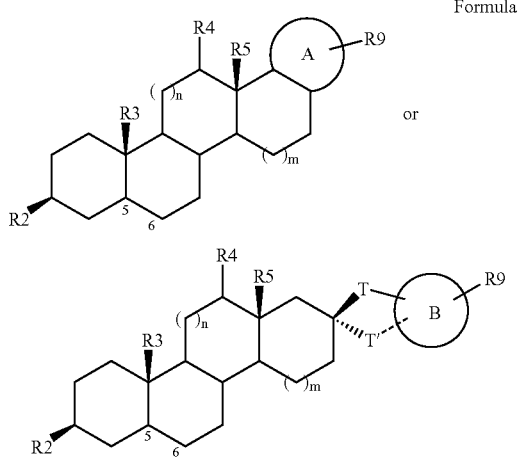

Formula IIIa

For example, the subject methods can utilize hedgehog antagonists based on the veratrum-type steroidal alkaloids jervine, cyclopamine, cycloposine, mukiamine or veratramine, e.g., which may be represented in the general formula (IV) or unsaturated forms thereof and/or seco-, nor- or homo-derivatives thereof:

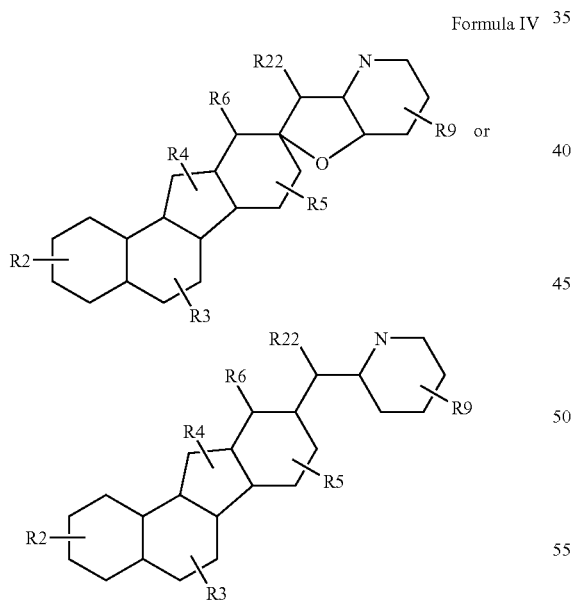

Formula IV wherein
$R_2$, $R_3$, $R_4$, $R_5$, $R_6$ and $R_9$ are as defined above;
$R_{22}$ is absent or represents an alkyl, an alkoxyl or —OH.

In certain preferred embodiments, the definitions outlined above apply, and the subject compounds are represented by general formula IVa or unsaturated forms thereof and/or seco-, nor- or homo-derivatives thereof:

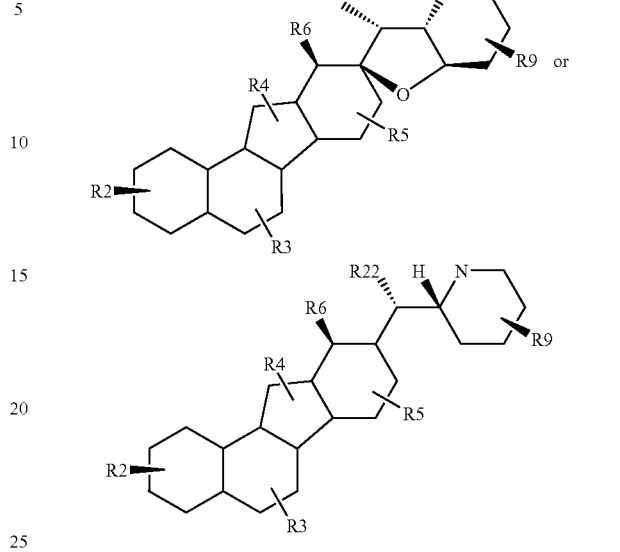

Formula IVa

In even more preferred embodiments, the subject antagonists are represented in the formulas (V) or unsaturated forms thereof and/or seco-, nor- or homo-derivatives thereof:

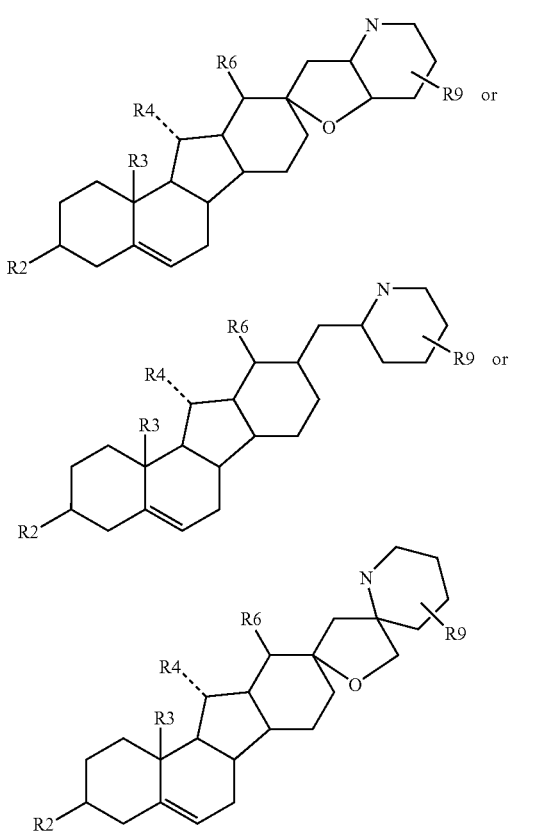

Formula V wherein $R_2$, $R_3$, $R_4$, $R_6$ and $R_9$ are as defined above;

In certain preferred embodiments, the definitions outlined above apply, and the subject compounds are represented by general formula Va or unsaturated forms thereof and/or seco-, nor- or homo-derivatives theref:

Formula Va

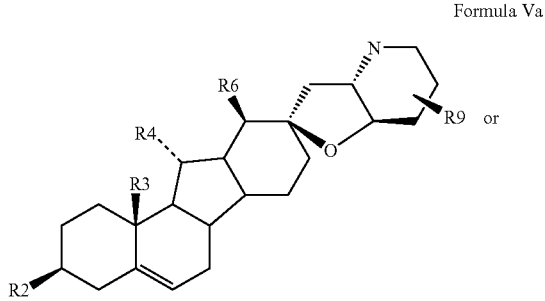

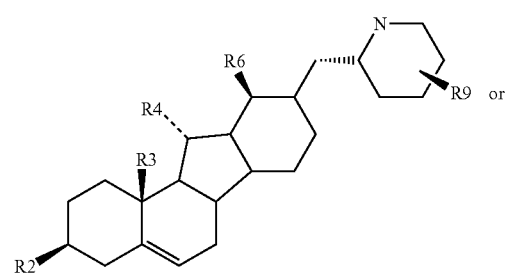

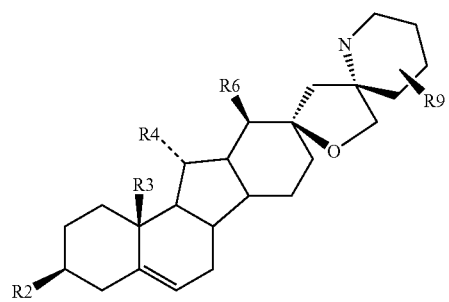

Another class of hedgehog antagonists can be based on the veratrum-type steroidal alkaloids resmebling verticine and zygacine, e.g., represented in the general formulas (VI) or unsaturated forms thereof and/or seco-, nor- or homo-derivatives thereof:

Formula VI

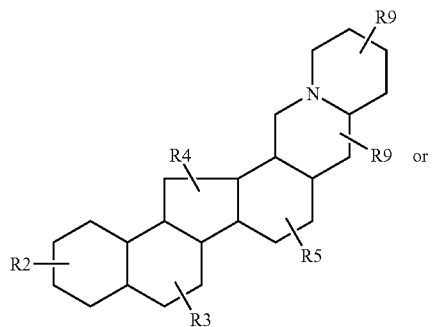

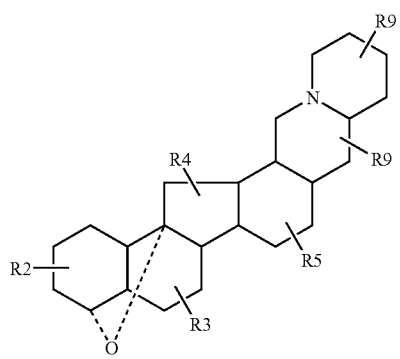

wherein $R_2$, $R_3$, $R_4$, $R_5$ and $R_9$ are as defined above.

In certain preferred embodiments, the definitions outlined above apply, and the subject compounds are represented by general formula VIa or unsaturated forms thereof and/or seco-, nor- or homo-derivatives thereof:

Formula VIa

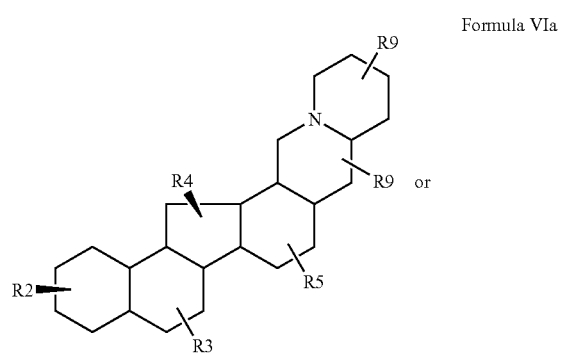

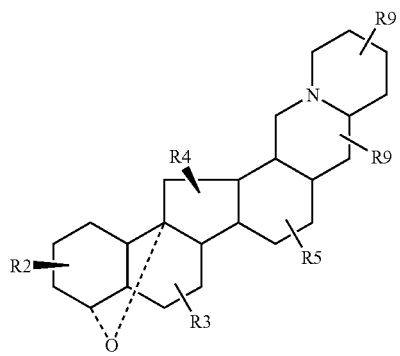

Still another class of potential hedgehog antagonists are based on the *solanum*-type steroidal alkaloids, e.g., solanidine, which may be represented in the general formula (VII) or unsaturated forms thereof and/or seco-, nor- or homo-derivatives thereof:

Formula VII

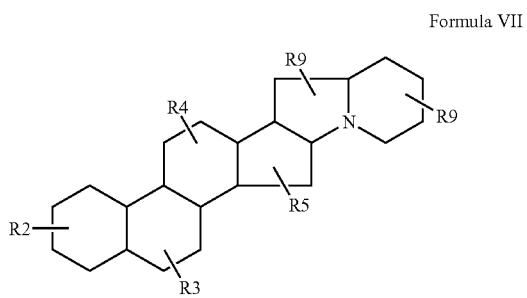

wherein $R_2$, $R_3$, $R_4$, $R_5$ and $R_9$ are as defined above.

In certain preferred embodiments, the definitions outlined above apply, and the subject compounds are represented by general formula VIIa or unsaturated forms thereof and/or seco-, nor- or homo-derivatives thereof:

Formula VIIa

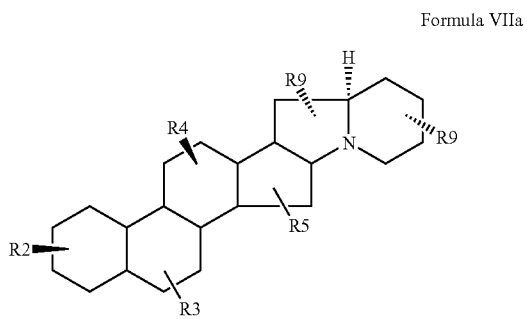

In certain embodiments, the subject antagonists can be chosen on the basis of their selectively for the hedgehog pathway. This selectivity can for the hedgehog pathway versus other steroid-mediated pathways (such as testosterone or estrogen mediated activities), as well as selectivity for particular hedgehog pathways, e.g., which isotype specific for hedgehog (e.g., Shh, Ihh, Dhh) or the patched receptor (e.g., ptc-1, ptc-2). For instance, the subject method may employ steroidal alkaloids which do not substantially interfere with the biological activity of such steroids as aldosterone, androstane, androstene, androstenedione, androsterone, cholecalciferol, cholestane, cholic acid, corticosterone, cortisol, cortisol acetate, cortisone, cortisone acetate, deoxycorticosterone, digitoxigenin, ergocalciferol, ergosterol, estradiol-17-α, estradiol-17-β, estriol, estrane, estrone, hydrocortisone, lanosterol, lithocholic acid, mestranol, β-methasone, prednisone, pregnane, pregnenolone, progesterone, spironolactone, testosterone, triamcinolone and their derivatives, at least so far as those activities are unrelated to ptc related signaling.

In one embodiment, the subject steroidal alkaloid for use in the present method has a $k_d$ for members of the nuclear hormone receptor superfamily of greater than 1 μM, and more preferably greater than 1 mM, e.g., it does not bind estrogen, testosterone receptors or the like. Preferably, the subject hedgehog antagonist has no estrogenic activity at physiological concentrations (e.g., in the range of 1 ng-1 mg/kg).

In this manner, untoward side effects which may be associated certain members of the steroidal alkaloid class can be reduced. For example, using the drug screening assays described herein, the application of combinatorial and medicinal chemistry techniques to the steroidal alkaloids provides a means for reducing such unwanted negative side effects including personality changes, shortened life spans, cardiovascular diseases and vascular occlusion, organ toxicity, hyperglycemia and diabetes, Cushnoid features, "wasting" syndrome, steroidal glaucoma, hypertension, peptic ulcers, and increased susceptibility to infections. For certain embodiments, it will be beneficial to reduce the teratogenic activity relative to jervine, as for example, in the use of the subject method to selectively inhibit spermatogenesis.

In a preferred embodiment, the subject antagonists are steroidal alkaloids other than spirosolane, tomatidine, jervine, etc.

In certain preferred embodiments, the subject inhibitors inhibit a hedgehog signal transduction pathway with an $ED_{50}$ of 1 mM or less, more preferably of 1 μM or less, and even more preferably of 1 nM or less.

In certain embodiments, the subject inhibitors inhibit a hedgehog signal transduction pathway with an $ED_{50}$ of 1 mM or less, more preferably 1 μM or less, and even more preferably 1 nM or less.

In particular embodiments, the steroidal alkaloid is chosen for use because it is more selective for one patched isoform over the next, e.g., 10-fold, and more preferably at least 100- or even 1000-fold more selective for one patched pathway (ptc-1, ptc-2) over another.

IV Exemplary Applications of Method and Compositions

Another aspect of the present invention relates to a method of modulating a differentiated state, survival, and/or proliferation of a cell, such as a normal cell or a cell having a ptc loss-of-function, hedgehog gain-of-function, or smoothened gain-of-function, by contacting the cells with a compound as set forth above according to the subject method and as the circumstances may warrant.

For instance, it is contemplated by the invention that, in light of the findings of an apparently broad involvement of hedgehog, ptc, and smoothened in the formation of ordered spatial arrangements of differentiated tissues in vertebrates, the subject method could be used as part of a process for generating and/or maintaining an array of different vertebrate tissue both in vitro and in vivo. The compound, whether inductive or anti-inductive with respect to proliferation or differentiation of a given tissue, can be, as appropriate, any of the preparations described above.

For example, the present method of using subject compounds is applicable to cell culture techniques wherein it is desirable to control the proliferation or differentiation of the cell. A subject compound may be employed in a method directed towards cells which have a ptc loss-of-function, hedgehog gain-of-function, or smoothened gain-of-function phenotype. In vitro neuronal culture systems have proved to be fundamental and indispensable tools for the study of neural development, as well as the identification of neurotrophic factors such as nerve growth factor (NGF), ciliary trophic factors (CNTF), and brain derived neurotrophic factor (BDNF). One use of the present method may be in cultures of neuronal stem cells, such as in the use of such cultures for the generation of new neurons and glia. In such embodiments of the subject method, the cultured cells can be contacted with a compound of the present invention in order to alter the rate of proliferation of neuronal stem cells in the culture and/or alter the rate of differentiation, or to maintain the integrity of a culture of certain terminally differentiated neuronal cells. In an exemplary embodiment, the subject method can be used to culture, for example, sensory neurons or, alternatively, motorneurons. Such neuronal cultures can be used as convenient assay systems as well as sources of implantable cells for therapeutic treatments.

According to the present invention, large numbers of non-tumorigenic neural progenitor cells can be perpetuated in vitro and their rate of proliferation and/or differentiation can be affected by contact with compounds of the present invention. Generally, a method is provided comprising the steps of isolating neural progenitor cells from an animal, perpetuating these cells in vitro or in vivo, preferably in the presence of growth factors, and regulating the differentiation of these cells into particular neural phenotypes, e.g., neurons and glia, by contacting the cells with a subject compound.

Progenitor cells are thought to be under a tonic inhibitory influence which maintains the progenitors in a suppressed state until their differentiation is required. However, recent techniques have been provided which permit these cells to be proliferated, and unlike neurons which are terminally differentiated and therefore non-, dividing, they can be produced in unlimited number and are highly suitable for transplantation into heterologous and autologous hosts with neurodegenerative diseases.

By "progenitor" it is meant an oligopotent or multipotent stem cell which is able to divide without limit and, under specific conditions, can produce daughter cells which terminally differentiate such as into neurons and glia. These cells can be used for transplantation into a heterologous or autologous host. By heterologous is meant a host other than the animal from which the progenitor cells were originally derived. By autologous is meant the identical host from which the cells were originally derived.

Cells can be obtained from embryonic, post-natal, juvenile or adult neural tissue from any animal. By any animal is meant any multicellular animal which contains nervous tissue. More particularly, is meant any fish, reptile, bird, amphibian or mammal and the like. The most preferable donors are mammals, especially mice and humans.

In the case of a heterologous donor animal, the animal may be euthanized, and the brain and specific area of interest removed using a sterile procedure. Brain areas of particular interest include any area from which progenitor cells can be obtained which will serve to restore function to a degenerated area of the host's brain. These regions include areas of the central nervous system (CNS) including the cerebral cortex, cerebellum, midbrain, brainstem, spinal cord and ventricular tissue, and areas of the peripheral nervous system (PNS) including the carotid body and the adrenal medulla. More particularly, these areas include regions in the basal ganglia, preferably the striatum which consists of the caudate and putamen, or various cell groups such as the globus pallidus, the subthalamic nucleus, the nucleus basalis which is found to be degenerated in Alzheimer's Disease patients, or the substantia nigra pars compacta which is found to be degenerated in Parkinson's Disease patients.

Human heterologous neural progenitor cells may be derived from fetal tissue obtained from elective abortion, or from a post-natal, juvenile or organ donor. Autologous neural tissue can be obtained by biopsy, or from patients undergoing neurosurgery in which neural tissue is removed, in particular during epilepsy surgery, and more particularly during temporal lobectomies and hippocampalectomies.

Cells can be obtained from donor tissue by dissociation of individual cells from the connecting extracellular matrix of the tissue. Dissociation can be obtained using any known procedure, including treatment with enzymes such as trypsin, collagenase and the like, or by using physical methods of dissociation such as with a blunt instrument or by mincing with a scalpel to a allow outgrowth of specific cell types from a tissue. Dissociation of fetal cells can be carried out in tissue culture medium, while a preferable medium for dissociation of juvenile and adult cells is artificial cerebral spinal fluid (aCSF). Regular aCSF contains 124 mM NaCl, 5 mM KCl, 1.3 mM $MgCl_2$, 2 mM $CaCl_2$, 26 mM $NaHCO_3$, and 10 mM D-glucose. Low $Ca^{2+}$ aCSF contains the same ingredients except for $MgCl_2$ at a concentration of 3.2 mM and $CaCl_2$ at a concentration of 0.1 mM.

Dissociated cells can be placed into any known culture medium capable of supporting cell growth, including MEM, DMEM, RPMI, F-12, and the like, containing supplements which are required for cellular metabolism such as glutamine and other amino acids, vitamins, minerals and useful proteins such as transferrin and the like. Medium may also contain antibiotics to prevent contamination with yeast, bacteria and fungi such as penicillin, streptomycin, gentamicin and the like. In some cases, the medium may contain serum derived from bovine, equine, chicken and the like. A particularly preferable medium for cells is a mixture of DMEM and F-12.

Conditions for culturing should be close to physiological conditions. The pH of the culture media should be close to physiological pH, preferably between pH 6-8, more preferably close to pH 7, even more particularly about pH 7.4. Cells should be cultured at a temperature close to physiological temperature, preferably between 30° C.-40° C., more preferably between 32° C.-38° C., and most preferably between 35° C.-37° C.

Cells can be grown in suspension or on a fixed substrate, but proliferation of the progenitors is preferably done in suspension to generate large numbers of cells by formation of "neurospheres" (see, for example, Reynolds et al. (1992) *Science* 255:1070-1709; and PCT Publications WO93/01275, WO94/09119, WO94/10292, and WO94/16718). In the case of propagating (or splitting) suspension cells, flasks are shaken well and the neurospheres allowed to settle on the bottom corner of the flask. The spheres are then transferred to a 50 ml centrifuge tube and centrifuged at low speed. The medium is aspirated, the cells resuspended in a small amount of medium with growth factor, and the cells mechanically dissociated and resuspended in separate aliquots of media.

Cell suspensions in culture medium are supplemented with any growth factor which allows for the proliferation of progenitor cells and seeded in any receptacle capable of sustaining cells, though as set out above, preferably in culture flasks or roller bottles. Cells typically proliferate within 34 days in a 37° C. incubator, and proliferation can be reinitiated at any time after that by dissociation of the cells and resuspension in fresh medium containing growth factors.

In the absence of substrate, cells lift off the floor of the flask and continue to proliferate in suspension forming a hollow sphere of undifferentiated cells. After approximately 3-10 days in vitro, the proliferating clusters (neurospheres) are fed every 2-7 days, and more particularly every 2-4 days by gentle centrifugation and resuspension in medium containing growth factor.

After 6-7 days in vitro, individual cells in the neurospheres can be separated by physical dissociation of the neurospheres with a blunt instrument, more particularly by triturating the neurospheres with a pipette. Single cells from the dissociated neurospheres are suspended in culture medium containing growth factors, and differentiation of the cells can be control in culture by plating (or resuspending) the cells in the presence of a subject compound.

To further illustrate other uses of the subject compounds, it is noted that intracerebral grafting has emerged as an additional approach to central nervous system therapies. For example, one approach to repairing damaged brain tissues involves the transplantation of cells from fetal or neonatal animals into the adult brain (Dunnett et al. (1987) *J Exp Biol* 123:265-289; and Freund et al. (1985) *J Neurosci* 5:603-616). Fetal neurons from a variety of brain regions can be successfully incorporated into the adult brain, and such grafts can alleviate behavioral defects. For example, movement disorder induced by lesions of dopaminergic projections to the basal ganglia can be prevented by grafts of embryonic dopaminergic neurons. Complex cognitive functions that are impaired after lesions of the neocortex can also be partially restored by grafts of embryonic cortical cells. The subject method can be used to regulate the growth state in the culture, or where fetal tissue is used, especially neuronal stem cells, can be used to regulate the rate of differentiation of the stem cells.

Stem cells useful in the present invention are generally known. For example, several neural crest cells have been identified, some of which are multipotent and likely represent uncommitted neural crest cells, and others of which can generate only one type of cell, such as sensory neurons, and likely represent committed progenitor cells. The role of compounds employed in the present method to culture such stem cells can be to regulate differentiation of the uncommitted progenitor, or to regulate further restriction of the developmental fate of a committed progenitor cell towards becoming a terminally differentiated neuronal cell. For example, the present method can be used in vitro to regulate the differentiation of neural crest cells into glial cells, schwann cells, chromaffin cells, cholinergic sympathetic or parasympathetic neurons, as well as peptidergic and serotonergic neurons. The subject compounds can be used alone, or can be used in combination with other neurotrophic factors which act to more particularly enhance a particular differentiation fate of the neuronal progenitor cell.

In addition to the implantation of cells cultured in the presence of the subject compounds, yet another aspect of the present invention concerns the therapeutic application of a subject compound to regulate the growth state of neurons and other neuronal cells in both the central nervous system and the peripheral nervous system. The ability of ptc, hedgehog, and smoothened to regulate neuronal differentiation during development of the nervous system and also presumably in the adult state indicates that, in certain instances, the subject compounds can be expected to facilitate control of adult neurons with regard to maintenance, functional performance, and aging of normal cells; repair and regeneration processes in chemically or mechanically lesioned cells; and treatment of degeneration in certain pathological conditions. In light of this understanding, the present invention specifically contemplates applications of the subject method to the treatment protocol of (prevention and/or reduction of the severity of) neurological conditions deriving from: (i) acute, subacute, or chronic injury to the nervous system, including traumatic injury, chemical injury, vascular injury and deficits (such as the ischemia resulting from stroke), together with infectious/inflammatory and tumor-induced injury, (ii) aging of the nervous system including Alzheimer's disease; (iii) chronic neurodegenerative diseases of the nervous system, including Parkinson's disease, Huntington's chorea, amylotrophic lateral sclerosis and the like, as well as spinocerebellar degenerations; and (iv) chronic immunological diseases of the nervous system or affecting the nervous system, including multiple sclerosis.

As appropriate, the subject method can also be used in generating nerve prostheses for the repair of central and peripheral nerve damage. In particular, where a crushed or severed axon is intubulated by use of a prosthetic device, subject compounds can be added to the prosthetic device to regulate the rate of growth and regeneration of the dendritic processes. Exemplary nerve guidance channels are described in U.S. Pat. Nos. 5,092,871 and 4,955,892.

In another embodiment, the subject method can be used in the treatment of neoplastic or hyperplastic transformations such as may occur in the central nervous system. For instance, the subject compounds can be utilized to cause such transformed cells to become either post-mitotic or apoptotic. The present method may, therefore, be used as part of a treatment for, e.g., malignant gliomas, meningiomas, medulloblastomas, neuroectodermal tumors, and ependymomas.

In a preferred embodiment, the subject method can be used as part of a treatment regimen for malignant medulloblastoma and other primary CNS malignant neuroectodermal tumors.

In certain embodiments, the subject method is used as part of treatment program for medulloblastoma. Medulloblastoma, a primary brain tumor, is the most common brain tumor in children. A medulloblastoma is a primitive neuroectodermal tumor arising in the posterior fossa. They account for approximately 25% of all pediatric brain tumors (Miller). Histologically, they are small round cell tumors commonly arranged in true rosettes, but may display some differentiation to astrocytes, ependymal cells or neurons (Rorke; Kleihues). PNETs may arise in other areas of the brain including the pineal gland (pineoblastoma) and cerebrum. Those arising in the supratentorial region generally fare worse than their PF counterparts.

Medulloblastoma/PNETs are known to recur anywhere in the CNS after resection, and can even metastasize to bone. Pretreatment evaluation should therefore include an examination of the spinal cord to exclude the possibility of "dropped metastases". Gadolinium-enhanced MRI has largely replaced myelography for this purpose, and CSF cytology is obtained postoperatively as a routine procedure.

In other embodiments, the subject method is used as part of treatment program for ependymomas. Ependymomas account for approximately 10% of the pediatric brain tumors in children. Grossly, they are tumors that arise from the ependymal lining of the ventricles and microscopically form rosettes, canals, and perivascular rosettes. In the CHOP series of 51 children reported with ependymomas, ⅔ were histologically benign. Approximately ⅔ arose from the region of the 4th ventricle. One third presented in the supratentorial region. Age at presentation peaks between birth and 4 years, as demonstrated by SEER data as well as data from CHOP. The median age is about 5 years. Because so many children with this disease are babies, they often require multimodal therapy.

Yet another aspect of the present invention concerns the observation in the art that ptc, hedgehog, and/or smoothened are involved in morphogenic signals involved in other vertebrate organogenic pathways in addition to neuronal differentiation as described above, having apparent roles in other endodermal patterning, as well as both mesodermal and endodermal differentiation processes. Thus, it is contemplated by the invention that compositions comprising one or more of the subject compounds can also be utilized for both cell culture and therapeutic methods involving generation and maintenance of non-neuronal tissue.

In one embodiment, the present invention makes use of the discovery that ptc, hedgehog, and smoothened are apparently involved in controlling the development of stem cells responsible for formation of the digestive tract, liver, lungs, and other organs which derive from the primitive gut. Shh serves as an inductive signal from the endoderm to the mesoderm, which is critical to gut morphogenesis. Therefore, for example, compounds of the instant method can be employed for regulating the development and maintenance of an artificial liver which can have multiple metabolic functions of a normal liver. In an exemplary embodiment, the subject method can be used to regulate the proliferation and differentiation of digestive tube stem cells to form hepatocyte cultures which can be used to populate extracellular matrices, or which can be encapsulated in biocompatible polymers, to form both implantable and extracorporeal artificial livers.

In another embodiment, therapeutic compositions of subject compounds can be utilized in conjunction with transplantation of such artificial livers, as well as embryonic liver structures, to regulate uptake of intraperitoneal implantation, vascularization, and in vivo differentiation and maintenance of the engrafted liver tissue.

In yet another embodiment, the subject method can be employed therapeutically to regulate such organs after physical, chemical or pathological insult For instance, therapeutic compositions comprising subject compounds can be utilized in liver repair subsequent to a partial hepatectomy.

The generation of the pancreas and small intestine from the embryonic gut depends on intercellular signalling between the endodermal and mesodermal cells of the gut In particular, the differentiation of intestinal mesoderm into smooth muscle has been suggested to depend on signals from adjacent endodermal cells. One candidate mediator of endodermally derived signals in the embryonic hindgut is Sonic hedgehog. See, for example, Apelqvist et al. (1997) *Curr Biol* 7:801-4. The Shh gene is expressed throughout the embryonic gut endoderm with the exception of the pancreatic bud endoderm, which instead expresses high levels of the homeodomain protein Ipf1/Pdx1 (insulin promoter factor 1/pancreatic and duodenal homeobox 1), an essential regulator of early pancreatic development. Apelqvist et al., supra, have examined whether the differential expression of Shh in the embryonic gut tube controls the differentiation of the surrounding mesoderm into specialised mesoderm derivatives of the small intestine and pancreas. To test this, they used the promoter of the Ipf1/Pdx1 gene to selectively express Shh in the developing pancreatic epithelium. In Ipf1/Pdx1—Shh transgenic mice, the pancreatic mesoderm developed into smooth muscle and interstitial cells of Cajal, characteristic of the intestine, rather than into pancreatic mesenchyme and spleen. Also, pancreatic explants exposed to Shh underwent a similar program of intestinal differentiation. These results provide evidence that the differential expression of endodermally derived Shh controls the fate of adjacent mesoderm at different regions of the gut tube.

In the context of the present invention, it is contemplated therefore that the subject compounds can be used to control or regulate the proliferation and/or differentiation of pancreatic tissue both in vivo and in vitro.

There are a wide variety of pathological cell proliferative and differentiative conditions for which the inhibitors of the present invention may provide therapeutic benefits, with the general strategy being, for example, the correction of aberrant insulin expression, or modulation of differentiation. More generally, however, the present invention relates to a method of inducing and/or maintaining a differentiated state, enhancing survival and/or affecting proliferation of pancreatic cells, by contacting the cells with the subject inhibitors. For instance, it is contemplated by the invention that, in light of the apparent involvement of ptc, hedgehog, and smoothened in the formation of ordered spatial arrangements of pancreatic tissues, the subject method could be used as part of a technique to generate and/or maintain such tissue both in vitro and in vivo. For instance, modulation of the function of hedgehog can be employed in both cell culture and therapeutic methods involving generation and maintenance β-cells and possibly also for non-pancreatic tissue, such as in controlling the development and maintenance of tissue from the digestive tract, spleen, lungs, urogenital organs (e.g., bladder), and other organs which derive from the primitive gut.

In an exemplary embodiment, the present method can be used in the treatment of hyperplastic and neoplastic disorders effecting pancreatic tissue, particularly those characterized by aberrant proliferation of pancreatic cells. For instance, pancreatic cancers are marked by abnormal proliferation of pancreatic cells which can result in alterations of insulin secretory capacity of the pancreas. For instance, certain pancreatic hyperplasias, such as pancreatic carcinomas, can result in hypoinsulinemia due to dysfunction of β-cells or decreased islet cell mass. To the extent that aberrant ptc, hedgehog, and smoothened signaling may be indicated in disease progression, the subject regulators can be used to enhance regeneration of the tissue after antitumor therapy.

Moreover, manipulation of hedgehog signaling properties at different points may be useful as part of a strategy for reshaping/repairing pancreatic tissue both in vivo and in vitro. In one embodiment, the present invention makes use of the apparent involvement of ptc, hedgehog, and smoothened in regulating the development of pancreatic tissue. In general, the subject method can be employed therapeutically to regulate the pancreas after physical, chemical or pathological insult. In yet another embodiment, the subject method can be applied to cell culture techniques, and in particular, may be employed to enhance the initial generation of prosthetic pancreatic tissue devices. Manipulation of proliferation and differentiation of pancreatic tissue, for example, by altering hedgehog activity, can provide a means for more carefully controlling the characteristics of a cultured tissue. In an exemplary embodiment, the subject method can be used to augment production of prosthetic devices which require β-islet cells, such as may be used in the encapsulation devices described in, for example, the Aebischer et al. U.S. Pat. No. 4,892,538, the Aebischer et al. U.S. Pat. No. 5,106,627; the Lim U.S. Pat. No. 4,391,909, and the Sefton U.S. Pat. No. 4,353,888. Early progenitor cells to the pancreatic islets are multipotential, and apparently coactivate all the islet-specific genes from the time they first appear. As development proceeds, expression of islet-specific hormones, such as insulin, becomes restricted to the pattern of expression characteristic of mature islet cells. The phenotype of mature islet cells, however, is not stable in culture, as reappearence of embryonal traits in mature β-cells can be observed. By utilizing the subject compounds, the differentiation path or proliferative index of the cells can be regulated.

Furthermore, manipulation of the differentiative state of pancreatic tissue can be utilized in conjunction with transplantation of artificial pancreas so as to promote implantation, vascularization, and in vivo differentiation and maintenance of the engrafted tissue. For instance, manipulation of hedgehog function to affect tissue differentiation can be utilized as a means of maintaining graft viability.

Bellusci et al. (1997) *Development* 124:53 report that Sonic hedgehog regulates lung mesenchymal cell proliferation in vivo. Accordingly, the present method can be used to regulate regeneration of lung tissue, e.g., in the treatment of emphysema.

Fujita et al. (1997) *Biochem Biophys Res Commun* 238: 658 reported that Sonic hedgehog is expressed in human lung squamous carcinoma and adenocarcinoma cells. The expression of Sonic hedgehog was also detected in the human lung squamous carcinoma tissues, but not in the normal lung tissue of the same patient. They also observed that Sonic hedgehog stimulates the incorporation of BrdU into the carcinoma cells and stimulates their cell growth, while anti-Shh-N inhibited their cell growth. These results suggest that a ptc, hedgehog, and/or smoothened is involved in the cell growth of such transformed lung tissue and therefore indicates that the subject method can be used as part of a treatment of lung carcinoma and adenocarcinomas, and other proliferative disorders involving the lung epithelia.

Many other tumors may, based on evidence such as involvement of the hedgehog pathway in these tumors, or detected expression of hedgehog or its receptor in these tissues during development, be affected by treatment with the subject compounds. Such tumors include, but are by no means limited to, tumors related to Gorlin's syndrome (e.g., basal cell carcinoma, medulloblastoma, meningioma, etc.), tumors evidenced in pct knock-out mice (e.g., hemangioma, rhabdomyosarcoma, etc.), tumors resulting from gli-1 amplification (e.g., glioblastoma, sarcoma, etc.), tumors connected with TRC8, a ptc homolog (e.g., renal carcinoma, thyroid carcinoma, etc.), Ext-1-related tumors (e.g., bone cancer, etc.), Shh-induced tumors (e.g., lung cancer, chondrosarcomas, etc.), and other tumors (e.g., breast cancer, urogenital cancer (e.g., kidney, bladder, ureter, prostate, etc.), adrenal cancer, gastrointestinal cancer (e.g., stomach, intestine, etc.), etc.).

In still another embodiment of the present invention, compositions comprising one or more of the subject compounds can be used in the in vitro generation of skeletal tissue, such as from skeletogenic stem cells, as well as the in vivo treatment of skeletal tissue deficiencies. The present invention particularly contemplates the use of subject compounds to regulate the rate of chondrogenesis and/or osteogenesis. By "skeletal tissue deficiency", it is meant a deficiency in bone or other skeletal connective tissue at any site where it is desired to restore the bone or connective tissue, no matter how the deficiency originated, e.g. whether as a result of surgical intervention, removal of tumor, ulceration, implant, fracture, or other traumatic or degenerative conditions.

For instance, the method of the present invention can be used as part of a regimen for restoring cartilage function to a connective tissue. Such methods are useful in, for example, the repair of defects or lesions in cartilage tissue which is the result of degenerative wear such as that which results in arthritis, as well as other mechanical derangements which may be caused by trauma to the tissue, such as a displacement of torn meniscus tissue, meniscectomy, a Taxation of a joint by a torn ligament, malignment of joints, bone fracture, or by hereditary disease. The present reparative method is also useful for remodeling cartilage matrix, such as in plastic or reconstructive surgery, as well as periodontal surgery. The present method may also be applied to improving a previous reparative procedure, for example, following surgical repair of a meniscus, ligament, or cartilage. Furthermore, it may prevent the onset or exacerbation of degenerative disease if applied early enough after trauma.

In one embodiment of the present invention, the subject method comprises treating the afflicted connective tissue with a therapeutically sufficient amount of a subject compound to regulate a cartilage repair response in the connective tissue by managing the rate of differentiation and/or proliferation of chondrocytes embedded in the tissue. Such connective tissues as articular cartilage, interarticular cartilage (menisci), costal cartilage (connecting the true ribs and the sternum), ligaments, and tendons are particularly amenable to treatment in reconstructive and/or regenerative therapies using the subject method. As used herein, regenerative therapies include treatment of degenerative states which have progressed to the point of which impairment of the tissue is obviously manifest, as well as preventive treatments of tissue where degeneration is in its earliest stages or imminent.

In an illustrative embodiment, the subject method can be used as part of a therapeutic intervention in the treatment of cartilage of a diarthroidal joint, such as a knee, an ankle, an elbow, a hip, a wrist, a knuckle of either a finger or toe, or a tempomandibular joint. The treatment can be directed to the meniscus of the joint, to the articular cartilage of the joint, or both. To further illustrate, the subject method can be used to treat a degenerative disorder of a knee, such as which might be the result of traumatic injury (e.g., a sports injury or excessive wear) or osteoarthritis. The subject regulators may be administered as an injection into the joint with, for instance, an arthroscopic needle. In some instances, the injected agent can be in the form of a hydrogel or other slow release vehicle described above in order to permit a more extended and regular contact of the agent with the treated tissue.

The present invention further contemplates the use of the subject method in the field of cartilage transplantation and prosthetic device therapies. However, problems arise, for instance, because the characteristics of cartilage and fibrocartilage varies between different tissue: such as between articular, meniscal cartilage, ligaments, and tendons, between the two ends of the same ligament or tendon, and between the superficial and deep parts of the tissue. The zonal arrangement of these tissues may reflect a gradual change in mechanical properties, and failure occurs when implanted tissue, which has not differentiated under those conditions, lacks the ability to appropriately respond. For instance, when meniscal cartilage is used to repair anterior cruciate ligaments, the tissue undergoes a metaplasia to pure fibrous tissue. By regulating the rate of chondrogenesis, the subject method can be used to particularly address this problem, by helping to adaptively control the implanted cells in the new environment and effectively resemble hypertrophic chondrocytes of an earlier developmental stage of the tissue.

In similar fashion, the subject method can be applied to enhancing both the generation of prosthetic cartilage devices and to their implantation. The need for improved treatment has motivated research aimed at creating new cartilage that is based on collagen-glycosaminoglycan templates (Stone et al. (1990) *Clin Orthop Relat Red* 252:129), isolated chondrocytes (Grande et al. (1989) *J Orthop Res* 7:208; and Takigawa et al. (1987) *Bone Miner* 2:449), and chondrocytes attached to natural or synthetic polymers (Walitani et al. (1989) *J Bone Jt Surg* 71B:74; Vacanti et al. (1991) *Plast Reconstr Surg* 88:753; von Schroeder et al. (1991) *J Biomed Mater Res* 25:329; Freed et al. (1993) *J Biomed Mater Res*

27:11; and the Vacanti et al. U.S. Pat. No. 5,041,138). For example, chondrocytes can be grown in culture on biodegradable, biocompatible highly porous scaffolds formed from polymers such as polyglycolic acid, polylactic acid, agarose gel, or other polymers which degrade over time as function of hydrolysis of the polymer backbone into innocuous monomers. The matrices are designed to allow adequate nutrient and gas exchange to the cells until engraftment occurs. The cells can be cultured in vitro until adequate cell volume and density has developed for the cells to be implanted. One advantage of the matrices is that they can be cast or molded into a desired shape on an individual basis, so that the final product closely resembles the patient's own ear or nose (by way of example), or flexible matrices can be used which allow for manipulation at the time of implantation, as in a joint.

In one embodiment of the subject method, the implants are contacted with a subject compound during certain stages of the culturing process in order to manage the rate of differentiation of chondrocytes and the formation of hypertrophic chondrocytes in the culture.

In another embodiment, the implanted device is treated with a subject compound in order to actively remodel the implanted matrix and to make it more suitable for its intended function. As set out above with respect to tissue transplants, the artificial transplants suffer from the same deficiency of not being derived in a setting which is comparable to the actual mechanical environment in which the matrix is implanted. The ability to regulate the chondrocytes in the matrix by the subject method can allow the implant to acquire characteristics similar to the tissue for which it is intended to replace.

In yet another embodiment, the subject method is used to enhance attachment of prosthetic devices. To illustrate, the subject method can be used in the implantation of a periodontal prosthesis, wherein the treatment of the surrounding connective tissue stimulates formation of periodontal ligament about the prosthesis.

In still further embodiments, the subject method can be employed as part of a regimen for the generation of bone (osteogenesis) at a site in the animal where such skeletal tissue is deficient Indian hedgehog is particularly associated with the hypertrophic chondrocytes that are ultimately replaced by osteoblasts. For instance, administration of a compound of the present invention can be employed as part of a method for regulating the rate of bone loss in a subject For example, preparations comprising subject compounds can be employed, for example, to control endochondral ossification in the formation of a "model" for ossification.

In yet another embodiment of the present invention, a subject compound can be used to regulate spermatogenesis. The hedgehog proteins, particularly Dhh, have been shown to be involved in the differentiation and/or proliferation and maintenance of testicular germ cells. Dhh expression is initiated in Sertoli cell precursors shortly after the activation of Sry (testicular determining gene) and persists in the testis into the adult. Males are viable but infertile, owing to a complete absence of mature sperm. Examination of the developing testis in different genetic backgrounds suggests that Dhh regulates both early and late stages of spermatogenesis. Bitgood et al. (1996) *Curr Biol* 6:298. In a preferred embodiment, the subject compound can be used as a contraceptive. In similar fashion, compounds of the subject method are potentially useful for modulating normal ovarian function.

The subject method also has wide applicability to the treatment or prophylaxis of disorders afflicting epithelial tissue, as well as in cosmetic uses. In general, the method can be characterized as including a step of administering to an animal an amount of a subject compound effective to alter the growth state of a treated epithelial tissue. The mode of administration and dosage regimens will vary depending on the epithelial tissue(s) which is to be treated. For example, topical formulations will be preferred where the treated tissue is epidermal tissue, such as dermal or mucosal tissues.

A method which "promotes the healing of a wound" results in the wound healing more quickly as a result of the treatment than a similar wound heals in the absence of the treatment. "Promotion of wound healing" can also mean that the method regulates the proliferation and/or growth of, inter alia, keratinocytes, or that the wound heals with less scarring, less wound contraction, less collagen deposition and more superficial surface area. In certain instances, "promotion of wound healing" can also mean that certain methods of wound healing have improved success rates, (e.g., the take rates of skin grafts) when used together with the method of the present invention.

Despite significant progress in reconstructive surgical techniques, scarring can be an important obstacle in regaining normal function and appearance of healed skin. This is particularly true when pathologic scarring such as keloids or hypertrophic scars of the hands or face causes functional disability or physical deformity. In the severest circumstances, such scarring may precipitate psychosocial distress and a life of economic deprivation. Wound repair includes the stages of hemostasis, inflammation, proliferation, and remodeling. The proliferative stage involves multiplication of fibroblasts and endothelial and epithelial cells. Through the use of the subject method, the rate of proliferation of epithelial cells in and proximal to the wound can be controlled in order to accelerate closure of the wound and/or minimize the formation of scar tissue.

The present treatment can also be effective as part of a therapeutic regimen for treating oral and paraoral ulcers, e.g., resulting from radiation and/or chemotherapy. Such ulcers commonly develop within days after chemotherapy or radiation therapy. These ulcers usually begin as small, painful irregularly shaped lesions usually covered by a delicate gray necrotic membrane and surrounded by inflammatory tissue. In many instances, lack of treatment results in proliferation of tissue around the periphery of the lesion on an inflammatory basis. For instance, the epithelium bordering the ulcer usually demonstrates proliferative activity, resulting in loss of continuity of surface epithelium. These lesions, because of their size and loss of epithelial integrity, dispose the body to potential secondary infection. Routine ingestion of food and water becomes a very painful event and, if the ulcers proliferate throughout the alimentary canal, diarrhea usually is evident with all its complicating factors. According to the present invention, a treatment for such ulcers which includes application of a subject compound can reduce the abnormal proliferation and differentiation of the affected epithelium, helping to reduce the severity of subsequent inflammatory events.

The subject method and compositions can also be used to treat wounds resulting from dermatological diseases, such as lesions resulting from autoimmune disorders such as psoriasis. Atopic dermititis refers to skin trauma resulting from allergies associated with an immune response caused by allergens such as pollens, foods, dander, insect venoms and plant toxins.

In other embodiments, antiproliferative preparations of subject compounds can be used to inhibit lens epithelial cell proliferation to prevent post-operative complications of extracapsular cataract extraction. Cataract is an intractable eye disease and various studies on a treatment of cataract have been made. But at present, the treatment of cataract is attained by surgical operations. Cataract surgery has been applied for a long time and various operative methods have been examined. Extracapsular lens extraction has become the method of choice for removing cataracts. The major medical advantages of this technique over intracapsular extraction are lower incidence of aphakic cystoid macular edema and retinal detachment. Extracapsular extraction is also required for implantation of posterior chamber type intraocular lenses which are now considered to be the lenses of choice in most cases.

However, a disadvantage of extracapsular cataract extraction is the high incidence of posterior lens capsule opacification, often called after-cataract, which can occur in up to 50% of cases within three years after surgery. After-cataract is caused by proliferation of equatorial and anterior capsule lens epithelial cells which remain after extracapsular lens extraction. These cells proliferate to cause Sommerling rings, and along with fibroblasts which also deposit and occur on the posterior capsule, cause opacification of the posterior capsule, which interferes with vision. Prevention of after-cataract would be preferable to treatment. To inhibit secondary cataract formation, the subject method provides a means for inhibiting proliferation of the remaining lens epithelial cells. For example, such cells can be induced to remain quiescent by instilling a solution containing a preparation of a subject compound into the anterior chamber of the eye after lens removal. Furthermore, the solution can be osmotically balanced to provide minimal effective dosage when instilled into the anterior chamber of the eye, thereby inhibiting subcapsular epithelial growth with some specificity.

The subject method can also be used in the treatment of corneopathies marked by corneal epithelial cell proliferation, as for example in ocular epithelial disorders such as epithelial downgrowth or squamous cell carcinomas of the ocular surface.

Levine et al. (1997) *J Neurosci* 17:6277 show that hedgehog proteins can regulate mitogenesis and photoreceptor differentiation in the vertebrate retina, and Ihh is a candidate factor from the pigmented epithelium to promote retinal progenitor proliferation and photoreceptor differentiation. Likewise, Jensen et al. (1997) *Development* 124:363 demonstrated that treatment of cultures of perinatal mouse retinal cells with the amino-terminal fragment of Sonic hedgehog results in an increase in the proportion of cells that incorporate bromodeoxuridine, in total cell numbers, and in rod photoreceptors, amacrine cells and Muller glial cells, suggesting that Sonic hedgehog promotes the proliferation of retinal precursor cells. Thus, the subject method can be used in the treatment of proliferative diseases of retinal cells and regulate photoreceptor differentiation.

Yet another aspect of the present invention relates to the use of the subject method to control hair growth. Hair is basically composed of keratin, a tough and insoluble protein; its chief strength lies in its disulphide bond of cystine. Each individual hair comprises a cylindrical shaft and a root, and is contained in a follicle, a flask-like depression in the skin. The bottom of the follicle contains a finger-like projection termed the papilla, which consists of connective tissue from which hair grows, and through which blood vessels supply the cells with nourishment The shaft is the part that extends outwards from the skin surface, whilst the root has been described as the buried part of the hair. The base of the root expands into the hair bulb, which rests upon the papilla. Cells from which the hair is produced grow in the bulb of the follicle; they are extruded in the form of fibers as the cells proliferate in the follicle. Hair "growth" refers to the formation and elongation of the hair fiber by the dividing cells.

As is well known in the art, the common hair cycle is divided into three stages: anagen, catagen and telogen. During the active phase (anagen), the epidermal stem cells of the dermal papilla divide rapidly. Daughter cells move upward and differentiate to form the concentric layers of the hair itself. The transitional stage, catagen, is marked by the cessation of mitosis of the stem cells in the follicle. The resting stage is known as telogen, where the hair is retained within the scalp for several weeks before an emerging new hair developing below it dislodges the telogen-phase shaft from its follicle. From this model it has become clear that the larger the pool of dividing stem cells that differentiate into hair cells, the more hair growth occurs. Accordingly, methods for increasing or reducing hair growth can be carried out by potentiating or inhibiting, respectively, the proliferation of these stem cells.

In certain embodiments, the subject method can be employed as a way of reducing the growth of human hair as opposed to its conventional removal by cutting, shaving, or depilation. For instance, the present method can be used in the treatment of trichosis characterized by abnormally rapid or dense growth of hair, e.g. hypertrichosis. In an exemplary embodiment, subject compounds can be used to manage hirsutism, a disorder marked by abnormal hairiness. The subject method can also provide a process for extending the duration of depilation.

Moreover, because a subject compound will often be cytostatic to epithelial cells, rather than cytotoxic, such agents can be used to protect hair follicle cells from cytotoxic agents which require progression into S-phase of the cell-cycle for efficacy, e.g. radiation-induced death. Treatment by the subject method can provide protection by causing the hair follicle cells to become quiescent, e.g., by inhibiting the cells from entering S phase, and thereby preventing the follicle cells from undergoing mitotic catastrophe or programmed cell death. For instance, subject compounds can be used for patients undergoing chemo- or radiation-therapies which ordinarily result in hair loss. By inhibiting cell-cycle progression during such therapies, the subject treatment can protect hair follicle cells from death which might otherwise result from activation of cell death programs. After the therapy has concluded, the instant method can also be removed with concomitant relief of the inhibition of follicle cell proliferation.

The subject method can also be used in the treatment of folliculitis, such as folliculitis decalvans, folliculitis ulerythematosa reticulata or keloid folliculitis. For example, a cosmetic prepration of a subject compound can be applied topically in the treatment of pseudofolliculitis, a chronic disorder occurring most often in the submandibular region of the neck and associated with shaving, the characteristic lesions of which are erythematous papules and pustules containing buried hairs.

In another aspect of the invention, the subject method can be used to induce differentiation and/or inhibit proliferation of epithelially derived tissue. Such forms of these molecules can provide a basis for differentiation therapy for the treatment of hyperplastic and/or neoplastic conditions involving epithelial tissue. For example, such preparations can be used for the treatment of cutaneous diseases in which there is abnormal proliferation or growth of cells of the skin.

For instance, the pharmaceutical preparations of the invention are intended for the treatment of hyperplastic epidermal conditions, such as keratosis, as well as for the treatment of neoplastic epidermal conditions such as those characterized by a high proliferation rate for various skin cancers, as for example basal cell carcinoma or squamous cell carcinoma. The subject method can also be used in the treatment of autoimmune diseases affecting the skin, in particular, of dermatological diseases involving morbid proliferation and/or keratinization of the epidermis, as for example, caused by psoriasis or atopic dermatosis.

Many common diseases of the skin, such as psoriasis, squamous cell carcinoma, keratoacanthoma and actinic keratosis are characterized by localized abnormal proliferation and growth. For example, in psoriasis, which is characterized by scaly, red, elevated plaques on the skin, the keratinocytes are known to proliferate much more rapidly than normal and to differentiate less completely.

In one embodiment, the preparations of the present invention are suitable for the treatment of dermatological ailments linked to keratinization disorders causing abnormal proliferation of skin cells, which disorders may be marked by either inflammatory or non-inflammatory components. To illustrate, therapeutic preparations of a subject compound, e.g., which promotes quiescense or differentiation, can be used to treat varying forms of psoriasis, be they cutaneous, mucosal or ungual. Psoriasis, as described above, is typically characterized by epidermal keratinocytes which display marked proliferative activation and differentiation along a "regenerative" pathway. Treatment with an antiproliferative embodiment of the subject method can be used to reverse the pathological epidermal activiation and can provide a basis for sustained remission of the disease.

A variety of other keratotic lesions are also candidates for treatment with the subject method. Actinic keratoses, for example, are superficial inflammatory premalignant tumors arising on sun-exposed and irradiated skin. The lesions are erythematous to brown with variable scaling. Current therapies include excisional and cryosurgery. These treatments are painful, however, and often produce cosmetically unacceptable scarring. Accordingly, treatment of keratosis, such as actinic keratosis, can include application, preferably topical, of a subject compound composition in amounts sufficient to inhibit hyperproliferation of epidermal/epidermoid cells of the lesion.

Acne represents yet another dermatologic ailment which may be treated by the subject method. Acne vulgaris, for instance, is a multifactorial disease most commonly occurring in teenagers and young adults, and is characterized by the appearance of inflammatory and noninflammatory lesions on the face and upper trunk. The basic defect which gives rise to acne vulgaris is hypercornification of the duct of a hyperactive sebaceous gland. Hypercornification blocks the normal mobility of skin and follicle microorganisms, and in so doing, stimulates the release of lipases by *Propinobacterium acnes* and *Staphylococcus epidermidis* bacteria and *Pitrosporum ovale*, a yeast. Treatment with an antiproliferative subject compound, particularly topical preparations, may be useful for preventing the transitional features of the ducts, e.g. hypercornification, which lead to lesion formation. The subject treatment may further include, for example, antibiotics, retinoids and antiandrogens.

The present invention also provides a method for treating various forms of dermatitis. Dermatitis is a descriptive term referring to poorly demarcated lesions which are either pruritic, erythematous, scaly, blistered, weeping, fissured or crusted. These lesions arise from any of a wide variety of causes. The most common types of dermatitis are atopic, contact and diaper dermatitis. For instance, seborrheic dermatitis is a chronic, usually pruritic, dermatitis with erythema, dry, moist, or greasy scaling, and yellow crusted patches on various areas, especially the scalp, with exfoliation of an excessive amount of dry scales. The subject method can also be used in the treatment of stasis dermatitis, an often chronic, usually eczematous dermatitis. Actinic dermatitis is dermatitis that due to exposure to actinic radiation such as that from the sun, ultraviolet waves or x- or gamma-radiation. According to the present invention, the subject method can be used in the treatment and/or prevention of certain symptoms of dermatitis caused by unwanted proliferation of epithelial cells. Such therapies for these various forms of dermatitis can also include topical and systemic corticosteroids, antipuritics, and antibiotics.

Ailments which may be treated by the subject method are disorders specific to non-humans, such as mange.

In still another embodiment, the subject method can be used in the treatment of human cancers, particularly basal cell carcinomas and other tumors of epithelial tissues such as the skin. For example, subject compounds can be employed, in the subject method, as part, of a treatment for basal cell nevus syndrome (BCNS), and other other human carcinomas, adenocarcinomas, sarcomas and the like.

In a preferred embodiment, the subject method is used as part of a treatment ot prophylaxis regimen for treating (or preventing) basal cell carcinoma. The deregulation of the hedgehog signaling pathway may be a general feature of basal cell carcinomas caused by ptc mutations. Consistent overexpression of human ptc mRNA has been described in tumors of familial and sporadic BCCs, determined by in situ hybridization. Mutations that inactivate ptc may be expected to result in overexpression of mutant Ptc, because ptc displays negative autoregulation. Prior research demonstrates that overexpression of hedgehog proteins can also lead to tumorigenesis. That sonic hedgehog (Shh) has a role in tumorigenesis in the mouse has been suggested by research in which transgenic mice overexpressing Shh in the skin developed features of BCNS, including multiple BCC-like epidermal proliferations over the entire skin surface, after only a few days of skin development. A mutation in the Shh human gene from a BCC was also described; it was suggested that Shh or other Hh genes in humans could act as dominant oncogenes in humans. Sporadic ptc mutations have also been observed in BCCs from otherwise normal individuals, some of which are UV-signature mutations. In one recent study of sporadic BCCs, five UV-signature type mutations, either CT or CCTT changes, were found out of fifteen tumors determined to contain ptc mutations. Another recent analysis of sporadic ptc mutations in BCCs and neuroectodermal tumors revealed one CT change in one of three ptc mutations found in the BCCs. See, for example, Goodrich et al. (1997) *Science* 277:1109-13; Xie et al. (1997) *Cancer Res* 57:2369-72; Oro et al. (1997) *Science* 276:817-21; Xie et al. (1997) *Genes Chromosomes Cancer* 18:305-9; Stone et al. (1996) *Nature* 384:129-34; and Johnson et al. (1996) *Science* 272:1668-71.

The subject method can also be used to treat patients with BCNS, e.g., to prevent BCC or other effects of the disease which may be the result of ptc loss-of-function, hedgehog gain-of-function, or smoothened gain-of-function. Basal cell nevus syndrome is a rare autosomal dominant disorder characterized by multiple BCCs that appear at a young age. BCNS patients are very susceptible to the development of these tumors; in the second decade of life, large numbers appear, mainly on sun-exposed areas of the skin. This disease also causes a number of developmental abnormalities, including rib, head and face alterations, and sometimes polydactyly, syndactyly, and spina bifida. They also develop a number of tumor types in addition to BCCs: fibromas of the ovaries and heart, cysts of the skin and jaws, and in the central nervous system, medulloblastomas and meningiomas. The subject method can be used to prevent or treat such tumor types in BCNS and non-BCNS patients. Studies of BCNS patients show that they have both genomic and sporadic, mutations in the ptc gene, suggesting that these mutations are the ultimate cause of this disease.

In another aspect, the present invention provides pharmaceutical preparations and methods for controlling the formation of megakaryocyte-derived cells and/or controlling the functional performance of megakaryocyte-derived cells. For instance, certain of the compositions disclosed herein may be applied to the treatment or prevention of a variety hyperplastic or neoplastic conditions affecting platelets.

In another aspect, the present invention provides pharmaceutical preparations comprising the subject compounds. The compounds for use in the subject method may be conveniently formulated for administration with a biologically acceptable and/or sterile medium, such as water, buffered saline, polyol (for example, glycerol, propylene glycol, liquid polyethylene glycol and the like) or suitable mixtures thereof. The optimum concentration of the active ingredient(s) in the chosen medium can be determined empirically, according to procedures well known to medicinal chemists. As used herein, "biologically acceptable medium" includes any and all solvents, dispersion media, and the like which may be appropriate for the desired route of administration of the pharmaceutical preparation. The use of such media for pharmaceutically active substances is known in the art. Except insofar as any conventional media or agent is incompatible with the activity of the subject compounds, its use in the pharmaceutical preparation of the invention is contemplated. Suitable vehicles and their formulation inclusive of other proteins are described, for example, in the book *Remington's Pharmaceutical Sciences* (Remington's Pharmaceutical Sciences. Mack Publishing Company, Easton, Pa., USA 1985). These vehicles include injectable "deposit formulations".

Pharmaceutical formulations of the present invention can also include veterinary compositions, e.g., pharmaceutical preparations of the subject compounds suitable for veterinary uses, e.g., for the treatment of live stock or domestic animals, e.g., dogs.

Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a subject compound at a particular target site.

The preparations of the present invention may be given orally, parenterally, topically, or rectally. They are of course given by forms suitable for each administration route. For example, they are administered in tablets or capsule form, by injection, inhalation, eye lotion, ointment, suppository, controlled release patch, etc. administration by injection, infusion or inhalation; topical by lotion or ointment; and rectal by suppositories. Oral and topical administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms such as described below or by other conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous, intracerebroventricular and subcutaneous doses of the compounds of this invention for a patient will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms.

The term "treatment" is intended to encompass also prophylaxis, therapy and cure.

The patient receiving this treatment is any animal in need, including primates, in particular humans, and other mammals such as equines, cattle, swine and sheep; and poultry and pets in general.

The compound of the invention can be administered as such or in admixtures with pharmaceutically acceptable and/or sterile carriers and can also be administered in conjunction with other antimicrobial agents such as penicillins, cephalosporins, aminoglycosides and glycopeptides. Conjunctive therapy, thus includes sequential, simultaneous and separate administration of the active compound in a way that the therapeutical effects of the first administered one is not entirely disappeared when the subsequent is administered.

V Pharmaceutical Compositions

While it is possible for a compound of the present invention to be administered alone, it is preferable to administer the compound as a pharmaceutical formulation (composition). The subject compounds according to the invention may be formulated for administration in any convenient way for use in human or veterinary medicine. In certain embodiments, the compound included in the pharmaceutical preparation may be active itself, or may be a prodrug, e.g., capable of being converted to an active compound in a physiological setting.

Thus, another aspect of the present invention provides pharmaceutically acceptable compositions comprising a therapeutically effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; or (4) intravaginally or intrarectally, for example, as a pessary, cream or foam. However, in certain embodiments the subject compounds may be simply dissolved or suspended in sterile water. In certain embodiments, the pharmaceutical preparation is non-pyrogenic, i.e., does not elevate the body temperature of a patient.

The phrase "therapeutically effective amount" as used herein means that amount of a compound, material, or composition comprising a compound of the present invention which is effective for producing some desired therapeutic effect, e.g., by overcoming a ptc loss-of-function, hedgehog gain-of-function, or smoothened gain-of-function, in at least a sub-population of cells in an animal and thereby blocking the biological consequences of that pathway in the treated cells, at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject regulators from one organ, or portion of the body, to another organ, or portion of the body. Each carrier must be "acceptable" in the sense of being compatible with the other ingredients of the formulation and not injurious to the patient Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar, (14) buffering agents, such as magnesium hydroxide and aluminum hydroxide; (15) alginic acid; (16) pyrogen-free water, (17) isotonic saline; (18) Ringer's solution; (19) ethyl alcohol; (20) phosphate buffer solutions; and (21) other non-toxic compatible substances employed in pharmaceutical formulations.

As set out above, certain embodiments of the present compounds may contain a basic functional group, such as amino or alkylamino, and are, thus, capable of forming pharmaceutically acceptable salts with pharmaceutically acceptable acids. The term "pharmaceutically acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts and the like. (See, for example, Berge et al. (1977) "Pharmaceutical Salts", J. Pharm. Sci. 66:1-19)

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay, (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

It is known that sterols, such as cholesterol, will form complexes with cyclodextrins. Thus, in preferred embodiments, where the inhibitor is a steroidal alkaloid, it may be formulated with cyclodextrins, such as α, β- and γ-cyclodextrin, dimethyl-β cyclodextrin and 2-hydroxypropyl-β-cyclodextrin.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the subject compounds in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition", W.H. Freedman and CO., San Francisco, U.S.A., 1969 or "Livestock Feeds and Feeding" O and B books, Corvallis, Ore., U.S.A., 1977).

VI. Synthetic Schemes and Identification of Active Regulators

The subject compounds, and derivatives thereof, can be prepared readily by employing known synthetic methodology. As is well known in the art, these coupling reactions are carried out under relatively mild conditions and tolerate a wide range of "spectator" functionality. Additional compounds may be synthesized and tested in a combinatorial fashion, to facilitate the identification of additional compounds which may be employed in the subject method.

a. Combinatorial Libraries

The compounds of the present invention, particularly libraries of variants having various representative classes of substituents, are amenable to combinatorial chemistry and other parallel synthesis schemes (see, for example, PCT WO 94/08051). The result is that large libraries of related compounds, e.g. a variegated library of compounds represented above, can be screened rapidly in high throughput assays in order to identify potential hedgehog regulator lead compounds, as well as to refine the specificity, toxicity, and/or cytotoxic-kinetic profile of a lead compound. For instance, ptc, hedgehog, or smoothened bioactivity assays, such as may be developed using cells with either a ptc loss-of-function, hedgehog gain-of-function, or smoothened gain-of-function, can be used to screen a library of the subject compounds for those having agonist activity toward ptc or antagonist activity towards hedgehog or smoothened. Alternatively, bioactivity assays using cells with either a ptc gain-of-function, hedgehog loss-of-function, or smoothened loss-of-function, can be used to screen a library of the subject compounds for those having antagonist activity toward ptc or agonist activity towards hedgehog or smoothened.

Simply for illustration, a combinatorial library for the purposes of the present invention is a mixture of chemically related compounds which may be screened together for a desired property. The preparation of many related compounds in a single reaction greatly reduces and simplifies the number of screening processes which need to be carried out. Screening for the appropriate physical properties can be done by conventional methods.

Diversity in the library can be created at a variety of different levels. For instance, the substrate aryl groups used in the combinatorial reactions can be diverse in terms of the core aryl moiety, e.g., a variegation in terms of the ring structure, and/or can be varied with respect to the other substituents.

A variety of techniques are available in the art for generating combinatorial libraries of small organic molecules such as the subject compounds. See, for example, Blondelle et al. (1995) *Trends Anal. Chem.* 14:83; the Affymax U.S. Pat. Nos. 5,359,115 and 5,362,899: the Ellman U.S. Pat. No. 5,288,514: the Still et al. PCT publication WO 94/08051; the ArQule U.S. Pat. Nos. 5,736,412 and 5,712,171; Chen et al. (1994) JACS 116:2661: Kerr et al. (1993) *JACS* 115:252; PCT publications WO92/10092, WO93/09668 and WO91/07087; and the Lerner et al. PCT publication WO93/20242). Accordingly, a variety of libraries on the order of about 100 to 1,000,000 or more diversomers of the subject compounds can be synthesized and screened for particular activity or property.

In an exemplary embodiment, a library of candidate compound diversomers can be synthesized utilizing a scheme adapted to the techniques described in the Still et al. PCT publication WO 94/08051, e.g., being linked to a polymer bead by a hydrolyzable or photolyzable group, optionally located at one of the positions of the candidate regulators or a substituent of a synthetic intermediate. According to the Still et al. technique, the library is synthesized on a set of beads, each bead including a set of tags identifying the particular diversomer on that bead. The bead library can then be "plated" with, for example, ptc loss-of-function, hedgehog gain-of-function, or smoothened gain-of-function cells for which a hedgehog antagonist is sought. The diversomers can be released from the bead, e.g. by hydrolysis.

Many variations on the above and related pathways permit the synthesis of widely diverse libraries of compounds which may be tested as regulators of hedgehog function.

b. Screening Assays

There are a variety of assays available for determining the ability of a compound such as a hedgehog regulator to regulate ptc, smoothened, or hedgehog function, many of which can be disposed in high-throughput formats. In many drug screening programs which test libraries of compounds and natural extracts, high throughput assays are desirable in order to maximize the number of compounds surveyed in a given period of time. Thus, libraries of synthetic and natural products can be sampled for other compounds which are hedgehog regulators.

In addition to cell-free assays, test compounds can also be tested in cell-based assays. In one embodiment, cells which have a ptc loss-of-function, hedgehog gain-of-function, or smoothened gain-of-function phenotype can be contacted with a test agent of interest, with the assay scoring for, e.g., inhibition of proliferation of the cell in the presence of the test agent.

A number of gene products have been implicated in patched-mediated signal transduction, including patched, transcription factors of the cubitus interruptus (ci) family, the serine/threonine kinase fused (fu) and the gene products of costal-2, smoothened and suppressor of fused.

The induction of cells by hedgehog proteins sets in motion a cascade involving the activation and inhibition of downstream effectors, the ultimate consequence of which is, in some instances, a detectable change in the transcription or translation of a gene. Potential transcriptional targets of hedgehog-mediated signaling are the patched gene (Hidalgo and Ingham, 1990 *Development* 110, 291-301; Marigo et al., 1996) and the vertebrate homologs of the *drosophila* cubitus interruptus gene, the GLI genes (Hui et al. (1994) *Dev Biol* 162:402-413). Patched gene expression has been shown to be induced in cells of the limb bud and the neural plate that are responsive to Shh. (Marigo et al. (1996) *PNAS* 93:9346-51; Marigo et al. (1996) *Development* 122:1225-1233). The Gli genes encode putative transcription factors having zinc finger DNA binding domains (Orenic et al. (1990) *Genes & Dev* 4:1053-1067; Kinzler et al. (1990) *Mol Cell Biol* 10:634-642). Transcription of the Gli gene has been reported to be upregulated in response to hedgehog in limb buds, while transcription of the Gli3 gene is downregulated in response to hedgehog induction (Marigo et al. (1996) *Development* 122:1225-1233). By selecting transcriptional regulatory sequences from such target genes, e.g., from patched or Gli genes, that are responsible for the up- or down-regulation of these genes in response to hedgehog signalling, and operatively linking such promoters to a reporter gene, one can derive a transcription based assay which is sensitive to the ability of a specific test compound to modify hedgehog-mediated signalling pathways. Expression of the reporter gene, thus, provides a valuable screening tool for the development of compounds that act as regulators of hedgehog.

Reporter gene based assays of this invention measure the end stage of the above described cascade of events, e.g., transcriptional modulation. Accordingly, in practicing one embodiment of the assay, a reporter gene construct is inserted into the reagent cell in order to generate a detection signal dependent on ptc loss-of-function, hedgehog gain-of-function, smoothened gain-of-function, or stimulation by Shh itself. The amount of transcription from the reporter gene may be measured using any method known to those of skill in the art to be suitable. For example, mRNA expression from the reporter gene may be detected using RNAse protection or RNA-based PCR, or the protein product of the reporter gene may be identified by a characteristic stain or an intrinsic biological activity. The amount of expression from the reporter gene is then compared to the amount of expression in either the same cell in the absence of the test compound or it may be compared with the amount of transcription in a substantially identical cell that lacks the target receptor protein. Any statistically or otherwise significant decrease in the amount of transcription indicates that the test compound has in some manner agonized the normal ptc signal (or antagonized the gain-of-function hedgehog or smoothened signal), e.g., the test compound is a potential hedgehog antagonist.

Exemplification

The invention now being generally described, it will be more readily understood by reference to the following examples which are included merely for purposes of illustration of certain aspects and embodiments of the present invention, and are not intended to limit the invention.

EXAMPLE 1

Steroidal Alkaloids can Disrupt Hedgehog Signaling

Figure 2A:
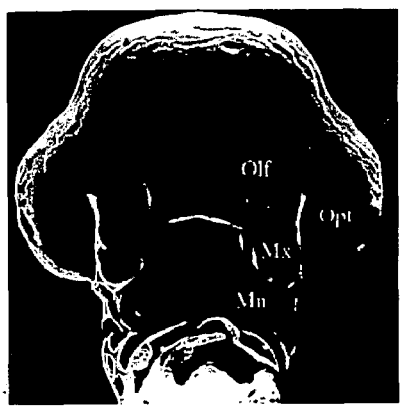
FIG. 2. Holoprosencephaly induced in chick embryos exposed to jervine (4). (A) SEM of external facial features of an untreated embryo. (B, C, D and E) Embryos exposed to 10 μ_M jervine with variable loss of midline tissue and resulting fusion of the paired, lateral olfactory processes (olf), optic vesicles (Opt), and maxillary (Mx) and mandibular (Mn) processes. A complete fusion of the optic vesicles (E) lead to true cyclopia.
Figure 2B:
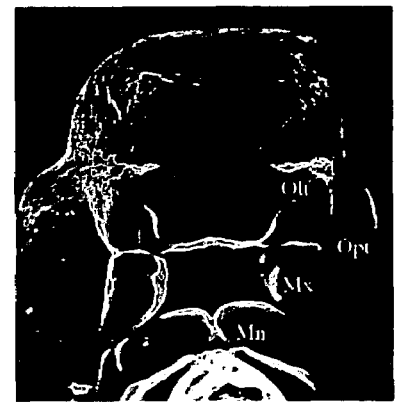
Figure 2C:
Figure 2D:
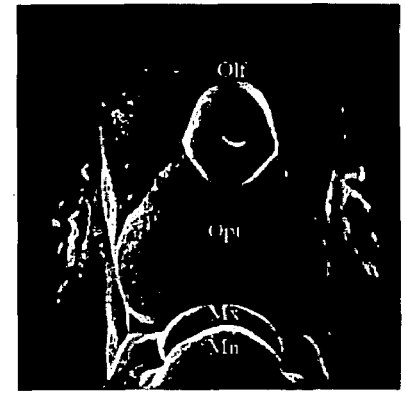
Figure 2E:
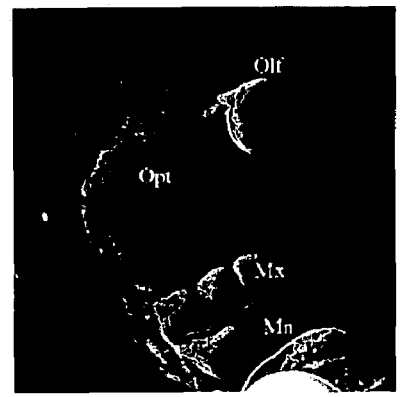

In order to demonstrate an effect on Shh signaling, we chose the chick (38) as a more tractable experimental system than the rodents, sheep and other mammals in which teratogen-induced HPE predominantly has been studied (14, 15, 16, 29, 39). Chick embryos are easily cultured and manipulated and, as seen in FIG. 2, exposure of these embryos to jervine at the intermediate to definitive streak state (40) induced external malformations characteristic of HPE (similar results were obtained with cyclopamine; data not shown). The severity of these defects varied among treated embryos, as seen in panels B-E by the degree of loss of midline structures and approximation of paired lateral structures. These midline deficits thus result in the fusion of the mandibular and maxillary processes as well as the optic vesicles and olfactory processes, with consequent cyclopia and formation of a proboscis-like structure consisting of fused nasal chambers in the most severely affected embryos (FIG. 2E).

As seen in FIG. 2 in ovo treatment produced variable defects and some embryos displayed normal morphology, even at the highest concentrations tested (50 µM, jervine 5/10 and cyclopamine 2/10, data now shown). The variability of these effects may be due to imprecise embryonic staging and difficulties in applying these hydrophobic compounds uniformly. To reduce this variability and better evaluate the potential effects of teratogenic compounds on Shh signaling we established an explant assay that allowed for precise tissue staging and more uniform application of the teratogen (41). As shown in FIG. 3A, medial neural plate with notochord was explanted from a region just rostral to Hensen's node. At this level, the medial neural plte does not yet express floor plate cell (HNF3β) or motor neuron (Isl-1) markers (42, 43, data not shown), although the notochord does express Shh (44, 45, data not shown). As seen in FIG. 3B, after a 40 hour incubation the neutral plate expresses HNF3β and Isl-1. Expression of these markers has been shown to depend upon Shh signaling, both in vivo and in vitro (2, 45), and these midline explants thus constitute an integrated assay of Shh signaling, comprising both inducing and target tissues.

To determine whether synthetic and plant-derived teratogens block Shh signaling we exposed midline explants to varying concentrations of the drugs AY 9944 and triparanol and to the steroidal alkaloids cyclopamine and jervine. As can be seen in FIGS. 3D-K, all of these compounds affect Shh signaling, with a complete loss of HNF3 and Isl-1 expression consistently caused by sufficiently high concentrations (FIGS. 3E,G,J,K). At concentrations several-fold below those required for complete inhibition, all of the teratogenic compounds are able to block HNF3β expression while retaining and often enhancing Isl-1 expression (FIGS. 3D,F,H,H). These effects are fully consistent with inhibition of Shh signaling (see below). In contract, the structurally related but not teratogenic steroidal alkaloid tomatidine (see FIG. 1, ref. 46, data not shown) is unable to block expression of HNF3β and Isl-1, even at concentrations two orders of magnitude higher than the inhibitory concentrations of jervine and cyclopamine (FIG. 3C).

Inhibitory Compounds do not Block Shh Processing

Because the midline explants contain both inducing and responding tissues, we set out to distinguish possible effects of these inhibitory compounds on signal production versus possible effects on signal response. The Shh protein undergoes an intramolecular processing reaction that involves internal cleavage and gives rise to an amino-terminal product (Shh-Nρ responsible for all known signaling activities. The first step of the autoprocessing reaction, mediated by the carboxy-terminal sequences within the precursor, entails an internal rearrangement at the site of cleavage to replace the scissile peptide bond by the thioester involving a Cys side chain. In the second step cholesterol supplies the nucleophile (the 3β-OH) that attacks the thioester intermediate, and remains covalently attached as an adduct to Shh-Nρ (11, 13). Autoprocessing thus is required to release active signal and the cholesterol adduct restricts the tissue distribution of the signal by causing it to associate with the cell surface (12,13).

Figure 4:
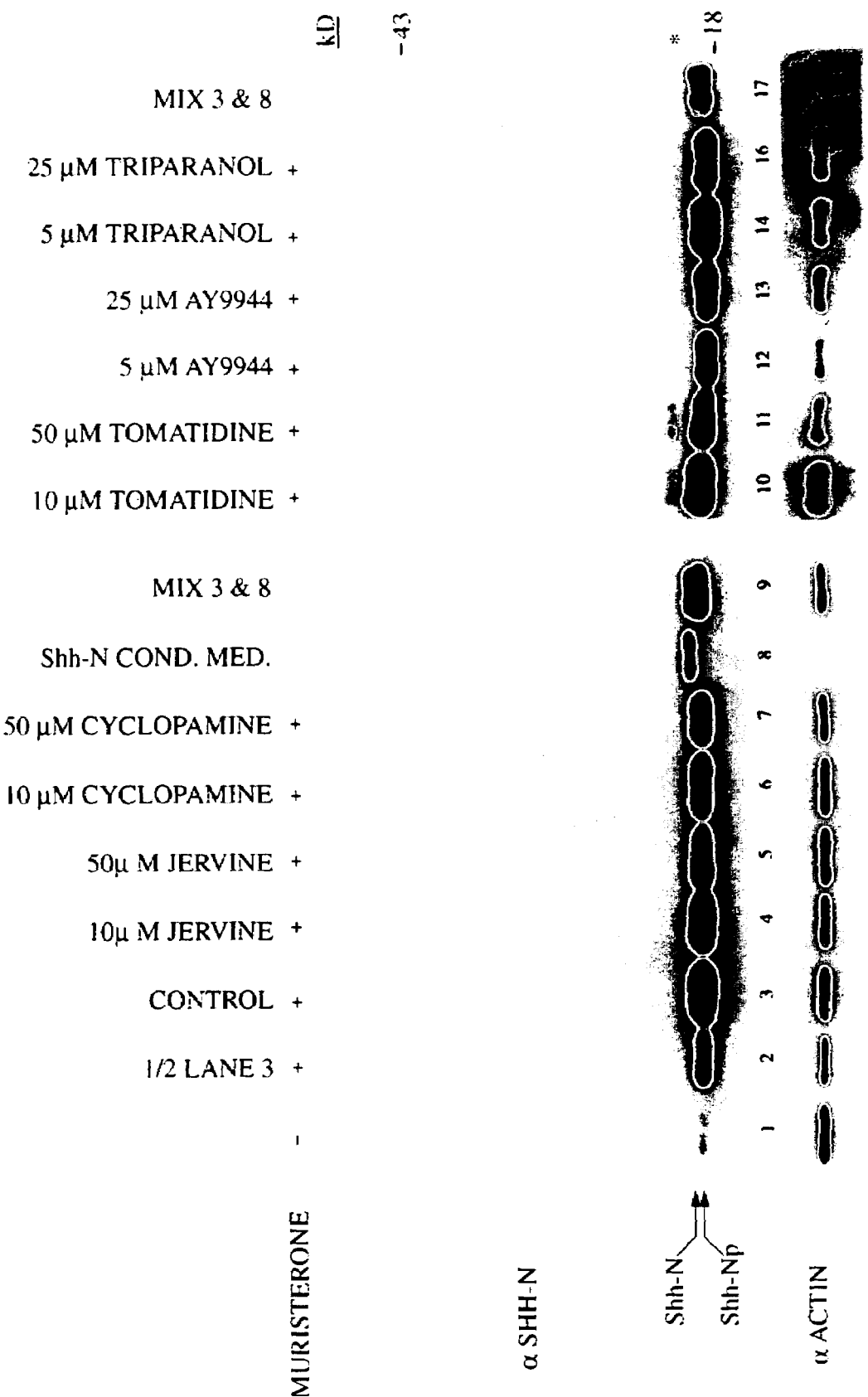
FIG. 4. Teratogenic compounds do not inhibit Shh autoprocessing in vivo (47). Stably transfected HK293 cells expressing Shh protein under ecdysone-inducible control (lanes 1, 2, 3) were treated with jervine (lanes 4, 5) cyclopamine (lanes 6, 7), tomatidine (lanes 10, 11), AY 9944 (lanes 12, 13) or triparanol (lanes 14, 15) and cell lysates were immunoblotted to assess the efficiency of autoprocessing. As seen in the untreated control (lane 3), Shh in treated cells is efficiently processed with little or no detectable accumulation of precursor protein ($M_r$45 kD). The processed amino-terminal product (Shh-$N_p$) is cell associated and migrates faster than Shh-N protein from the media of cultured cells transfected with a construct carrying an open reading frame truncated after $Gly_{198}$ (lane 8; Shh-$N_p$ and Shh-N both loaded in lanes 9 and 17). This faster migration and the lack of detectable protein in the culture medium (not shown) indicate that Shh-$N_p$ from treated cells likely carries a sterol adduct. The slower migrating species resulting from tomatidine treatment is ~1.9 kD larger, suggestive of a minor inhibition of signal sequence cleavage (see asterisk; lanes 10, 11). Immunoblotted actin for each lane is shown as a loading control.

Given this role of cholesterol in the giogenesis of Hedgehog proteins, an effect of these compounds on Shh-Nρ production is a particularly appealing possibility since jervine and cyclopamine structurally resemble cholesterol (FIG. 1) and AY 9944 and triparanol inhibit specific late-acting cholesterol biosynthetic enzymes (17, 18, 19, 22). To examine potential effects of these compounds on Shh processing we utilized HK293 cells cultured in lipid-depleted serum and carrying a stable integrated construct for expression of Shh under ecdysone-inducible control (47). Shh protein expression in these cells can be induced by addition of muristerone A, an ecdysone analog. As observed in embryos this protein is efficiently processed (FIG. 4A, lanes 1 and 2), with little or no detectable accumulation of precursor ($M_r$ 45 kD). Addition of jervine, cyclopamine, tomatidine, AY 9944, or triparanol during the 24-hour induction period did not diminish Shh-Np production nor induce accumulation of unprocessed precursor, even at doses 5-fold higher than those required to completely inhibit Shh signaling (FIG. 4A, lanes 4-13). All of the amino-terminal cleavage product generated in the presence of these compounds is detected in cell lysates, not the culture medium (data not shown), and has the same electrophoretic mobility as cholesterol-modified Shh-Np. These observations are consistent with the presence of a sterol adduct in the amino-terminal cleavage product, since lack of such an adduct is associated with release into the medium and with decreased electrophoretic mobility (the unprocessed amino-terminal fragment is designated Shh-N to distinguish it from processed Shh-Np; see lanes 8,9,17). We also failed to observe any change in efficiency of Shh processing or behavior of Shh-NP in transiently-transfected COS-7 or QT6 CELLS treated with these compounds (48). We also have observed that chick embryos treated with jervine after floor plate induction displayed the normal apical localization of Shh protein within floor plate cells (49).

Figure 5A:
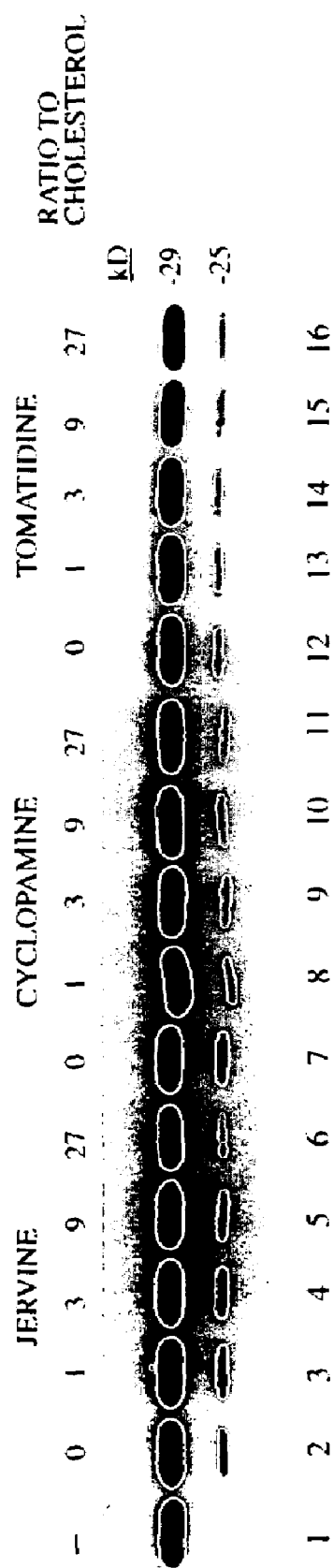
FIG. 5. Plant steriodal alkaloids do not inhibit or participate in Hh autoprocessing in vitro (5). (A) Coomassie blue-stained SDS-polyacrylamide gel showing in vitro autocleavage reactions of the baterically expressed $His_6Hh-C$ protein (~29 kD) incubated for 3 hours at 30° C. with no sterol additions (lane 1) or 12 μM cholesterol to stimulate the autoprocessing reaction and generate a ~25 kD Hh-C product (lanes 2-27 and a ~5 kD NH$_2$-terminal product (not resolved on this gel). The addition of jervine (lanes 3-6), cyclopamine (lanes 8-11) and tomatidine (lanes 13-16) does not interfere with autoprocessing, even when added in 27-fold excess to cholesterol (lanes 6, 11 and 16). (B) Coomassie blue-stained SDS-polyacrylamide gel showing that the $His_6Hh-C$ autocleavage reaction does not proceed when carried out in the absence of sterol (lane 1), or in the presence of jervine (lanes 2-5), cyclopamine (lanes 6-9) and tomatidine (lanes 10-13), even at 324 μM concentrations of these steriodal alkaloid (lanes 5, 9 and 13). (C) Coomassie blue-stained SDS0 polyacrylamide gel of $His_6Hh-C$ autocleavage reactions carried out in the absence of sterols (lane 1), with 50 mM dithiothreitol (lane 2), 12 μM cholesterol (lane 3) 12 μM7 dehydrocholesterol (lane 4) 12 μM desmosterol (lane 5), 12 μM muristerone (lanes 9, 10). The 27-carbon cholesterol precursors (lanes 4-6) stimulate $His_6Hh-C$ autocleavage reactions carried out in the absence of sterols (lane 1), with 50 mM dithiothreitol (lane 2), 12 μM cholesterol (lane 3) 12 μM 7 dehydrocholesterol (lane 4) 12 μM lathosterol (lane 6), 12 and 350 μM lanosterol (lanes 7, 8) and 12 and 350 μM muristerone (lanes 9, 10). The 27-carbon cholesterol precursors (lanes 4-6) stimulate $His_6Hh-C$ autoprocessing as efficiently as cholesterol (lane 3). The amino-terminal product migrates as a ~7 kD species (lane 2) when generated in the presence of 50 mM dithiothreitol and as a ~5 kD species. (lanes 3-6) with a sterol adduct. Lanosterol (lanes 7 and 8) and muristerone (lanes 9 and 10) do not stimulate autoprocessing above background (lane 1).
Figure 5B:
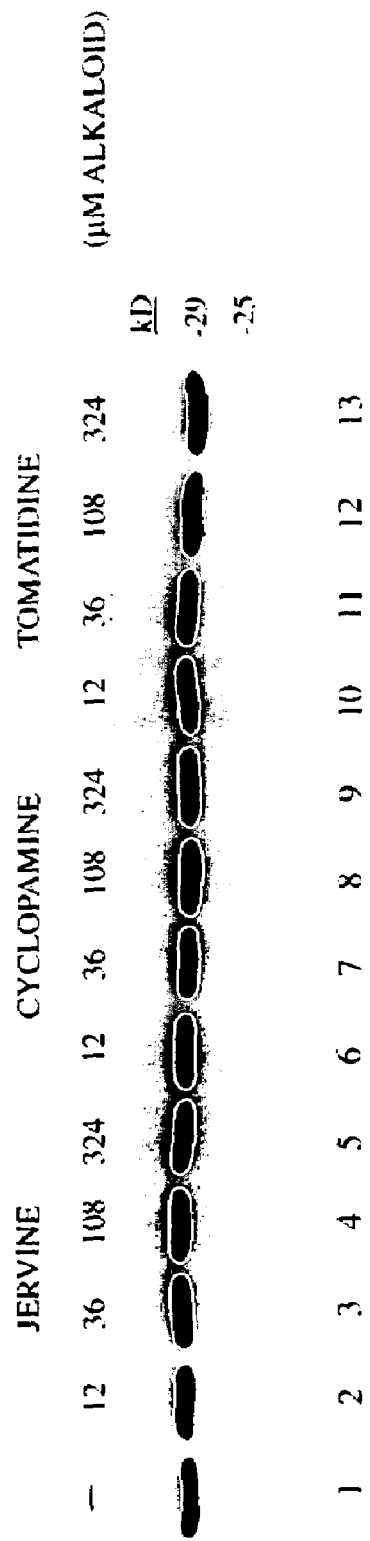

Because of their structural similarity to cholesterol, we also investigated the potential effects of the plant compounds on an in vitro autoprocessing reaction utilizing purified components. The protein utilized in this reaction is derived by replacement of all but six codons of the *Drosophila* Shh amino-terminal coding region with sequences encoding a hexahistidine purification tag (10). The resulting 29 kDa protein, His6Hh-C, in purified form undergoes autoprocessing in a cholesterol-dependent manner to yield a 25 kD product (50). As seen in FIG. 5A neither jervine, cyclopamine, nor tomatidine inhibit this cholesterol-stimulated autoprocessing reaction, even at concentrations 27-fold higher than that of cholesterol. Given the presence of 3β-OH in each of the plant compounds (FIG. 1), we also tested their ability to replace cholesterol in providing the nucleophilic group during processing. As seen in FIG. 5B, no appreciable cleavage is stimulated by addition of these compounds in the absence of cholesterol.

Figure 5C:
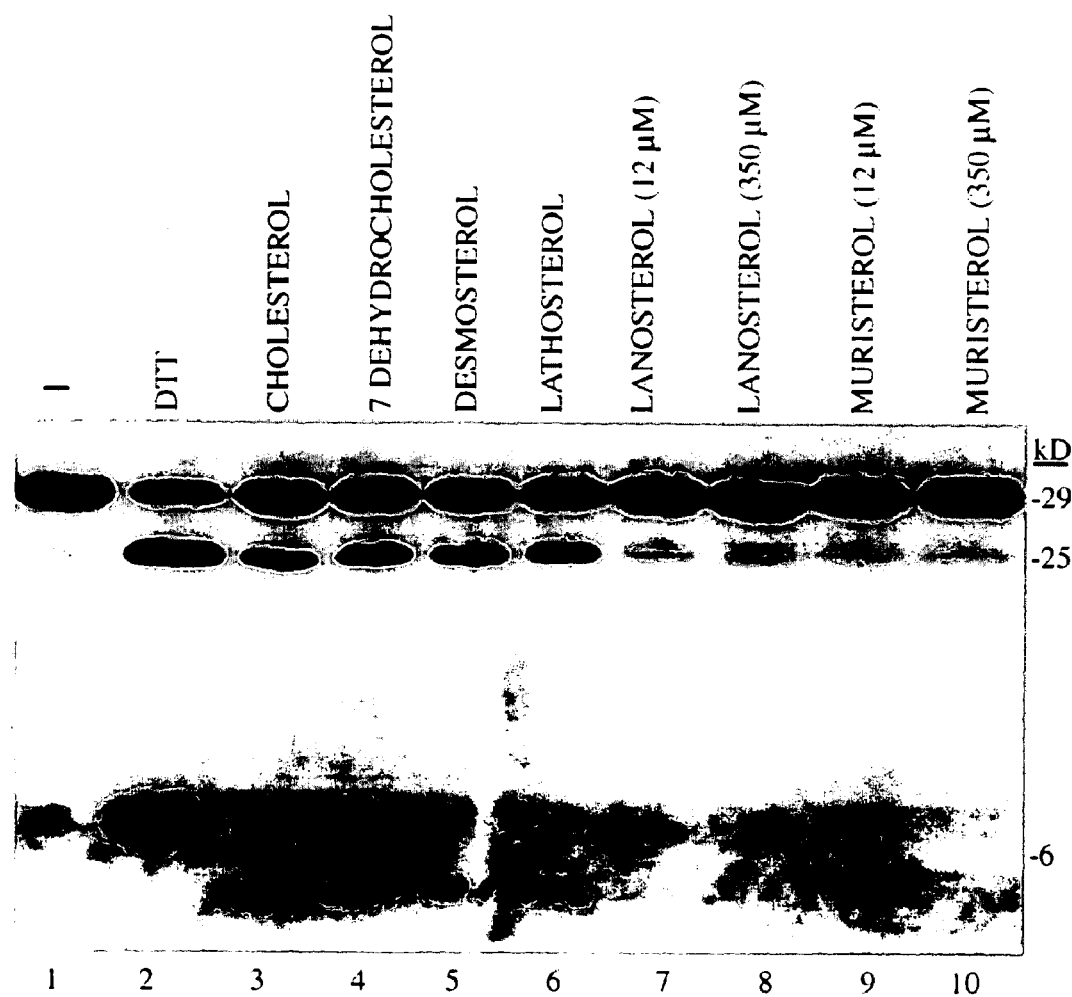

The observation that cholesterol synthesis inhibitors such as AY 9944 and triparanol do not inhibit processing raises the possibility that cholesterol biosynthetic precursors, which accumulate in treated cells (see below), may participate in the reaction. FIG. 5C shows that the in vitro reaction can be driven by desmosterol, 7-dehydrocholesterol (7DHC), and lathosterol with efficiencies similar to that of cholesterol. Desmosterol and 7DHC are the major precursors reported to accumulate in cells treated with triparanol and AY 9944, respectively. Lanosterl, a 30 carbon cholesterol precursor, on the other hand is unable to participate in the reaction, perhaps due to steric interference by the two methyl groups attached to the C4 carbon near the 3-hydroxyl. In other studies of this in vitro reaction we have observed a requirement for an unhindered hydroxyl at the 3β position on a sterol nucleus, although neither the 8-carbon side chian nor the number or position(s) of the double bond(s) in the sterol nucleus appear to critically affect efficiency (51). These observations suggest that all 27 carbon sterol intermediates in the biosynthetic pathway are potential adducts in the autoprocessing reaction, and may account for the unimpaired efficiency of processing in the presence of distal synthesis inhibitors. Thus, although the extent of Shh processing in cultured cells and its localization in vivo appears to be unaffected by these inhibitory compounds (FIG. 4), we can not rule out the possibility that the sterol adduct may differ and that such an abnormally modified signal may have distinct biological properties.

Inhibitory Compounds Specifically Affect the Response to Shh Signaling

Figure 6A:
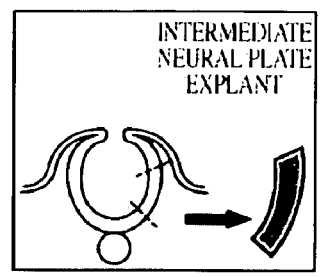
FIG. 6. Teratogenic compounds inhibit neural ectoderm response to exogenous Shh-N protein (41). (A) Intermediate neural plate ectoderm, free of notochord and other tissues, was dissected as shown (dashed lines) from stage 9-10 chick embryos at a level just rostral to Hensen's node (see FIG. 3A). (B) Explanted intermediate neural plate tissue cultured in a collagen gel matrix for 20 hours expresses the dorsal marker Pax7 (FITC) and not the floor plate marker HNF3β (Rhodamine). (C) Addition of recombinant, purified Shh-N at 2 nM suppresses Pax7 expression. (D) Markers of motor neuron (Isl-1, FITC) and floor plate cell (HNF3β, rhodamine) fates are induced upon explant culture for 40 hours in the presence of 6.25 nM Shh-N. (E) At 25 nM Shh-N, HNF3β expression expands at the expense of Isl-1 expression, which is lost. The repression of Pax7 expression by 2 nM Shh-N is inhibited by (F) 0.5 μM AY 9944, (G) 0.25 μM triparanol, (H) 0.125 μM jervine and (1) 0.0625 μM cyclopamine, but not by (J) 50 μM tomatidine. Induction of HNF3β is blocked while induction of Isl-1 at 25 NM Shh-N is maintained or expanded at intermediate levels of AY 9949 (1.0 μM, K), triparanol (0.25 μM, L), jervine (0.25 μM, M), and cyclopamine (0.125 μM, N). Tomatidine at 25 nM displays a slight inhibitory effect with decrease in HNF3β expression and an increase in the number Isl-1 expressing cells. HNF3 and Isl-1 induction are completely blocked at 2-fold higher doses of inhibitors AY 9944 (2.0 μM, P), triparanol (0.5 μM, Q), jervine (0.5, μM, R) and cyclopamine (0.25 μM, S). Tomatidine at 50 μM (T) markedly reduces HNF3β induction and enhances Isll-1 induction. Note that for each teratogenic compound the concentrations required to block complete the response to 2 nM Shh-N (F-I) are lower than those required to block completely the response to 25 nM Shh-N(P-S). Also note that the response to 25 nM Shh-N is only partially inhibited (K-N) at concentrations of teratogen 2 fold lower than those required to block this response completely. See text for further comment.
Figure 6B:
Figure 6C:
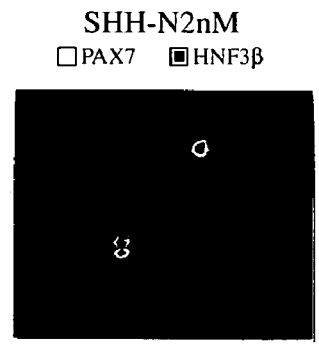
Figure 6D:
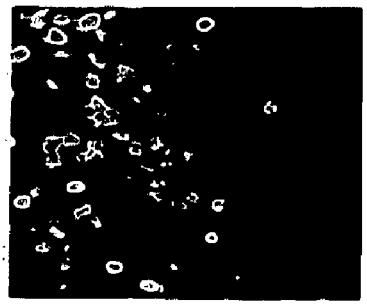
Figure 6E:
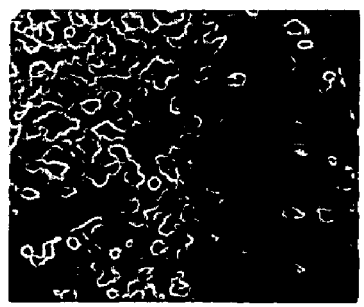
Figure 6F:
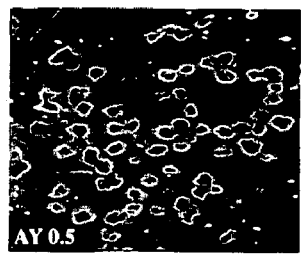
Figure 6G:
Figure 6H:
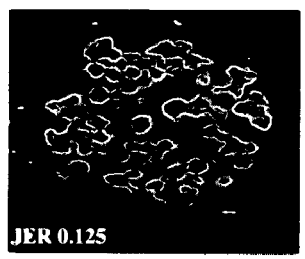
Figure 6I:
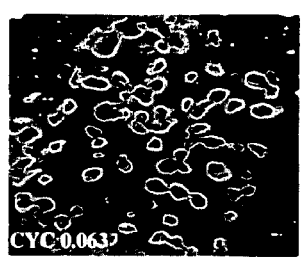
Figure 6J:
Figure 6K:
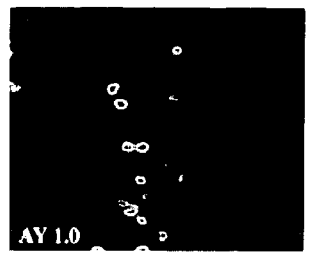
Figure 6L:
Figure 6M:
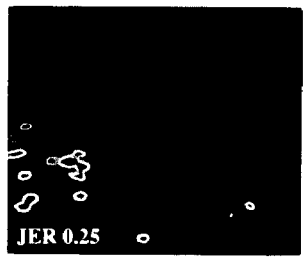
Figure 6N:
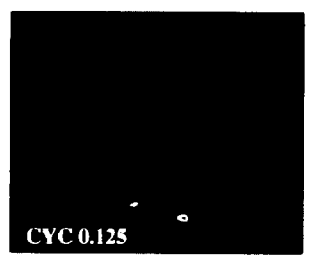
Figure 6O:
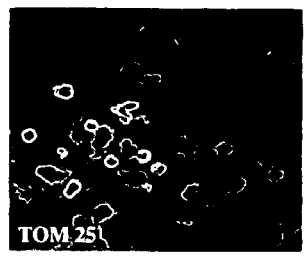
Figure 6P:
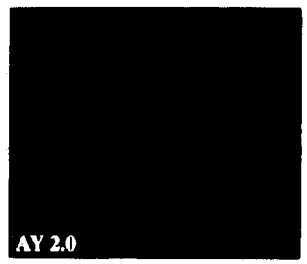
Figure 6Q:
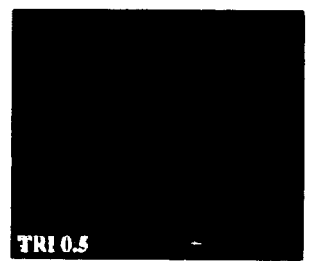
Figure 6R:
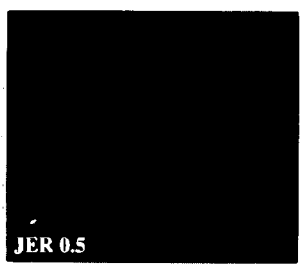
Figure 6S:
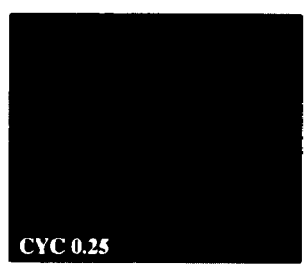

Since our studies of processing provided n evidence for an inhibitory effect of these compounds on Shh signal production, we examined the alternative possibility that these compound affect response of target tissues. For these studies we utilized an intermediate neural plate explant lacking any endogenous source of inducing signal (41, see FIG. 6A). Recombinant Shh-N protein (45, 52, 53, 54), lacking a sterol adduct, suppresses molecular markers such as Pax7 (55, see FIG. 6B, C), normally expressed in dorsal cell types, and induces ventral markers such as Isl-1 and HNF3β (FIGS. 6D,E), normally expressed in motor neurons and floor plate cells. These cellular responses are elicited in a concentration-dependent manner, with repression of Pax7 observed at concentrations of Shh-N that are insufficient for induction of HNF38 (ref. 55,2 nM, FIGS. 6B,C). Isl-1 and HNF3β occurring at the expense of Isl-1 (note that the induction of Isl-1 at 6.25 nM Shh-N in FIG. 6D is abolished at 25 nM in 6E).

Figure 6T:
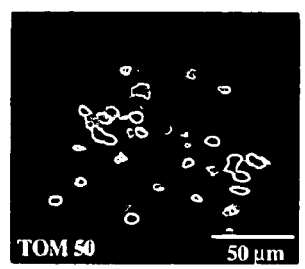

The teratogenic compounds are able to block completely the repression of Pax7 (at 2 nM Shh-N; FIG. 6F-I) and the induction of Isl-1 and HNF3β (at 25 nM Shh-N; FIG. 6)-S). In addition tomatidine produces partial inhibition, but only at concentrations 100200 fold higher than those required for complete inhibition by jervine and cyclopamine (FIG. 6T). A complete inhibition of the 24 nM response to Shh-N requires does of teratogenic compounds 24 higher than those required to completely block the 2 nM response; inhibition of responses to higher concentrations of Shh-N requires higher drug concentrations. Another dose dependent effect can be noted in FIGS. 6K-N, where drug concentrations two fold below the thresholds required for complete inhibition of the 25 nM response (induction of HNF3β) result in retention or expansion of Isl-1 expression. A similar expansion of Isl-1 at intermediate drug concentrations was seen for midline explants (FIG. 3D-G), indicating that at a fixed level of stimulation by Shh-N, distinct degrees of pathway activation can be produced by distinct inhibitor concentrations.

Figure 7A:
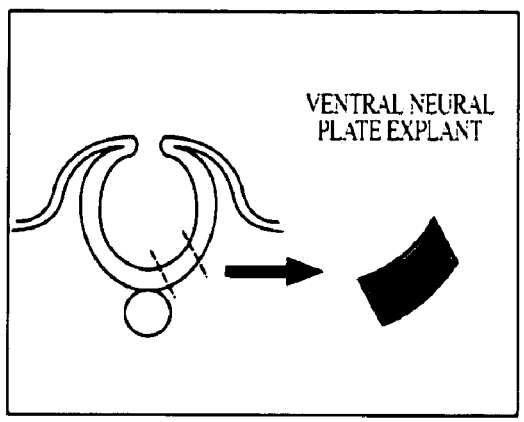
FIG. 7. Jervine does not inhibit neural ectoderm response to BMP7 (41). (A) Ventral neural plate ectoderm was dissected as shown (dashed lines) from stage 9-10 chick embryos at a level just rostral to Hensen's node (see FIG. 3A). (B) Ventral neural plate explants cultured for 24 hours in a collagen gel matrix do not give rise to any migratory cells that can be visualized by immunostaining for the HNK-1 antigen. (C) Addition of 100 ng/ml BMP7 induces formation of numerous HNK-1 positive cells that migrate out from the explant (borders outlined by white dashed line).
Figure 7B:
Figure 7C:
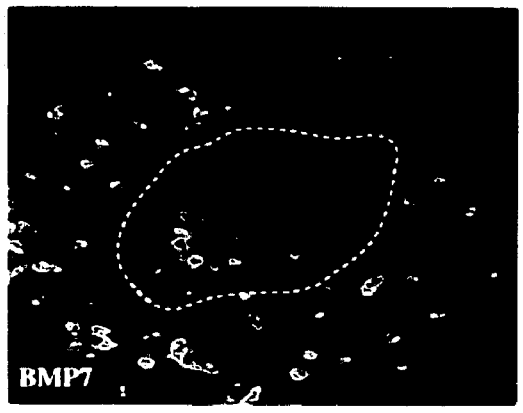
Figure 7D:
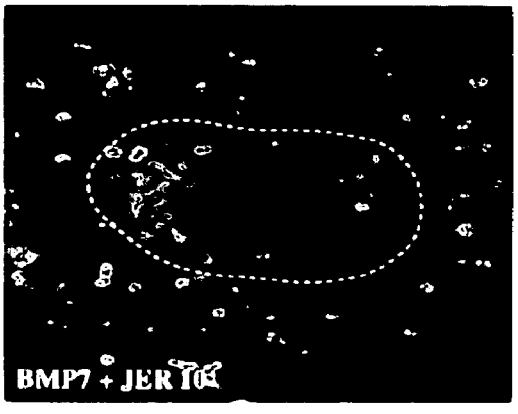

To further examine the specificity of these compounds we tested their effects on induction of a neural crest-like phenotype by BMP7. The BMP7 signaling protein is expressed in ectodermal cells adjacent to the neural plate, and appears to function in induction of neural crest and dorsal neural tube cell fates 956). To avoid contamination with endogenous lateral signals, the explants used for these studies were taken from the ventral neural plate, but excluded the notochord and the midline (FIG. 7A). Addition of BMP7 protein induced formation of migratory cells that express the HNK-1 surface antigen (compare FIGS. 7B,C), features characteristic of neutral crest cells (56). Neither cell migration nor expression HNK-1 were blocked by addition of jervine at 10 μM (FIG. 7D), a concentration exceeding that required for a complete block of Shh-N signaling. Similar results were obtained with tomatidine and with cyclopamine. These compounds also failed to inhibit formation of migratory HNK-1 positive cells from explants containing dorsal neural plate and contiguous epidermal ectoderm (49), which serves as an endogenous source of BMP activity (56).

Drug Effects Upon Cholesterol Homeostatis

Pervious reports indicate that triparanol and AY 944 cause the accumulation of cholesterol precursors (predominantly desmosterol and 7-dehycholesterol (7DHC) by specifically inhibiting late-acting enzymes of cholesterol biosynthesis (desmosterol Δ24-reductase and 7DHC Δ7-reductase, respectively, 17, 18, 19, 22), and a preliminary analysis of jervine also revealed an effect upon cholesterol biosynthesis (30). A direct comparison of the effects of these compounds on human primary lymphoblast cultures (57) revealed that all of them, including tomatidine, cause a relative decrease in cholesterol levels and an increase in the levels of other sterols (Table I, ref 58).

Table 1. Teratogenic compounds disrupt cholesterol homeostasis in cultured cells. Cholesterol biosynthesis is inhibited in primary human lymphoblasts cultured in the presence of the teratogenic compounds and tomatidine (58). The sterol profiles (57) from these cultures reveal the accumulation of multiple 27-, 28- and 29-carbon sterol precursors of cholesterol (59, 60). Esterification of PM-labeled [3H]-cholesterol in rat hepatoma cells is also inhibited by all of the compounds (63).

the plasma membrane (PM) and the endoplasmic reticulum (ER). Since cholesterol biosynthetic enzymes are located in the ER, and sterol precursors of cholesterol are highly concentrated in the PM, such a block in transport results in an overall reduction of cholesterol levels. We measured the effects of the synthetic and plant compounds upon esterification of exogenously added 3H-labelled cholesterol (63), a process which requires transport of PM cholesterol to the ER. We observed inhibition of esterification oat levels ranging for 25-75% for these compounds. An effect of AY 9944 on sterol transport previously has been reported (23), but this is the least active of the compounds we tested in inhibition of esterification. Our data therefore suggest that transport inhibition may be a factor in the effects of all of these compounds on sterol profiles, consistent with the

TABLE 1

Effects of synthetic and plant-derived compounds on cholesterol homeostasis.

A. Cholesterol Biosynthesis Assay

|  | Control | AY9944 (µM) | | | Triparanol (µM) | | | Jervine (µM) | | | Cyclopamine (µM) | | | Tomatidine (µM) | | |
| --- | --- | --- | --- | --- | --- | --- | --- | --- | --- | --- | --- | --- | --- | --- | --- | --- |
|  |  | 0.25 | 0.5 | 1.0 | 0.25 | 0.5 | 1.0 | 1.25 | 2.5 | 5.0 | 1.25 | 2.5 | 5.0 | 1.25 | 2.5 | 5.0 |
| Total Sterols (µg/mg protein) | 9.6 | 7.6 | 8.3 | 8.3 | 4.1 | 5.1 | 3.1 | 8.8 | 8.4 | 10 | 8.4 | 8.5 | 8.3 | 7.8 | 7.8 | 5.6 |
| Percent Sterols |  |  |  |  |  |  |  |  |  |  |  |  |  |  |  |  |
| Cholesterol | 95 | 30 | 33 | 34 | 56 | 45 | 51 | 90 | 90 | 88 | 87 | 76 | 68 | 54 | 42 | 32 |
| Non-Cholesterol Sterols |  |  |  |  |  |  |  |  |  |  |  |  |  |  |  |  |
| 1. C27 Sterols |  |  |  |  |  |  |  |  |  |  |  |  |  |  |  |  |
| a. Desmosterol | 1.9 |  |  |  | 9.1 | 8.7 | 6.7 | 2.5 | 2.4 | 2.7 | 4.2 | 7.1 | 11 |  |  |  |
| b. 7 Dehydrodesmosterol |  | 3.5 | 3.0 | 1.9 | 6.0 | 4.1 | 2.9 |  |  | 0.8 |  |  |  | 0.8 | 0.8 | 0.5 |
| c. Cholesta-7,24-dien-3β-ol |  | 1.8 | 1.9 | 1.6 | 3.1 | 2.4 | 2.6 |  | 0.5 | 0.5 | 0.6 | 0.9 | 1.6 | 0.9 | 0.9 | 0.7 |
| d. Zymosterol |  |  |  |  | 9.3 | 27 | 23 | 1.7 | 2.0 | 2.3 | 2.3 | 4.5 | 4.7 |  |  |  |
| e. Cholesta-8(14)-en-3β-ol |  | 9.7 | 14 | 20 | 9.1 | 8.7 | 7.3 | 1.0 | 1.7 | 2.3 | 0.9 | 2.5 | 2.7 | 6.7 | 8.9 | 8.7 |
| f. 7 Dehydrocholesterol |  | 50 | 36 | 16 |  |  |  | 1.5 | 1.4 | 1.3 | 2.4 | 4.2 | 6.3 | 19 | 14 | 9.8 |
| g. Lathosterol | 1.3 | 6.2 | 7.3 | 7.9 |  |  |  |  |  |  |  |  |  | 4.9 | 4.7 | 3.6 |
| h. C27 Sterol 1 (mw 384) |  |  |  | 5.3 |  |  |  |  |  |  |  |  |  | 7.0 | 13 | 20 |
| i. C27 Sterol 2 (mw 382) |  |  |  | 6.0 |  |  |  |  |  |  |  |  |  |  | 4.1 | 4.7 |
| j. C27 Oxysterol 1 (mw 400) |  |  |  |  |  |  |  |  |  |  |  |  |  | 1.0 | 2.4 | 4.5 |
| k. C27 Oxysterol 2 (mw 400) |  |  |  |  |  |  |  |  |  |  |  |  |  | 2.0 | 5.0 | 11 |
| 2. C28 Sterols | 0.7 |  | 1.1 | 2.6 | 4.4 | 2.6 | 1.5 | 1.2 | 0.7 | 0.7 | 1.2 | 1.3 | 1.8 |  |  | 1.6 |
| 3. C29 Sterols | 1 |  | 3.3 | 4.6 | 7.8 | 8.1 | 5.5 | 0.8 | 0.8 | 1.6 | 0.7 | 1.2 | 3.1 |  |  | 3.1 |

B. Cholesterol Esterification Assay

| Percent Inhibition (Incorporation | AY9944 (µM) | | | Triparanol (µM) | | | Jervine (µM) | | | Cyclopamine (µM) | | | Tomatidine (µM) | | |
| --- | --- | --- | --- | --- | --- | --- | --- | --- | --- | --- | --- | --- | --- | --- | --- |
| of label into cholesteryl ester*) | 2.5 | 5.0 | 10 | 2.5 | 5.0 | 10 | 2.5 | 5.0 | 10 | 2.5 | 5.0 | 10 | 2.5 | 5.0 | 10 |
| $^{3}$H-Cholesterol | 39 | 56 | 68 | 49 | 57 | 79 | 24 | 44 | 50 | 48 | 67 | 79 | 31 | 33 | 39 |
| $^{14}$C-Oleic Acid | 20 | 35 | 51 | 54 | 65 | 81 | 28 | 36 | 49 | 45 | 62 | 74 | 30 | 64 | 52 |

*The percent of label taken up that was converted to cholesteryl ester was 8%/hour for $^{3}$H-cholesterol and 3.6%/hour for $^{14}$C-oleic acid The accumulating sterols largely comprise established intermediates in the cholesterol biosynthetic pathway or closely related species that might be generated by action of the giosynthetic enzymes upon these intermediates (59). Tomatidine would appear to be the exception to this general rule, with accumulation to relatively high levels of several unusual sterols (60).

Reduction of cholesterol levels coupled with an accumulation of cholesterol biosynthetic precursors are effects observed for a group of compounds that have been termed class 2 inhibitors of cholesterol biosynthesis (61, 62). These compounds appear to act by inhibiting sterol flux between general accumulation of multiple cholesterol biosynthetic precursors. In addition, however, AY 9944 and triparanol cause accumulation to high levels of 7DHC and desmosterol, respectively, consistent with the well-known effects of these compounds on the 7DHC Δ7-reductase and desmosteroal Δ24-reductase enzymes.

Discussion

The teratogenic effects of distal inhibitors of cholesterol biosynthesis have been known and studied for more than thirty years (14, 15). Similarly, cyclopamine and jervine were identified about thirty years ago as the plant compounds responsible for the teratogenic effects of the range plant *Veratrum californicum* (28, 29). The most dramatic teratogenic effect of these compounds is the induction of cyclopia and other features of severe holoprosencephaly (HPE); the recent discovery that HPE is also caused by mutations at the murine and human loci suggested the possibility that these compounds may act to block the Shh signaling pathway. Our studies have verified the HPE-inducing properties of these compounds in chick embryos. We have further examined the early molecular correlates of these teratogenic effects and have demonstrated that these compounds block the induction by Shh protein of ventral cell types in chick neural plate explants.

Despite the inhibitory effects of these teratogens on cholesterol biosynthesis (17, 18, 19, 22, 30, see above), we found that none of the compounds appears to interfere with Shh processing in cultured cells, and that the plant alkaloids neither participate in nor inhibit an in vitro Hh protein autoprocessing reaction utilizing purified components. Instead, it is the response to Shh signaling that is affected, as indicated by failure of exogenously added Shh-N to induce ventral cell types in the presence of teratogenic compounds. Furthermore, although exogenously added Shh-N protein can induce endogenous Shh gene expression in neural plate explants (64, 65), we have demonstrated a complete inhibition of response by these teratogens at 2 nM Shh-N, a concentration at which there is not induction of floor plate cells and therefore no endogenous Shh expression. The inhibitory effects of these compounds are dose-dependent, as demonstrated: (1) by maintenance or even expansion of the Isl-1 intermediate fate at intermediate inhibitor concentrations below those required for complete inhibition; and (2), by the requirement for correspondingly higher concentrations of teratogenic compounds to inhibit the response to increasing levels of Shh-N protein. A further indication of the specificity of these effects is the inability of these compounds to block cell behaviors such as migration, expression of Pax7, or HNK-1, or the response to other inductive signals such as BMP7 at concentrations that completely block the response to Shh signaling.

Our studies of sterol synthesis and transport suggest that these compounds are acting as class 2 inhibitors of cholesterol biosynthesis (61). For several reasons, however, simple reduction of cholesterol levels seem unlikely to account for the effects of these compounds on Shh signaling. First, the non-teratogenic compound tomatidine also displays potent inhibitory effects on cholesterol synthesis. Second Shh signaling in explants is not inhibited by 25-hydroxycholesterol, a hydroxysterol that blocks de novo cholesterol biosynthesis (66). We can also rule out an inhibitory role for specific sterol precursors that may accumulate in drug-treated cells, since addition of 25-hydroycholsterol together with inhibitory compounds should eliminate synthesis of sterol precursors yet does not restore the ability to respond to Shh signaling (67). An alternative mechanism to simple reduction of cholesterol would be a disruption of intracellular transport.

We have also shown that triparanol, jervine, and cyclopamine are potent inhibitors of PM cholesterol esterification, consistent with their classification as class 2 inhibitors. Consistent with transport disruption as the mechanism of drug action in inhibiting Shh signaling, we have found that several other previously characterized class 2 compounds also are able to inhibit the response to Shh signaling in explants (68). Tomatidine, however, also blocks esterification, indicating that general inhibition of this transport pathway is not sufficient for an inhibitory effect on the Shh response. We are currently investigating the possibility that this pathway comprises multiple steps that are differentially affected by tomatidine and the teratogenic compounds, and that only those steps not essential for the Shh response are affected by tomatidine. The unusual sterols that accumulate in tomatidine-treated cells are associated with peroxisomal sterol metabolism (60), consistent with such a differential effect of tomatidine on intracellular sterol transport.

In light of these drug effects on cholesterol homeostatis, it is interesting to note the presence of a sterol sensing domain (SSD) within Ptc, a key regulator of the Shh signaling pathway (33). The Ptc SSD initially was detected as a region of similarity to the Niemann-Pick C. Disease (NP-C) gene (31, 32). The similarity between Ptc and the NP-C protein extends beyond the five transmembrane spans of the SSD to include all twelve of the proposed transmembrane spans of Ptc. The significance of this sequence homology is not known, and the role of the SSD in NP-C is not clear, although this protein is proposed to regulate intracellular trafficking and loss of its function leads to lysosomal cholesterol accumulation (69). The SSDs of other proteins confer differential responses to high and low levels of intracellular sterols. The HMGCoA reductase enzyme thus displays a 3-5 fold decrease in stability as sterol concentration rise, and this behavior is dependent on the presence of the SSD. The SCAP regulator protein at low (but not at high) sterol concentrations stimulates the activity of the S2P metalloprotease, resulting in cleaveage and activation of the SREBP transcription factor.

Those of the class 2 cholesterol synthesis inhibitors which have been examined appear to increase HMGCoA reductase activity and to stimulate the cleaveage of SREBP. Given the localization of these two proteins to the ER, a likely mechanism for this effect is that disruption of sterol transport from PM to ER by class 2 compounds induces a 'low sterol' state in these ER proteins, despite higher levels of cellular sterols overall. The teratogenic compounds studied here all affect cholesterol synthesis and transport, and it is conceivable that they alter the normal distributions of sterols within intracellular compartments If the function of Ptc is critically dependent upon the sterol concentrations in particular compartment, skewed sterol distributions in this compartment could act to perturb Ptc function via its SSD. One other possibility is that the function of Ptc in Shh signaling involves regulation of intracellular transport, as has been suggested for the related NP-C protein. If this were true, the perturbations of transport generated by these teratogenic compounds might affect the transport functions of Ptc in such a manner as to inhibit Shh signaling.

REFERENCES FOR EXAMPLE 1

1. M. Hammerschmidt, A. Brook, A. P. McMahon, *Trends Genet,* 13, 14-21 (1997).
2. C. Chiang, et al., *Nature,* 383, 407-413 (1996).
3. Y. Tanabe, T. M. Jessell, *Science* 274, 1115-1123 (1996).
4. T. P. Yamaguchi, *Curr. Opin. Genet. Dev.* 7, 513-518 (1997).
5. N. Shubin, C. Tabin, S. Carroll, *Nature* 388, 639-648 (1997).
6. A. E. Oro, et al., *Science* 276, 817-821 (1997).
7. M. M. Cohen, K. K. Sulik, *J. Craniofac. Genet. Deve. Biol.* 12, 196-244 (1992).
8. E. Belloni, et al., *Nature Genet.* 14, 353-356(1996).
9. E. Roessler, et al., *Nature Genet.* 14, 357-360 (1996).
10. J. A. Porter, et al., *Nature* 374, 363-366 (1995).
11. J. A. Porter, K. E. Young, P. A. Beacy, *Science* 274, 255-259 (1996b).

12. J. J. Lee, et al., *Science* 266, 1528-1537 (1994).
13. J. A. Porter, et al., *Cell* 86, 21-34 (1996a).
14. C. Roux, *Arch. Franc. Pediatr.* 21, 451-464 (1964).
15. C. Roux, *C. R. Soc. Biol.* 160, 1353-1357 (1966).
16. D. B. Dehart, L. Lanoue, G. S. Tinit, K. K. Sulik, *Am J. Med. Genet.* 68, 328-337 (1997).
17. M. Kraml, J. F. Bagli, D. Dvornik, *Biochem. and Biophysical Res. Com.* 15, 455-457 (1964).
18. J. Avigan, D. Steinberg, H. E. Vroman, M. J. Thompson, E. Mosettig, *J. Biol. Chem* 235, 3123-3126 (1960).
19. R. B. Clayton, A. N. Nelson, I. D. Frantz Jr., *J. Lipid Res.* 4, 166-178 (1963).
20. J. Aufenanger, J. Pill, K. Stegmeier, F. H. Schmidt, *Horm. Metabol. Res.* 17, 612-613 (1986).
21. J. Aufenanger, J. Pill, F. H. Schmidt, K. Stegmeier, *Biochem. Pharmacol.* 35, 911-916 (1986).
22. G. Popjak, A. Meenean, E. J. Parish, W. D. Nes, *J. Biol. Chem* 264, 6230-6238 (1989).
23. H. Yoshikawa, *Brain DeVe.* 13, 115-120 (1991).
24. R. I. Kelley, et al., *Am. J. Of Med. Gen.* 66, 478-484 (1996).
25. G. S. Tint, et al., *New England Journal of Medicine* 330, 107-113 (1994).
26. T. E. Willnow, et al., *Proc. Natl. Acad. Sci* USA 93, 8460-8464 (1996).
27. S. Stefansson, D. A. Chappell, K. M. Argraves, D. K. Strickland, W. S. Argraves, *J. Biol. Chem.* 270, 19417-19421 (1995).
28. W. Binns, L. F. James, J. L. Shupe, G. Everett, *Am. J. Vet. Res.* 24, 1164-1174 (1963).
29. R. F. Keeler, W. Binns, *Teratology* 1, 5-10 (1968).
30. P. A. Beachy, et al., *CSH Symp. Quant. Biol.* 62, in press (1997).
31. E. D. Carstea, et al., *Science* 277, 228-231 (1997).
32. S. K. Loftus, et al., *Science* 277, 232-235 (1977).
33. L. V. Goodrich, L. Milenkovic, K. M. Higgins, M. P. Scott, *Science* 277, 1109-1113 (1997).
34. H. Kumagai, K. T. Chun, R. D. Simoni, *J. Biol. Chem.* 270, 19107-19113 (1995).
35. G. Gil, J. R. Faust, D. J. Chin, J. L. Goldstien, M. S. Brown, *Cell* 41, 249-258 (1985).
36. X. Hua, A. Nohturfft J. L. Goldstein, M. S. Brown, *Cell* 87, 415-426 (1996).
37. M. S. Brown, J. L. Goldstein, *Cell* 89, 331-340 (1997).
38. M. M. Bryden, C. Perry, R. F. Keeler, *Teratology* 8, 18-28 (1973).
39. M. L. Omnell, F. R. P. Sim, R. F. Keeler, L. C. Harne, K. W. Brown, *Teratology* 42, 105-119 (1990).
40. Fertile chick eggs (white leghorn) were placed in a humidified incubator at 37.5° C. in a rotating tray for 14 hours. The eggs were windowed at the air space and 250 µl of a sonicated 1 mg/ml jervine solution (Leibovitz's L15 medium, Gibco BRL) was applied under the shell membrane. The window was taped and the eggs incubated for an additional 4 days. The embryos were dissected in phosphate buffered saline (PBS, pH 7.2). The heads were removed form the trunk at the superior boarder of the heart and fixed in 3% Glutaraldehyde (EM grade, Polysciences, Inc.) in 0.1M sodium cacodylate (Polysciences, Inc.), 3 mM $CaC_{1s}$ (pH 7.4) overnight at 4° C. They were washed in 0.1M sodium cacodylate (pH 7.4 placed in 2% osmium tetroxide (Polysciences, Inc.), 0.1M sodium cacodylate (pH 7.4) for 2 hours and washed in water. The samples were then dehydrated in a 50%, 70%, 90% and 100% ethanol series. Samples were critical point dried in liquid $CO_2$ (CPD Model 10, Polaron), sputtter coated with gold-palladium (Denton Desk II unit) and viewed on an Amray 1810 SEM operated at 20 kV.
41. Hamburger and Hamilton stage 9-10 (8-10 somites) embryos were used for all explant assays. Dissections were carried out in Leibovitz's L15 medium (Gibco BRL). Midline tissue just rostral to Hensen's node and well caudal to the last somite was removed with fine scissors. The neural ectoderm was separated from the lateral plate mesoderm and endoderm with dispase (Boehringer Mannheim, grade II 2.4 U/ml) treatment and then washed in L15. Midline, intermediate and ventral neural plate explants were further dissected with tungsten needles as diagrammed in FIGS. 3A, 6A and 7A. Dissected tissues were transferred to a chambered coverglass (Nunc) in a drop of collagen (vitrogen 100, Collagen Biomaterials, Palo Alto, Calif.) containing 1× modified Eagle's medium (Gibco BRL) and 24 mM $NaH_2CO_3$ (final pH 7.4-7.6), and warmed to 37.5° C. for 30 minutes (in the absence of $CO_2$) for gelation. Explants were cultured in 400 µl of F12 Nutrient Mixture (Ham) with glutamine (Gibco BRL), containing N-2 supplement (1×, Gibco BRL) and 100 U/ml penicillin and 100 ug/ml streptomycin in a 5% $CO_2$, humidified incubator at 37° C. AY 9944, triparanol, jervine, cyclopamine and tomatidine (all from 10 mM stocks in 95% ethanol, except AY 9944 which is water soluble), purified Shh-N and BMP 7 were added at the initiation of the cultures. All of the explants were cultured for 40-48 hours except for the intermediate neural plate explants assayed for pax7 repression, which were cultured for 20-22 hours. At the end of the incubation period, explants were fixed in 4.0% formaldehyde (EM grade, Polysciences, Inc.) in PBS for 1 hour at 4° C., washed with PBS and then stained with a secondary antibody for 2 hours at room temperature. Rabbit anti-rat HNF3β (K2) 1:2000, mouse anti-ISL1 (40.2D6) 1:1000, mouse anti-pax7 1:10, mouse anti-rat HNK-1/N-CAM (sigma Biosciences) 1:1000, FITC-conjugated donkey anti-mouse IgG (Jackson ImmunoResearch Laboratories, Inc.) 1:100 and LRSC-conjugated donkey anti-rabbit IgG (Jackson ImmunoResearch Laboratories, Inc.) 1:300 were all diluted in PBTS. The explants were examined with an Olympus IX60 inverted microscope using a planapo objective with a 1.4 numerical aperture. Images were generated by confocal laser scanning microscopy with a cripton-argon laser exciting at 488 and 568 nm with emissions at 450-550 and 550-650 nm and utilizing Oz with Intervission software (Noran) on a Silicon Graphics Inc. platform.
42. A Ruiz I Altaba, M. Placzek, M. Baldassare, J. Dodd, T. M. Jessell, *Dev. Biol.* 170, 299-313 (1995).
43. J. Ericson, S. Thor, T. Edlund, T. M. Jessell, T. Yamada, *Science* 256, 1555-1560 (1992).
44. Y. Echelard, et al., *Cell* 75, 1417-1430 (1993).
45. H. Roelink, et al., *Cell* 81, 445-455 (1995).
46. W. Gaffield, R. F. Keeler, *J. Natural Toxins* 5, 25-38 (1996).
47. HK293 cells, stably transfected with Shh using the Ecdysone-Inducible Mammalian Expression System (invitrogen), were plated in 6-well culture plates (Flacon, well area 9.6 cm²) in Dulbecco's modified Eagle's medium (DMEM, Gibco), 10% fetal bovine serum (FBS), 400 µg/ml Zeocin Invitrogen), 2 mM L-glutamine, 100 U/ml Penecillin, 100 µg/ml Stregtomycin, 350 µg/ml G418 (Invitrogen) at 30-40% confluency and grown at 37° C. The following day, the media was changed to one that contained 10% dilapidated serum (K. M. Gibson et al, *J. Lipid Res.* 31, 515 (1990)) and 1% ITS (Sigma) and otherwise was the same as above. After 24 hours, the cells were induced to express Shh with the addition of 1 µM muristerone A (Invitrogen). AY 9944, triparanol, jervine, cyclopamine and tomatidine (all from 10 mM stocks in 95% ethanol, except AY 9944 which is water soluble) were added to the cultures at the time of induction. The control cells received 0.475% ethanol to equal the maximum ethanol concentration in the 50 µM steriodal alkaloid treatments. After an additional 24 hours, the culture supernatants were removed and the cells were lysed in the plate with 3× SDS-PAGE cell lysis buffer (3% SDS), diluted two-fold with water and boiled. Lysate samples (and in a separate experiment supernatant samples, for which the data is not shown) were loaded onto SDS-12% polyacrylamide gels for analysis, immunoblotted with primary antibodies for Shh-N and actin (Amersham) and horseradish peroxidase-conjugated secondary antibodies (Jackson ImmunoResearch Laboratories, Inc.), and visualized with a with luminescent substrate (Pierce).

48. Shh processing in transiently transfected cells is ineffecient, with accumulation of 50-80% of Shh protein as unprocessed precursor. Even in these circumstances, we did not observe any effect of jervine, cyclopamine, or tomatidine upon Shh processing efficiency.

49. Unpublished data.

50. The in vitro studies of Hi autoprocessing used a baterially expressed derivative of the *Drosophila* Hh protein (Porter 96A). The reactions were carried out as described (Porter 96B), except that the sterols and steroidal alkaloids were dried down from an ethanol or chloroform stock and resuspended in a 0.2% Triton-X 100 solution in a bath sonicator prior to addition to the reaction mixture.

51. Other sterols that participate in the reaction with similar efficiency to cholesterol are β-sitosterol, 5-androsten-3β-ol, ergosterol, 4β-hydroxycholesterol, 19-hydroxycholesterol, 20α-hydroxycholesterol, 22(S)-hydroxycholesterol, 22(R)-hydroxycholesterol and 25-hydroxycholesterol. Epicholesterol, cholesterol acetate, α-ecdysone, 20-OH ecdysone and thiocholesterol are unable to participatein the reaction.

52. C.-M. Fan, M. Tessier-Lavigne, *Cell* 79, 1175-1186 (1994).

53. M. Hynes, et al., *Neuron* 15, 35-44 (1995).

54. A. Lopez-Martinez, et al., *Current Biology* 5, 791-796 (1995).

55. J. Ericson, S. Morton, A. Kawakami, H. Roelink, T. M. Jessell, *Cell* 87, 661-673 (1996).

56. K. F. Liem, G. Tremml, H. Roelink, T. M. Jessell, *Cell* 82, 969-979 (1995).

57. Pooled human lymphoblasts were washed with serum free RPMI-1640, then plated in 35 mm microwells in RPMI-1640 with 15% delipidated FBS (Gibson 90) and cultured at 37° C. in a 5% $CO_2$ humidified atmosphere for 12 hours. AY 9944, triparanol, jervine, cyclopamine or tomatidine was then added and the cells were incubated for five days, after which the neutral sterols were extracted and analyzed as described by R. I. Kelley (Clin. Chim. Acta 236, 45 (1995)). Briefly, pelleted cells were saponified at 60° C. in 4% (w/v) KOH in 90% ethanol with epicoprostanol as carrier, mixed with an equal volume of water and extracted three times in hexane. The hexane extracts were dried under nitrogen, derivatized with bistrimethylsilyltrifluoroacetamide (BSTFA, Pierce) in pyridine and analyzed by selected ion monitoring gas chromatography/mass-spectrometry (SIM-GC/MS), utilizing a Hewlett Packard (HP) 5890A splitless injection port, a 0.2 mm×25 m HP-1 methylsilicone (0.33 µM liquid phase) capillary column and a HP 5970A mass selective dector operated in electron impact mode at 70 eV with an ion source temperature of 200° C.

58. For determining their effects on sterol composition, AY 9944 and triparanol were used at 0.5 µM and jervine, cyclopamine, and tomatidine were used at 10 µM. Doses lower than these produced more normal sterol profiles; higher doses increased the relative levels of cholesterol precursors but also reduced cell growth during the five day incubation period of this assay.

59. Sterols 1a, 1c-g, 2a,b and 3a,b are all intermediates in normal cholesterol biosynthesis, and 1b is thought to derive from 1a (G. Salen et al., J. Lipid Res. 37, 1169 (1996)).

60. Sterol 1 h is associated with peroxisomal sterol synthesis and is particularly prominent in tomatidine treated cells. Sterol 4 is seen only in normal cells treated with tomatidine, but not in tomatidine-treated cells from Zellweger's Syndrome patients, which lack peroxisomes. Sterol 4 is an apparent dihydroxy-ketosterol whose structure is not yet fully resolved.

61. Y. Lange, T. L. Steck, *J. Biol. Chem.* 269, 29371-29374 (1994).

62. Y. Lange, T. L. Steck, *Trends in Cell Biol.* 6, 205-208 (1996).

63. Esterification of plasma membrane [$^3$H] cholesterol in hepatoma cells was assayed according to Lange and Steck. Briefly, AH22 Hepatoma cells were cultured in 25 $cm^2$ flasks to ~89-90% confluency in DMEM 10% FBS at 37° C. The cells were washed in PBS and then labeled with 1.38 µCi [$^3$H] cholesterol ($3.17\times10^{-5}$ mmol cholesterol) in PBS for 10 minutes at 37° C. The [$^3$H]cholesterol was in a vortexed solution of 2.5% Triton WR-1339, 2.5 mM NaPi (pH 7.5) and 0.125 M sucrose. The cells were then washed in PBS with 0.5 mg/ml bovne serumalbumin (BSA) and incubated for 1.5 hours at 37° C. in DMEM 10% FBS without or with AY 9944, triparanol, jervine, cyclopamine or tomatidine. The cells were detached with trypsin, washed and suspended in 1 ml PBS. The sterols were then extracted with 2.5 ml of chloroform:methanol (2:1), dried on a speed vacuum concentrator, resuspendedin 50 µl of chloroform and spotte don solica gel G coated TLC plates (Merck). Cholesteryl esters and cholesterol were fractionated with a heptane:ether:acetic acid solvent (20:5:1), dried, visualized with $I_2$ vapor, scraped and counted directly m an aqueous scintillation counting cocktail (Econo-Safe, Research Products International Corp.)

64. E. Marti, D. A. Bumcrot, R. Takada, A. P. McMahon, *Nature* 375, 322 325 (1995).

65. Thomas M. Jessell, personal communication.

66. None of the explant responses to treatment with 2 nM or 25 nM Shh-N were affected by additional of 25-OH cholesterol at 25 µM. 25-OH cholesterol is a potent inhibitor of HMG CoA reductase and at the concentrations used blocks de novo cholesterol synthesis in chick embryos and in cultured cell systems (data not shown; S. C. Miller and G. Melnykovych, *J. Lipid Res.* 25, 991 (1984); J. J. Bell, T. E. Sargeant and J. A. Watson, *J. Bio. Chem.* 251, 1745 (1976)).

67. Addition of 25 µM 25-hydroxycholesterol to explant cultures did not reverse the inhibitory effects of any of the teratogenic compounds.

68. Class 2 cholesterol synthesis inhibitors at the given concentrations block the response of intermediate neural plate explants to 25 nM Shh-N, without affecting signaling by BMP7:U 18666A 0.25 µM, chloroquine 50 µM, imipramine 75 µM, progesterone 20 µM.

69. P. G. Pentchev, et al., *Biochimica et Biophysica Acta* 1225, 235-243 (1994).

EXAMPLE 2

Essential Role for SONIC Hedgehog During Hair Follicle Morphogenesis

The hair follicle is a source of epithelial stem cells and site of origin for several types of skin tumors. While it is clear that follicles arise by way of a series of inductive tissue interactions, identification of the signaling molecules driving this process remains a major challenge in skin biology. In this study we report an obligatory role for the secreted morphogen Sonic hedgehog (Shh) during hair follicle development. Hair germs comprising epidermal placodes and associated dermal condensates were detected in both control and Shh −/− embryos, but progression through subsequent stages of follicle development was blocked in mutant skin. The expression of Gli1 and Ptc1 was reduced in Shh −/− dermal condensates and they failed to evolve into hair follicle papillae, suggesting that the adjacent mesenchyme is a critical target for placode-derived Shh. Despite the profound inhibition of hair follicle morphogenesis, late-stage follicle differentiation markers were detected in Shh −/− skin grafts, as well as cultured vibrissa explants treated with cyclopamine to block Shh signaling. Our findings reveal an essential role for Shh during hair follicle morphogenesis, where it is required for normal advancement beyond the hair germ stage of development.

Introduction

Early stages of organogenesis are marked by the appearance of mesenchymal condensates and focal cellular aggregates, or placodes, in adjacent epithelia. This process is driven to completion by a series of inductive signals traveling between epithelial and mesenchymal cell populations which ultimately give rise to the adult structure (reviewed in Gurdon, 1992; Thesleff et al., 1995). In skin appendages such as vibrissae and hair follicles, detailed analysis of tissue recombinants has revealed the existence of at least three morphogenetic signals: the embryonic dermis instructs overlying ectoderm to initiate placode formation; the placode transmits a signal generating a dermal condensate with hair follicle-inductive properties; and the condensate in turn sends a signal to nascent follicle keratinocytes stimulating their proliferation, downgrowth into the developing dermis, and reorganization to form the mature follicle (reviewed in Sengel, 1976; Hardy, 1992). The epithelial and mesenchymal components of the follicle remain in close proximity in mature hair bulbs, where the dermal papilla is surrounded by matrix cells giving rise to at least six phenotypically distinct epithelial cell types in the hair shaft and inner root sheath of the hair follicle. After birth the follicle epithelium cycles through periods of active growth (anagen), followed by regression (catagen) and inactivity (telogen) (reviewed in Cotsarelis, 1997). The morphogenetic program that accompanies the transition from telogen to anagen bears similarities to follicle development during embryogenesis, making this structure a unique model for studying certain aspects of organogenesis in the adult animal. Although a large number of genes have been implicated at various stages of hair follicle development and cycling (reviewed in Rosenquist and Martin, 1996; Sterm et al, 1996; Widelitz et al, 1997; Millar, 1997), the molecular nature of the inductive signals that underlie the formation of the follicle is largely unknown.

In situ localization of transcripts encoding potential morphogens has revealed focal expression of Sunic hedgehog (Shh) in placodes of the epidermis and several other epithelia at early stages of development, with Ptc1 transcripts encoding a putative Shh receptor also present in adjacent mesenchymal cells (Bitgood and McMahon, 1995; Iseki et al., 1996; Oro et al., 1997; Motoyama et al., 1998). These findings, coupled with the accumulating evidence demonstrating a pivotal role for secreted Hedgehog proteins in a variety of developmental processes (reviewed in Hammerschmidt et aL, 1997), led us to examine the potential involvement of this pathway in hair follicle morphogenesis. Since the follicle is a source of cutaneous stem cells and a likely, site of origin for certain epithelial skin cancers (Cotsarelis et al., 1990; Lavker et al., 1993; Rochat et al., 1994; Hansen and Tennant, 1994), understanding the developmental biology of this organ is likely to provide insights relevant to normal skin function as well as wound-healing and neoplasia, and may shed light on fundamental aspects of organogenesis involving other structures as well.

Methods

Animals and Skin Transplantation

The generation and identification of Shh mutant mice was performed as described (Chiang et al., 1996). Embryonic skin was grafted onto the dorsal fascia of nude mice beneath a protective silicone chamber using a modification of a previously-described technique (Dlugosz et al., 1995). The chamber was removed 11-12 days after grafting and tissue harvested for analysis after an additional one to four weeks. Animals were handled in accordance with NIH guidelines.

Immunohistochemistry

Tissue was fixed overnight in Carnoy's or Bouin's solution for detecting keratins (KI, K10, K5, K14, and K 17), loricrin, and filaggrin; fixation with neutral-buffered formalin was used for tissues immunostained with Lef-1, Ki67, and hair keratin (AE13) antibodies. Samples were embedded in paraffin and 8 m sections cut for immunostaining. Immunoreactivity of antigens in formalin-fixed sections was restored by immersing slides in a boiling 0.01M citrate buffer, pH 6, for 10 minutes. The following primary antibodies were used at the indicated dilutions for immunostaining: rabbit anti-keratins K 1, K 10, K5 and K 14 (1:500) (Roop et al., 1984), loricrin and filaggrin (1:500) (Roop et al., 1987), supplied by Dr. Stuart Yuspa; rabbit anti-K17 (1:1000) (McGowan and Coulombe, 1998), provided by Dr. Pierre Coulombe; rabbit anti-Lef-1 (1:200) (Travis et al., 1991), a gift from Dr. Rudolf Grosschedl; rabbit anti-Ki67, NCL-Ki67p (Novocastra Laboratories, Ltd., Newcastle upon Tyne, UK) (1:200); and mouse monoclonal AE 13 hybridoma supernatant, which recognize type I hair keratins (1:5) (Lynch et al., 1986), provided by Dr. Tung-Tien Sun. Tissue sections were incubated with primary antibodies diluted in tris-buffered saline containing 1% bovine serum albumin, typically for 1-2 hours at room temperature. Subsequent immunostaining procedures were performed using peroxidase Vectastain ABC kits (Vector Laboratories, Inc., Burlingame, Calif.) and 3,3'diaminobenzidine (Sigma, St. Louis, Mo.) as a substrate, according to the manufacturers' recommendations. Sections were counterstained with hernatoxylin and mounted using Permount (Fisher Scientific, Pittsburgh, Pa.).

In Situ Hybridization

Non-radioactive RNA in situ hybridization was performed on 5 m sections essentially as described (Groves et al., 1995), using previously described sequences for Gli1 (Walterhouse et al., 1993), Ptc1 (Goodrich et al., 1996), and BMP-4 (Jones et al., 1991).

Vibrissa Follicle Explants

Vibrissa follicle explants were established using CD-I mouse embryos at 13.5 days of gestation according to a previously described protocol (Hirai et al., 1989), with minor midifications. Vibrissa pads were transferred onto Nuclepore filters (13 mm, 8 m pores), and floated on, 2 ml of medium [DMEM (Life Technologies, Gaithersburg, Md.)+Ham's F12 medium (Life Technologies) (1:1), with 1% FCS (Intergen, Purchase, N.Y.), penicillin (50 units/ml) and streptomycin (50 gg/ml) (Life Technologies)] in 6-well plates. Similar results were obtained using a DMEM-based medium, without the addition of Ham's F12. Explants were fed fresh medium every two days. Microdissection was performed with the aid of a Nikon SMZ-2T stereomicroscope and photomicrographs were taken using an Olympus OM-4 camera. Cyclopamine was stored at −20 as a 10 mM stock in 95% EtOH.

RNA Isolation and RT-PCR

RNA was obtained by solubilizing individual explants in TriZol (Life Sciences) and isolating as recommended by the manufacturer. cDNA was synthesized using SuperScript II Rnase H reverse transcriptase with random primers (Life Technologies), and RT-PCR performed using the following primers: MHKA1 (318 bp product), (forward 5'-ATCA-GAGAATGCCAGGTTGG-3' and reverse 5'-TCATTGAG-CACACGGTTCAG-3'); hacl-1 (308 bp product), (forward 5'-TTGTATCTCCACTCCTGCCC.3 and reverse 5'-AGACTCCACAGGTTGGTTGG-3'); profilaggrin (330 bp product), (forward 5-GCTTAAATGCATCTCCAG-3' and reverse 5'-AGTCAGTCCTATTGCAGG-3') (Bickenbach et al., 1995); P actin (421 bp product), (for-ward 5'-TACCACAGGCATTGTGATGGA-3' and reverse 5'CAACGTCACACTTCATGATGG-3') (Walterhouse et al., 1993). The following PCR conditions were used for MHKA1, Hacl-1, and actin: 95×3 min "hot start"; 95×50 sec, 58×30 sec, and 72×60 sec for 25 (actin) or 35 cycles (MHKA I and Hacl-1); 72×7 min. PCR conditions for profilaggrin primers were as previously described (Bickenbach et al., 1995). Reaction products were run through 1.5% agarose gels and visualized with ethidiurn bromide.

Results and Discussion

Early stages of hair follicle development appeared similar in control and Shh −/− embryos. Hair germs, consisting of clusters of columnar basal keratinocytes protruding into the developing dermis with associated dermal condensates, were detected in the skin of both mutant and control embryos at 15.5 days of gestation (FIG. 8 A,B). Despite the similar morphology of control and Shh-deficient hair germs, a dramatic difference in gene expression patterns was revealed by in situ hybridization. The level of Gli1 mRNA was markedly reduced in both the epithelial and mesenchymal components of Shh −/− primary hair germs (FIGS. 8C,D). In addition, expression of Ptc1 was reduced in Shh mutant hair germs, although some placodes contained levels slightly above background (FIGS. 8E,F). These findings are consistent with previous reports identifying Shh as a positive regulator of both Gli1 and Ptc1 (Marigo and Tabin, 1996; Marigo et al., 1996; Lee et al., 1997; Sasaki et al., 1997), and suggest that Shh is signaling in both the epithelial and mesenchymal cells of the developing follicle. In contrast to Gli1 and Ptc1, BMP-4 mRNA was clearly detectable in condensates of mutant and control embryos (FIG. 8G,H), arguing against a requirement for Shh in the induction of BMP-4 expression. Thus, although Shh is not required for the initiation of hair follicle development, primary hair germs that arise in Shh mutant skin are deficient in the expression of at least some Shh target genes.

Figure 9A:
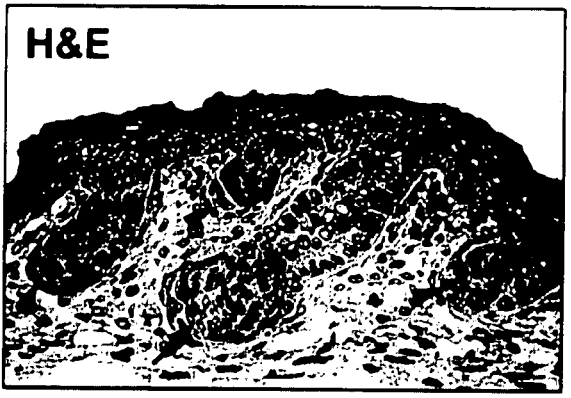
Figure 9B:
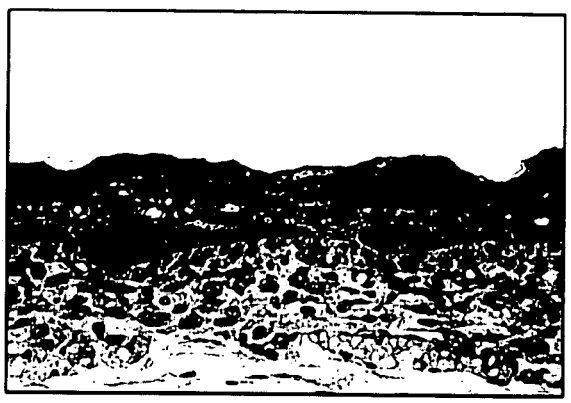

In control embryos, the interval between E15.5 and E17.5 is marked by rapid proliferation and downgrowth of the follicle into the developing dermis, accompanied by a several-fold increase in the mass of the follicle epithelium and reorganization into distinct cellular compartments. In the most mature follicles, keratinocytes in the most peripheral cell layer, which give rise to the outer root sheath in the mature follicle, have assumed a columnar arrangement perpendicular to the long axis of the developing follicle; cells located centrally are without a definite orientation at this stage but will eventually be replaced by the three concentric layers of inner root sheath cells and the three cell types comprising the hair shaft; and the epithelial cells of the deepest portion of the follicle, the future hair bulb, have surrounded what. is at this stage a well-defined cluster of mesenchymal cells, the dermal papilla (FIG. 9A, arrow). Even the less mature follicles exhibit an organized "cap" of mesenchymal cells at their invaginating tips (FIG. 9A, arrowheads). In striking contrast, hair follicles in skin from mutant embryos at E 17.5 failed to develop past the hair germ stage seen at E 15.5 (FIG. 9B). Although the follicle epithelium was most obviously affected due to its lack of growth, organizing dermal condensates and dermal papillae were conspicuously absent in mutant skin. These results are consistent With the idea that epidermis-derived Shh (Bitgood and McMahon, 1995; Iseki et al., 1996; Oro et al., 1997; Motoyama et al., 1998) functions as a paracrine signal regulating development of the mesenchymal component of the hair follicle. Inhibition of follicle formation is not likely to be due to a general disruption of skin development since epidermal morphogenesis, marked by the appearance of granular and cornified cell layers, took place by E 17.5 in both control and mutant embryos (FIGS. 9A,B).

Figure 9C:
Figure 9D:
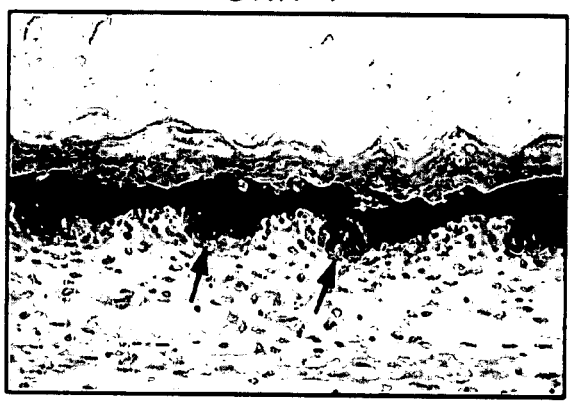
Figure 9E:
Figure 9F:

Additional studies were performed to determine whether Shh influenced the expression of epithelial differentiation markers in embryonic skin. Keratinocytes in developing hair follicles can be distinguished by a relative deficiency of K5 and K14, keratins that are abundant in surrounding epidermal basal cells (Kopan and Fuchs, 1989; Byrne et al., 1994). Immunohistochemical staining of E17.5 embryos revealed greatly reduced or undetectable levels of K14 in a subpopulation of cells comprising the normal follicles in control embryos as well as the primordial follicles seen in Shh −/− embryos (FIG. 9C,D; arrows). Moreover, K17, which is normally not detected in interfollicular epidermis but is expressed in developing and mature hair follicles (Panteleyev et al., 1997; McGowan and Coulombe, 1998), was localized to the follicular epithelium in both control and mutant skin (FIG. 9E,F). Thus, although morphogenesis of hair follicles in Shh −/− skin fails to progress past the hair germ stage, these structures contain epithelial cells that have initiated a terminal differentiation program characteristic of developing follicle keratinocytes. Consistent with the morphological findings in FIGS. 9A and B, the expression level of epidermal-specific differentiation markers (keratins 1 and 10, loricrin, and filaggrin) in Shh −/− skin was similar to or greater than in control epidermis, based on immunchistochernical. staining (data not shown).

Figure 10A:
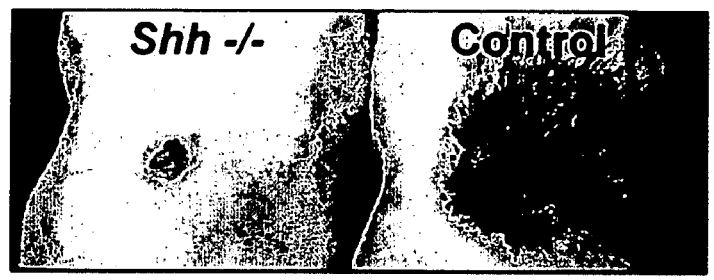
Figure 10B:
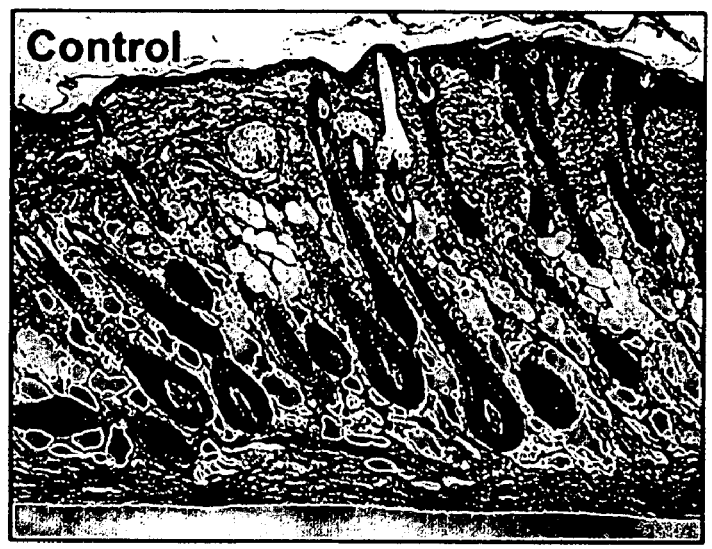
Figure 10C:
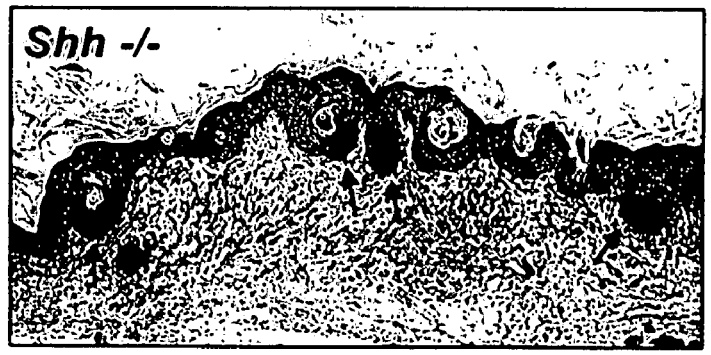
Figure 10D:
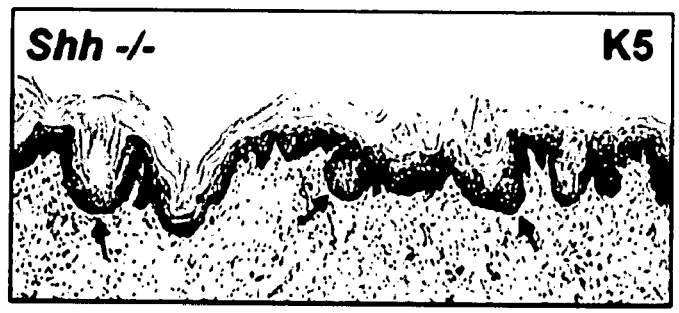
Figure 10E:
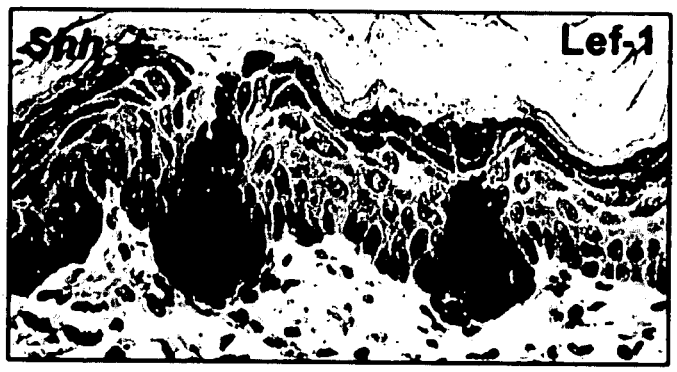
Figure 10F:
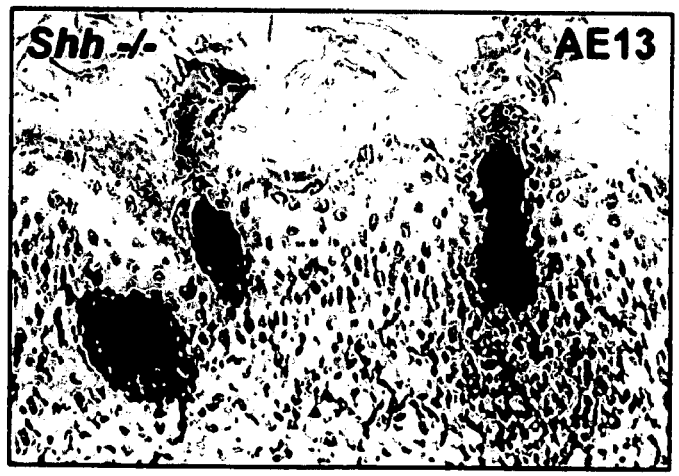

Since Shh −/− mice are not viable, post-natal analysis of mutant skin was performed following grafting onto nude mice. Whereas skin from control mice produced abundant pigmented hairs, transplanted Shh −/skin failed to generate detectable hairs but exhibited a pigmented graft site, consistent with the strain of donor skin (FIG. 10A). The histology of control skin grafts revealed the typical structures seen in normal mouse skin, including numerous hair follicles and sebaceous glands (FIG. 10B). In striking contrast, mutant skin failed to produce normal-appearing follicles, hair shafts, or sebaceous glands, but in some cases (3 of a total of 7 Shh −/− grafts), exhibited a thickened epidermis with focal areas of hyperkeratosis (FIG. 10C). Conspicuous aggregates of basophilic cells with scant cytoplasm were detected at the dermal-epidermal junction in these mutant grafts (FIG. 10C, arrows). Interestingly, the morphology of cells in the Shh-deficient keratinocyte aggregates was reminiscent of cells in control hair bulbs, and additional analyses revealed biochemical similarities. Cells in these aggregates were unreactive with K5 antibodies (FIG. 10D, arrows), exhibited abundant nuclear Lef-1 expression (FIG. 10 E) (Zhou et al., 1995), and contained a high proportion of proliferating cells detected by Ki67 immunostaining (data not shown). Interestingly, short columnar structures resembling abortive hair shafts Were associated with some of the Shh mutant keratinocyte aggregates. Moreover, these structures expressed hair-specific keratin (FIG. 10F), indicating that an advanced stage in the follicle differentiation program was achieved despite a dramatic disruption of normal morphogenesis. Rarely, a small cluster of mesenchymal cells was seen associated with the base of a keratinocyte aggregate, as illustrated in FIG. 10E, where these cells immunostain with Lef-1 antibody These findings suggest that a rudimentary dermal papilla is present in at least some of the hair germs seen in Shh mutant grafts.

Figure 11A:
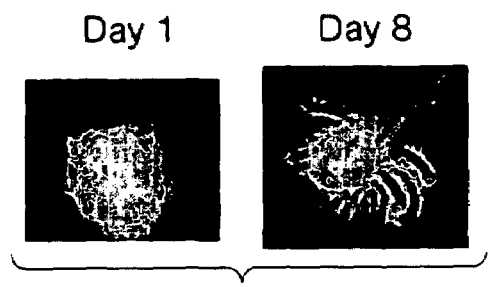
Figure 11B:
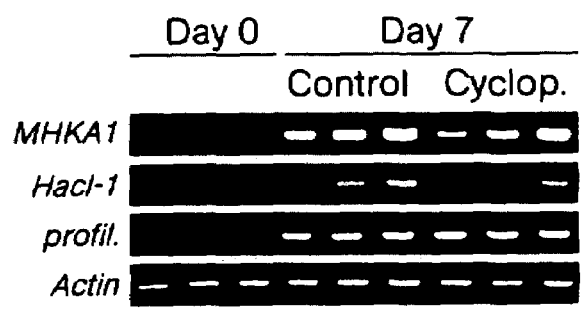
Figure 11C:
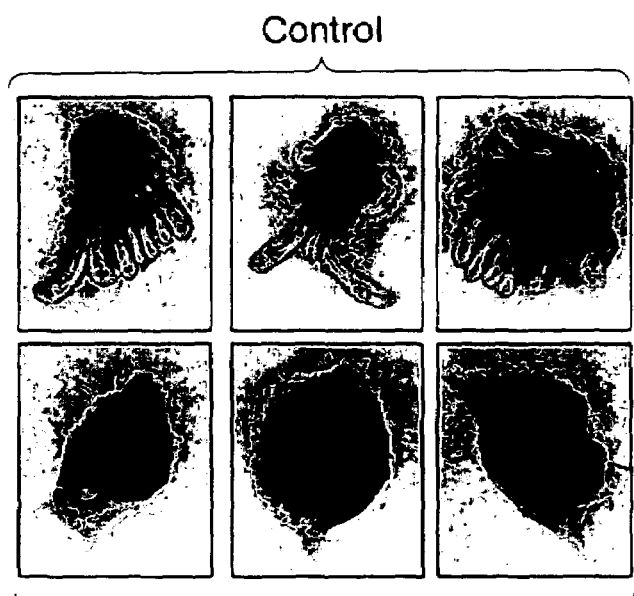

To better define the temporal requirement for Shh during follicle development, tissue culture studies were performed using cyclopamine (GaTield and Keeler, 1996), which has recently been shown to block Shh signaling in neural plate explants (Cooper et al., 1998; Incardona et al., 1998). Explants were established using vibrissa pads obtained from mice at 13.5 days of gestation (Hirai et al., 1989). When grown for six to eight days in culture, explants undergo robust morphogenesis resulting in the formation of elongated, grossly normal-appearing vibrissa follicles (FIG. 11A). These follicles contained hair shafts and expressed genes encoding mouse hair keratin A I (MHKA 1) (Kaytes et al., 1991) and a hair cortex-specific marker Hacl-1 (Huh et al., 1994), detected by RT-PCR (FIG. 11B). Treatment of explants with cyclopamine results in striking inhibition of morphogenesis, indicating that Shh signaling is required during or shortly after the hair germ stage of vibrissa. follicle development (FIG. 11C). In keeping with our results obtained using Shh mutant skin, hair-specific transcripts are detected in cyclopamine-treated grafts (FIG. 11B) despite their altered development, providing further support for the notion that biochemical differentiation of the follicle is not necessarily coupled to its morphogenesis. Both control and cyclopamine-treated explants accumulate profilaggrin mRNA, indicating that disruption of Shh signaling does not inhibit epidermal differentiation.

Collectively, the results of our studies reveal an obligatory role for Shh in the progression of hair follicle morphogenesis past the hair germ stage of development. The reduced expression of Ptc1 and Gli1 in Shh −/− dermal condensates, coupled with their failure to evolve into recognizable dermal papillae, argue that Shh is involved in regulating development of the mesenchymal component of the hair follicle, although a requirement for Shh signaling in the epithelial component of the follicle cannot be excluded. In the absence of dermal papillae normal hair follicle morphogenesis does not proceed, underscoring the critical influence these cells have on growth and remodeling of developing follicle epithelium (Jahoda et al., 1984; Weinberg et al., 1993).

Interestingly, biochemical differentiation of the follicle can take place in the absence of normal morphogenesis, implying that these two processes are regulated independently in this organ. Additional experiments will be required to formally define which component of the developing follicle is functionally impaired in Shh −/− embryos, and to determine whether Shh has additional roles at later stages of follicle development or during hair cycling. We anticipate that these studies may ultimately help explain how constitutive activation of the Shh signaling pathway in keratinocytes contributes to the formation of basal cell carcinoma (Johnson et al., 1996; Hahn et al., 1996; Oro et al., 1997; Fan et al., 1997; Xie et al., 1998).

REFERENCES FOR EXAMPLE

Bickenbach, J. R, Greer, J. M., Bundman, D. S., Rothnagel, J. A., and Roop, D. R. (1995). Loricrin expression is coordinated with other epidermal proteins and the appearance of lipid lamellar granules in development. *J. Invest. Dermatol.* 104, 405-410.

Bitgood, M. J. and McMahon, A. P. (1995). Hedgehog and Bmp genes are coexpressed at many diverse sites of cell-cell interaction in the mouse embryo. *Dev Biol.* 172, 126-138.

Byrne, C., Tainsky, M., and Fuchs, E. (1994). Programming gene expression in developing epidermis. *Development* 120, 2369-2383.

Chiang, C., Litingtung, Y., Lee, E., Young, K. E., Corden, J. L., Westphal, H., and Beachy, P. A. (1996). Cyclopia and defective axial patterning in mice lacking Sonic hedgehog gene function. *Nature* 383, 407-413.

Cooper, M. K., Porter, J. A., Young, K. E., and Beachy, P. A. (1998). Teratogen-mediated inhibition of target tissue response to Shh signaling. *Science* 280, 1603-1607.

Cotsarelis, G. (1997). The hair follicle: dying for attention. *Am. J. Pathol.* 151, 1505-1509.

Cotsarelis, G., Sun, T. T., and Lavker, R. M. (1990). Label-retaining cells reside in the bulge area of pilosebaceous unit: implications for follicular stem cells, hair cycle, and skin carcinogenesis. *Cell* 61, 1329-1337.

Dlugosz, A. A., Glick, A. B., Tennenbaum, T., Weinberg, W. C., and Yuspa, S. H. (1995). Isolation and utilization of epidermal keratinocytes for oncogene research. *Methods Enzymol.* 254, 3-20.

Fan, H., Oro, A. E., Scott, M. P., and Khavari, P. A. (1997). Induction of basal cell carcinoma features in transgenic human skin expressing Sonic Hedgehog. *Nat. Med.* 3, 788-792.

Gaffield, W. and Keeler, R. F. (1996). Steroidal alkaloid teratogens: Molecular probes for investigation of craniofacial malformations. *Journal Of Toxicology-Toxin Reviews* 15, 303-326.

Goodrich, L X, Johnson, R. L., Milenkovic, L., McMahon, J. A., and Scott, M. P. (1996). Conservation of the hedgehoglpatched signaling pathway from flies to mice: Induction of a mouse patched gene by Hedgehog. *Genes Dev* 10, 301-312.

Groves, A. K., George, K. M., Tissier-Seta, J. P., Engel, J. D., Brunet, J. F., and Anderson, D. J. (1995). Differential regulation of transcription factor gene expression and phenotypic markers in developing sympathetic neurons. *Development* 121, 887-901.

Gurdon, J. B. (1992). The generation of diversity and pattern in animal development. *Cell* 68, 185-199.

Hahn, H., Wicking, C., Zaphiropoulous, P. G., Gailani, M. R., Shanley, S., Chidambaram, A., Vorechovsky, I., Holmberg, E., Unden, A. B., Gillies, S., Negus, K., Smyth, I., Pressman, C., Leffell, D. J., Gerrard, B., Goldstein, A. M., Dean, M., Toftgard, R., Chenevix-Trench, G., Wainwright, B., and Bale, A. E. (1996). Mutations of the human homolog of Drosophila patched in the nevoid basal cell carcinoma syndrome. *Cell* 85, 841-851.

Hammerschmidt, M., Brook, A., and McMahon, A. R (1997). The world according to hedgehog. *Trends. Genet.* 13, 14-21.

Hansen, L. A. and Tennant, R. W. (1994). Follicular origin of epidermal papillomas in v-Ha-ras transgenid TG.AC mouse skin. *Proc. Natl. Acad, ScL USA* 91, 7822-7826.

Hardy, M. H. (1992). The secret life of the hair follicle. *Trends. Genet.* 8, 55-61.

Hirai, Y., Nose, A., Kobayashi, S., and Takeichi, M. (1989). Expression and role of E- and P-cadherin adhesion molecules in embryonic histogenesis. 11. Skin morphogenesis. *Development* 105, 271-277.

Huh, N., Kashiwagi, M., Konishi, C., Hashimoto, Y., Kohno, Y., Nomura, S., and Kuroki, T. (1994). Isolation and characterization of a novel hair follicle-specific gene, Hacl-1. *J Invest. Dermatol.* 102, 716-720.

Incardona, J. P., Gaff teld, W., Kapur, R. P., and Roelink, H. (1998). The teratogenic Veratrum alkaloid cyclopamine inhibits Sonic hedgehog signal transduction. *Development* 128, 3553-3562.

Iseki, S., Araga, A., Ohuchi, H., Nohno, T., Yoshioka, H., Hayashi, F., and Noji, S. (1996). Sonic hedgehog is expressed in epithelial cells during development of whisker, hair, and tooth. *Biochem. Biophys. Res. Commun.* 218, 688-693.

Jahoda, C. A., Home, K. A., and Oliver, R. F. (1984). Induction of hair growth by implantation of cultured dermal papilla cells. *Nature* 311, 560-562.

Johnson, R. L., Rothman, A. L., Xie, J., Goodrich, L. V., Bare, J. W., Bonifas, J. M., Quinn, A. G., Myers, R. M., Cox, D. R., Epstein, E. H., Jr., and Scott, M. P. (1996). Human homolog of patched, a candidate gene for the basal cell nevus syndrome. *Science* 272, 1668-1671.

Jones, C. M., Lyons, K. M., and Hogan, B. L. (1991). Involvement of Bone Morphogenetic Protein-4 (BMP4) and VgrI in morphogenesis and neurogenesis in the mouse. *Development* U1, 531-542.

Kaytes, P. S., McNab, A. R., Rea, T. J., Groppi, V., Kawabe, T. T., Buhl, A. E., Bertolino, A. P., Hatzenbuhler, N. T., and Vogeli, G. (1991). Hairspecific, keratins: characterization and expression of a mouse type I keratin gene. *J. Invest. Dermatol.* 97, 835-842.

Kopan, R. and Fuchs, E. (1989). A new took into an old problem: keratins as tools to investigate determination, morphogenesis, and differentiation in skin. *Genes. Dev.* 3, 1-15.

Lavker, R. M., Miller, S., Wilson, C., Cotsarelis, G., Wei, Z. G., Yang, J. S., and Sun, T. T. (1993). Hair follicle stem cells: their location, role in hair cycle, and involvement in skin tumor formation. *J. Invest. Dermatol.* 101, 16S-26S.

Lee, J., Platt, K. A., Censullo, P., and Ruiz i Altaba, A. (1997). Gli1 is a target of Sonic hedgehog that induces ventral neural tube development. *Development* 124, 2537-2552.

Lynch, M. H., O'Guin, W. M., Hardy, C., Mak, L., and Sun, T. T. (1986). Acidic and basic hair/nail ("hard") keratins: their colocalization in upper cortical and cuticle cells of the human hair follicle and their relationship to "soft" keratins. *J. Cell Biol.* 103, 2593-2606.

Marigo, V., Johnson, R. L., Vortkamp, A., and Tabin, C. J. (1996). Sonic hedgehog differentially regulates expression of GLI and GL13 during limb development. *Dev Biol.* 180, 273-283.

Marigo, V. and Tabin, C. J. (1996). Regulation of Patched by Sonic hedgehog in the developing neural tube. *Proc. Nad. Acad. ScL USA* 93, 9346-9351.

McGowan, K. and Coulombe, P. A. (1998). Expression of keratin 17 coincides with the determination of major epithelial lineages during mouse skin development. *J. Cell. Biol.* (in press)

Millar, S. (1997). The Role of Patterning Genes in Epidermal Differentiation. In "Cytoskeletal-Membrane Interactions and Signal Transduction" (P. Cowin and M. W. Klymkowsky, Eds.), pp. 87-102. Landes Bioscience, Austin, Tex..

Motoyama, J., Takabatake, T., Takeshima, K., and Hui, C. (1998). Ptch2, a second mouse Patched gene is coexpressed with Sonic hedgehog. *Nat. Genet.* 18, 104-106.

Oro, A. E., Higgins, K. M., Hu, Z. L., Bonifas, J. M., Epstein, E. H., Jr., and Scott, M. P. (1997). Basal cell carcinomas in mice overexpressing sonic hedgehog. *Science* 276, 817-821.

Panteleyev, A. A., Paus, R., Wanner, R., Numberg, W., Eichmuller, S., Tliiel, R., Zhang, J., Henz, B. M., and Rosenbach, T. (1997). Keratin 17 gene expression during the murine hair cycle. *J. Invest. Dermatol* 108, 324-329.

Rochat, A., Kobayashi, K., and Barrandon, Y. (1994). Location of stem cells of human hair follicles by clonal analysis. *Cell* 76, 1063-1073.

Roop, D. R., Cheng, C. K., Titterington, L., Meyers, C. A., Stanley, J. R., Steinert, P. M., and Yuspa, S. H. (1984). Synthetic peptides corresponding to keratin subunits elicit highly specific antibodies. *J. Biol. Chem.* 259, 8037-8040.

Roop, D. R., Huitfeldt, H., Kilkenny, A., and Yuspa, S. H. (1987). Regulated expression of differentiation-associated keratins in cultured epidermal cells detected by monospecific antibodies to unique peptides of mouse epidermal keratins. *Differentiation* 35, 143-150.

Rosenquist, T. A. and Martin, G. R. (1996). Fibroblast growth factor signalling in the hair growth cycle: expression of the fibroblast growth factor receptor and ligand. genes in the murine hair follicle. *Dev. Dyn.* 205, 379-386.

Sasaki, H., Hui, C., Nakaftiku, M., and Kondoh, H. (1997). A binding site for Gli proteins is essential for HNF-3beta floor plate enhancer activity in transgenics and can respond to Shh in vitro. *Development* 124, 1313-1322.

Sengel, P. (1976). "Morphogenesis of Skin." Cambridge University Press, Cambridge.

Sterm, K. S., Combates, N. J., Eilertsen, K-J., Gordon, J. S., Pardinas, J. R., Parimoo, S., and Prouty, S. M. (1996). Hair follicle growth controls. *Dermatol Clin.* 14, 543-558.

Thesleff, I., Vaahtokari, A., and Partanen, A. M. (1995). Regulation of organogenesis. Common molecular mechanisms regulating the development of teeth and other organs. *Int. J. Dev. Biol.* 39, 35-50.

Travis, A., Amsterdam, A., Belanger, C., and Grosschedl, R. (1991). LEF-1, a gene encoding a lymphoid-specific protein with an HMG domain, regulates T-cell receptor alpha enhancer function. *Genes Dev.* 5, 880-894.

Walterhouse, D., Ahmed, M., Slusarski, D., Kalamaras, J., Boucher, D., Holmgren, R., and Iannaccone, P. (1993). gli, a zinc finger transcription factor and oncogene, is expressed during normal mouse development. *Dev. Dyn.* 196, 91-102.

Weinberg, W. C., Goodman, L. V., George, C., Morgan, D. L., Ledbetter, S., Yuspa, S. H., and Lichti, U. (1993).

Reconstitution of hair follicle development in vivo: determination of follicle formation, hair growth, and hair quality by dermal cells. *J. Invest. Dermatol.* 100, 229-236.

Widelitz, R. B., Jiang, T X, Noveen, A., Ting-Berreth, S. A., Yin, E., Jung, H. S., and Chuong, C. M. (1997). Molecular histology in skin appendage morphogenesis. *Mi~rosc. Res. Tech.* 38, 452-465.

Xie, J., Murone, M., Luoh, S. M., Ryan, A., Gu, Q., Zhang, C., Bonifas, J. M., Lam, C. W., Hynes, M., Goddard, A., Rosenthal, A., Epstein, E. H. J., and deSauvage, F. (1998). Activating Smoothened mutations in sporadic basal-cell carcinoma. *Nature* 391, 90-92.

Zhou, P., Byrne, C., Jacobs, J., and Fuchs, E. (1995). Lymphoid enhancer factor I directs hair follicle patterning and epithelial cell fate. *Genes Dev.* 9, 700-713.

EXAMPLE 3

Rescue of ptc Loss-of-Function Phenotype

Based on the results presented above, we have attempt to determine the site in the Shh signaling pathway at which cyclopamine operates, and therefor better understand the spectrum of tumors caused by Shh pathway-activating lesions that could potentially be treated with this compound.

These studies involve the use of mouse embryonic fibroblasts (MEFs) that were generated by trypsin digestion of E8.5 embryos from patched (ptc)+/− matings. The mouse ptc gene was disrupted by homologous recombination in which part of exon1 and all of exon 2 were replaced with the bacterial lacZ gene (Goodrich et al, (1997) Science 277: 1109). As Ptc protein suppresses Shh signaling, a loss of its function activates the Shh signaling pathway. Shh signaling, through a cascade of events, is mediated by the Gli transcription factors. One of the target genes of Shh signaling is ptc, through Gli-binding sites in the ptc promoter region, and this serves as a feedback mechanism for down regulation of signaling. Thus, in these ptc −/− embryos, the Shh signaling pathway is activated in many tissues, and the lacZ gene product β-galactosidase is expressed in all of those tissues as a report of pathway activation.

We obtained these MEFs to determine whether cyclopamine acts on Ptc or another, component of the cascade to inhibit Shh signaling. If the target of cyclopamine is Ptc, then one would expect that when the Shh pathway is activated by the loss of ptc function, it could no longer be inhibited by cyclopamine. FIG. 12 demonstrates that the Shh signaling pathway can be activated in these fibroblasts in cell culture, and that the level of β-galactosidase activity does reflect the degree of pathway activation. The MEF line 23-4 is heterozygous for ptc-lacZ, and thus contains one functional ptc allele capable of maintaining a repressed state of the pathway, but will express lacZ when the pathway is activated by addition of Shh protein (see FIG. 12).

In contrast, the β-galactosidase activity in MEFs homozygous for ptc-lacZ, (cell line 23-1) is markedly elevated, because in these cells the pathway is constitutively activated by the loss of a functional ptc allele (FIG. 13). When these cells are cultured with cyclopamine, β-galactosidase activity is decreased, indicating that when the Shh signaling pathway is unregulated by Ptc repression, it is still sensitive to cyclopamine inhibition. The reduction of β-galactosidase activity appears to result from the specific inhibition of Shh signaling, rather than from cell toxicity because enzymatic activity is normalized to whole protein content of the sample. Also, the reduction of β-galactosidase activity can be obtained with exposure to cyclopamine over a period of time that is shorter than the average cell cycle, and so does not appear to be due solely to an inhibition of cell proliferation (FIG. 14).

A final indication that this represents specific inhibition of Shh signaling is that it cannot be achieved with a non-inhibitory, but structurally related compound tomatidine (FIG. 15).

All of the references cited above are hereby incorporated by reference herein.

EQUIVALENTS

Those skilled in the art will recognize, or be able to ascertain using no more than routine experimentation, many equivalents to the specific embodiments of the invention described herein. Such equivalents are intended to be encompassed by the following claims.

The invention claimed is:

1. A method for inhibiting mitotic cell proliferation in an animal, wherein the mitotic cell proliferation is associated with a cancer, comprising administering to the animal a purified compound represented in the general formula (I), or unsaturated forms thereof, or pharmaceutically acceptable salts thereof:

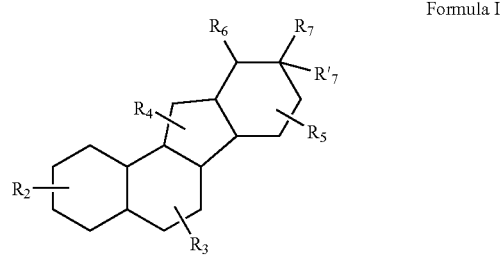

Formula I wherein, as valence permits, $R_2$, $R_3$, $R_4$, and $R_5$ independently for each occurrence, represent one or more substituents selected from hydrogen, halogens, alkyls, alkenyls, alkynyls, aryls, hydroxyl, =O, =S, alkoxyl, silyloxy, amino, nitro, thiol, amines, imines, amides, phosphoryls, phosphonates, phosphines, carbonyls, carboxyls, carboxamides, anhydrides, silyls, ethers, thioethers, alkylsulfonyls, arylsulfonyls, selenoethers, ketones, aldehydes, esters, or —$(CH_2)_m$—$R_8$;

$R_6$ is absent or is selected from halogens, alkyls, alkenyls, alkynyls, aryls, hydroxyl, =O, =S, alkoxyl, silyloxy, amino, nitro, thiol, amines, imines, amides, phosphoryls, phosphonates, phosphines, carbonyls, carboxyls, carboxamides, anhydrides, silyls, ethers, thioethers, alkylsulfonyls, arylsulfonyls, selenoethers, ketones, aldehydes, esters, or —$(CH_2)_m$—$R_8$;

$R_7$ and $R'_7$, taken together with the carbon atom to which they are attached, form a furo[3,2-b]piperidine ring system, wherein the carbon atom to which $R_7$ and $R'_7$ are attached is the carbon atom at the 2-position of the furo[3,2-b]piperidine ring system;

$R_8$ represents an aryl, a cycloalkyl, a cycloalkenyl, a heterocycle, or a polycycle; and m is an integer in the range 0 to 8 inclusive.

2. A method for inhibiting mitotic cell proliferation in an animal, wherein the mitotic cell proliferation is associated with a cancer, comprising administering to the animal a purified compound represented in the general formula (II), or unsaturated forms thereof, or pharmaceutically acceptable salts thereof:

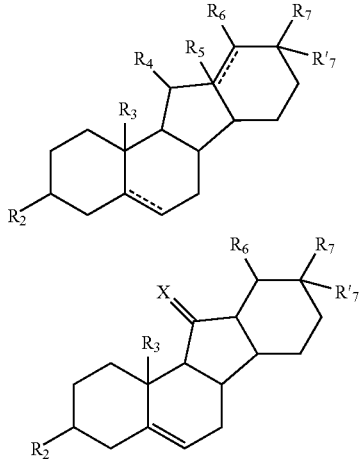

Formula II wherein, as valence permits, $R_2$ and $R_4$, independently for each occurrence, are selected from hydrogen, halogens, alkyls, alkenyls, alkynyls, aryls, hydroxyl, =O, =S, alkoxyl, silyloxy, amino, nitro, thiol, amines, imines, amides, phosphoryls, phosphonates, phosphines, carbonyls, carboxyls, carboxamides, anhydrides, silyls, ethers, thioethers, alkylsulfonyls, arylsulfonyls, selenoethers, ketones, aldehydes, esters, or —$(CH_2)_m$—$R_8$;

$R_3$, independently for each occurrence, is selected from hydrogen, halogens, alkyls, alkenyls, alkynyls, aryls, hydroxyl, alkoxyl, silyloxy, amino, nitro, thiol, amines, imines, amides, phosphoryls, phosphonates, phosphines, carbonyls, carboxyls, carboxamides, anhydrides, silyls, ethers, thioethers, alkylsulfonyls, arylsulfonyls, selenoethers, ketones, aldehydes, esters, or —$(CH_2)_m$—$R_8$;

$R_5$, independently for each occurrence, is absent or represents a substituent selected from hydrogen, halogens, alkyls, alkenyls, alkynyls, aryls, hydroxyl, alkoxyl, silyloxy, amino, nitro, thiol, amines, imines, amides, phosphoryls, phosphonates, phosphines, carbonyls, carboxyls, carboxamides, anhydrides, silyls, ethers, thioethers, alkylsulfonyls, arylsulfonyls, selenoethers, ketones, aldehydes, esters, or —$(CH_2)_m$—$R_8$;

$R_6$ is absent or is selected from halogens, alkyls, alkenyls, alkynyls, aryls, hydroxyl, =O, =S, alkoxyl, silyloxy, amino, nitro, thiol, amines, imines, amides, phosphoryls, phosphonates, phosphines, carbonyls, carboxyls, carboxamides, anhydrides, silyls, ethers, thioethers, alkylsulfonyls, arylsulfonyls, selenoethers, ketones, aldehydes, esters, or —$(CH_2)_m$—$R_8$;

$R_7$ and $R'_7$, taken together with the carbon atom to which they are attached, form a furo[3,2-b]piperidine ring system, wherein the carbon atom to which $R_7$ and $R'_7$ are attached is the carbon atom at the 2-position of the furo[3,2-b]piperidine ring system;

$R_8$ represents an aryl, a cycloalkyl, a cycloalkenyl, a heterocycle, or a polycycle;

X represents O or S; and m is an integer in the range 0 to 8 inclusive.

3. The method of claim 1, wherein the compound is represented in Formula (Ia), or unsaturated forms thereof, or pharmaceutically acceptable salts thereof:

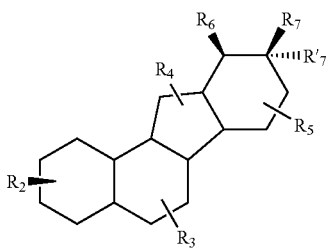

Formula Ia wherein, as valence permits, $R_2$, $R_3$, $R_4$, and $R_5$ independently for each occurrence, represent one or more substituents selected from hydrogen, halogens, alkyls, alkenyls, alkynyls, aryls, hydroxyl, =O, =S, alkoxyl, silyloxy, amino, nitro, thiol, amines, imines, amides, phosphoryls, phosphonates, phosphines, carbonyls, carboxyls, carboxamides, anhydrides, silyls, ethers, thioethers, alkylsulfonyls, arylsulfonyls, selenoethers, ketones, aldehydes, esters, or —$(CH_2)_m$—$R_8$;

$R_6$ is absent or is selected from halogens, alkyls, alkenyls, alkynyls, aryls, hydroxyl, =O, =S, alkoxyl, silyloxy, amino, nitro, thiol, amines, imines, amides, phosphoryls, phosphonates, phosphines, carbonyls, carboxyls, carboxamides, anhydrides, silyls, ethers, thioethers, alkylsulfonyls, arylsulfonyls, selenoethers, ketones, aldehydes, esters, or —$(CH_2)_m$—$R_8$;

$R_7$ and $R'_7$, taken together with the carbon atom to which they are attached, form a furo[3.2-b]piperidine ring system wherein the carbon atom to which $R_7$ and $R'_7$ are attached is at the carbon atom the 2-position of the furo[3.2-b]piperidine ring system;

$R_8$ represents an aryl, a cycloalkyl, a cycloalkenyl, a heterocycle, or a polycycle; and m is an integer in the range 0 to 8 inclusive.

4. The method of claim 2, wherein the compound is represented in Formula (IIa), or unsaturated forms thereof, or pharmaceutically acceptable salts thereof:

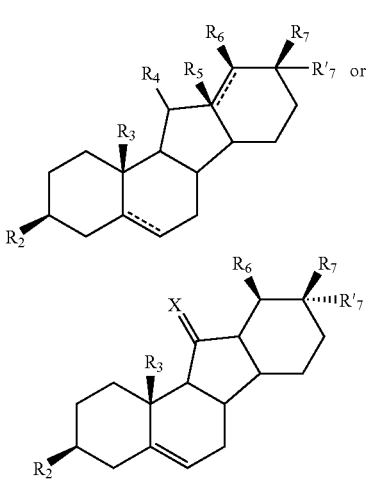

Formula IIa wherein, as valence permits, $R_2$ and $R_4$, independently for each occurrence, are selected from hydrogen, halogens, alkyls, alkenyls, alkynyls, aryls, hydroxyl, =O, =S, alkoxyl, silyloxy, amino, nitro, thiol, amines, imines, amides, phosphoryls, phosphonates, phosphines, carbonyls, carboxyls, carboxamides, anhydrides, silyls, ethers, thioethers, alkylsulfonyls, arylsulfonyls, selenoethers, ketones, aldehydes, esters, or —$(CH_2)_m$—$R_8$;

$R_3$, independently for each occurrence, are selected from hydrogen, halogens, alkyls, alkenyls, alkynyls, aryls, hydroxyl, alkoxyl, silyloxy, amino, nitro, thiol, amines, imines, amides, phosphoryls, phosphonates, phosphines, carbonyls, carboxyls, carboxamides, anhydrides, silyls, ethers, thioethers, alkylsulfonyls, arylsulfonyls, selenoethers, ketones, aldehydes, esters, or —$(CH_2)_m$—$R_8$;

$R_5$, independently for each occurrence, is absent or is selected from hydrogen, halogens, alkyls, alkenyls, alkynyls, aryls, hydroxyl, alkoxyl, silyloxy, amino, nitro, thiol, amines, imines, amides, phosphoryls, phosphonates, phosphines, carbonyls, carboxyls, carboxamides, anhydrides, silyls, ethers, thioethers, alkylsulfonyls, arylsulfonyls, selenoethers, ketones, aldehydes, esters, or —$(CH_2)_m$—$R_8$;

$R_6$ is absent or is selected from halogens, alkyls, alkenyls, alkynyls, aryls, hydroxyl, =O, =S, alkoxyl, silyloxy, amino, nitro, thiol, amines, imines, amides, phosphoryls, phosphonates, phosphines, carbonyls, carboxyls, carboxamides, anhydrides, silyls, ethers, thioethers, alkylsulfonyls, arylsulfonyls, selenoethers, ketones, aldehydes, esters, or —$(CH_2)_m$—$R_8$;

$R_7$ and $R'_7$, taken together with the carbon atom to which they are attached, form a furo[3,2-b]piperidine ring system, wherein the carbon atom to which $R_7$ and $R'_7$ are attached is the carbon atom at the 2-position of the furo[3,2-b]piperidine ring system;

$R_8$ represents an aryl, a cycloalkyl, a cycloalkenyl, a heterocycle, or a polycycle;

X represents O or S; and m is an integer in the range 0 to 8 inclusive.

5. The method of any one of claims 1-2, wherein the compound is administered topically.

6. The method of any one of claims 1-2, wherein $R_2$ and $R_3$, independently for each occurrence, are —OH, alkyl, —O-alkyl, —C(O)-alkyl, or —C(O)—$R_8$.

7. The method of any one of claims 1-2, wherein $R_4$, independently for each occurrence represents —OH, =O, alkyl, —O-alkyl, —C(O)-alkyl, or —C(O)—$R_8$.

8. The method of any one of claims 1-2, wherein $R_6$ is selected from hydrogen, alkyls, alkenyls, alkynyls, amines, imines, amides, carbonyls, carboxyls, carboxamides, ethers, thioethers, esters, or —$(CH_2)_m$—$R_8$.

9. The method of any one of claims 1-2, wherein $R_7$ and $R'_7$, taken together with the carbon atom to which they are attached, form a perhydrofuro[3,2-b]pyridine.

10. The method of any one of claims 1-2, wherein the compound inhibits hedgehog-mediated signal transduction with an $ED_{50}$ of 1 mM or less.

11. The method of any one of claims 1-2, wherein the compound inhibits hedgehog-mediated signal transduction with an $ED_{50}$ of 1 µM or less.

12. The method of any one of claims 1-2, wherein the compound inhibits hedgehog-mediated signal transduction with an $ED_{50}$ of 1 nM or less.

13. The method of any one of claims 1-2, wherein the cancer is a basal cell carcinoma, medulloblastoma, squamous cell carcinoma, carcinosarcoma, adenocystic carcinoma, epidermoid carcinoma, nasopharyngeal carcinoma, renal cell carcinoma, papilloma, or an epidermoidoma.

14. The method of claim 13, wherein the cancer is a basal cell carcinoma.

15. The method of claim 13, wherein the cancer is medulloblastoma.

16. The method of any one of claims 1-2, wherein the compound is jervine or cyclopamine.

17. The method of any one of claims 1-2, wherein the furo[3,2-b]piperidine ring system is substituted with one or more halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, heterocyclyl, aromatic or heteroaromatic moieties, —$CF_3$, or —CN.

\* \* \* \* \*